(12) United States Patent
Beight et al.

(10) Patent No.: US 8,436,002 B2
(45) Date of Patent: May 7, 2013

(54) AKT INHIBITORS

(75) Inventors: Douglas Wade Beight, Frankfort, IN (US); Timothy Paul Burkholder, Carmel, IN (US); Joshua Ryan Clayton, Fishers, IN (US); MariJean Eggen, Brownsburg, IN (US); Kenneth James Henry, Jr., Carmel, IN (US); Deidre Michelle Johns, Indianapolis, IN (US); Saravanan Parthasarathy, Carmel, IN (US); Huaxing Pei, Carmel, IN (US); Mark Edward Rempala, Indianapolis, IN (US); Jason Scott Sawyer, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/391,895

(22) PCT Filed: Oct. 20, 2010

(86) PCT No.: PCT/US2010/053295
§ 371 (c)(1),
(2), (4) Date: Feb. 23, 2012

(87) PCT Pub. No.: WO2011/050016
PCT Pub. Date: Apr. 28, 2011

(65) Prior Publication Data
US 2012/0149684 A1    Jun. 14, 2012

Related U.S. Application Data

(60) Provisional application No. 61/254,308, filed on Oct. 23, 2009.

(51) Int. Cl.

| | | |
|---|---|---|
| *A01N 43/54* | (2006.01) |
| *A01N 43/90* | (2006.01) |
| *A01N 43/42* | (2006.01) |
| *A01N 43/40* | (2006.01) |
| *A61K 31/517* | (2006.01) |
| *A61K 31/519* | (2006.01) |
| *A61K 31/44* | (2006.01) |
| *A61K 31/445* | (2006.01) |

(52) U.S. Cl.
USPC ............ 514/258.1; 514/262.1; 514/264.1; 514/322; 514/396; 514/303; 544/257; 544/258; 544/224; 544/242

(58) Field of Classification Search .............. None
See application file for complete search history.

(56) References Cited

U.S. PATENT DOCUMENTS

2010/0120801 A1    5/2010    Shepherd

FOREIGN PATENT DOCUMENTS

| WO | WO 2005/117909 A2 | 12/2005 |
|---|---|---|
| WO | WO 2006/046024 A1 | 5/2006 |
| WO | WO 2006/065703 A1 | 6/2006 |
| WO | WO 2006/071819 A1 | 7/2006 |
| WO | WO 2007/125310 A1 | 11/2007 |
| WO | WO 2007/125321 A2 | 11/2007 |
| WO | WO 2008/075109 A1 | 6/2008 |
| WO | WO 2008/140947 A1 | 11/2008 |

*Primary Examiner* — James D Anderson
*Assistant Examiner* — Stephanie Springer
(74) *Attorney, Agent, or Firm* — Tina M. Tucker

(57) ABSTRACT

The present invention provides AKT inhibitors of the formula: Formula I The present invention also provides pharmaceutical compositions comprising compounds of Formula I, uses of compounds of Formula I and method of using compounds of Formula I.

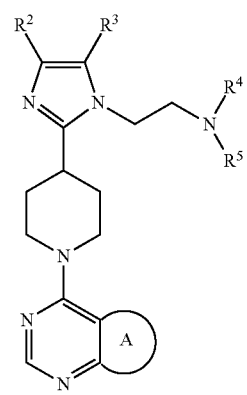

(I)

10 Claims, No Drawings

AKT INHIBITORS

This application is a §371 national phase filing of PCT Application No. PCT/US2010/053295, filed Oct. 20, 2010, which claims priority to U.S. Provisional Application No. 61/254308, filed Oct. 23, 2009.

The phosphotidylinositol-3-kinase (PI3K)/AKT/mammalian target of rapamycin (mTOR) pathway encompasses a number of signaling points which are critical in the control of cell growth and survival. AKT, also known as protein kinase B, is a serine-threonine protein kinase which has a key role in this pathway. Activation of AKT is mediated by PI3K. PI3K generates phospholipids which bind to AKT. Upon binding, AKT is recruited to the plasma membrane and is activated through phosphorylation. AKT activation and signaling promotes cell survival, growth and proliferation. Increased AKT activation has been implicated in a wide variety of cancers.

A series of substituted piperidine compounds having AKT inhibitory activity are disclosed in WO 2008/075109. These compounds are disclosed for use in the treatment of diseases or conditions comprising or arising from abnormal cell growth or abnormally arrested cell death, including cancer.

There remains a need to provide alternative AKT inhibitors which can be used in the treatment of proliferative disorders such as cancer. The present invention provides alternative AKT inhibitors. Certain compounds of the present invention are more potent AKT inhibitors than those known in the art.

Certain compounds of the present invention have low kinase 2 (ROCK2) activity compared to inhibitors known in the art. Certain compounds of the present invention have improved oral efficacy compared to AKT inhibitors known in the art.

The present invention provides compounds of the formula:

Formula I

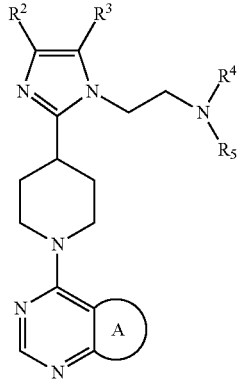

wherein:
A is

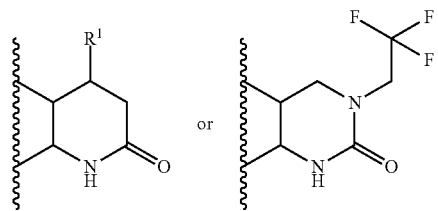

$R^1$ is $CH_3$, $CH_2CH_3$ or $CF_3$;
$R^2$ is H, $CF_3$, $CH_2CF_3$, $CH_2CH_2CF_3$, $C_1$-$C_4$ alkyl, $C_3$-$C_6$ cycloalkyl, CN, Cl, Br, $CH=CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H; or $R^2$ and $R^3$ are both Cl; and
$R^4$ is H and $R^5$ is $CH_3$, $C(CH_3)_3$, $CH(CH_3)_2$, cyclobutyl, cyclopentyl, $CH_2$-cyclopropyl, $C(CH_3)_2CH_2CH_3$ or tetrahydropyran-4-yl; or $R^4$ and $R^5$ are both $CH_3$; or $R^4$ and $R^5$ together with the N to which they are attached form a pyrrolidine, optionally substituted by hydroxy at the 3-position, or an azetidine;
or a pharmaceutically acceptable salt thereof.

The present invention provides a pharmaceutical formulation comprising a compound of the present invention, or a pharmaceutically acceptable salt thereof, and a pharmaceutically acceptable carrier, diluent, or excipient.

The present invention provides a compound of the present invention, or a pharmaceutically acceptable salt thereof, for use in therapy.

The present invention provides a compound of the present invention, or a pharmaceutically acceptable salt thereof, for use in treatment of lung cancer, breast cancer or glioblastoma. This invention further provides a method of treating lung cancer, breast cancer or glioblastoma in a mammal comprising administering to a mammal in need of such treatment an effective amount of a compound of the present invention, or a pharmaceutically acceptable salt thereof. Additionally, this invention provides the use of a compound of the present invention, or a pharmaceutically acceptable salt thereof, for the manufacture of a medicament for the treatment of lung cancer, breast cancer or glioblastoma. Furthermore, this invention provides a pharmaceutical composition for use in therapy comprising a compound of the present invention, or a pharmaceutically acceptable salt thereof, and provides a pharmaceutical composition for treating lung cancer, breast cancer or glioblastoma comprising a compound of the present invention, or a pharmaceutically acceptable salt thereof.

The present invention provides a pharmaceutical composition comprising a compound of the present invention together with a pharmaceutically acceptable carrier and optionally other therapeutic agents.

The general chemical terms used in the formulae above have their usual meanings. For example, the term "$C_1$-$C_4$ alkyl" refers to a straight or branched, monovalent, saturated aliphatic chain of one to four carbon atoms and includes, but is not limited to, methyl, ethyl, propyl, isopropyl, butyl, isobutyl, and t-butyl. Ethyl, propyl, isopropyl, butyl and isobutyl are preferred alkyl groups. Ethyl is particularly preferred.

Compounds of this invention are bases, and accordingly react with any of a number of organic and inorganic acids to form pharmaceutically acceptable salts and the present invention includes the pharmaceutically acceptable salts of the compounds of Formula I. The term "pharmaceutically acceptable salt" as used herein, refers to salts of the compounds of Formula I that are substantially non-toxic to living organisms. Such salts include the pharmaceutically acceptable salts listed in Journal of Pharmaceutical Science, 66, 2-19 (1977), which are known to the skilled artisan. In one embodiment, the compound of the present invention is the free base or the hydrochloride salt. In particular, it is the free base.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention. The specific stereoisomers and enantiomers of compounds of Formula I can be prepared by one of ordinary skill in the art utilizing well known techniques and processes, such as those disclosed by J. Jacques, et al., "Enantiomers, Racemates, and Resolutions", John Wiley and Sons, Inc., 1981, and E. L. Eliel and S. H. Wilen, "Stereochemistry of Organic Compounds", (Wiley-Interscience 1994), and European Patent Application No. EP-A-838448, published Apr. 29, 1998. Examples of resolutions include recrystallization techniques or chiral chromatography.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation "——" refers to a bond that protrudes forward out of the plane of the page. The designation "······" refers to a bond that protrudes backward out of the plane of the page.

The term "enantiomeric enrichment" refers to the increase in the amount of one enantiomer as compared to the other. A convenient method of expressing the enantiomeric enrichment achieved is the concept of enantiomeric excess, or "ee," which is found using the following equation:

$$\% \, ee = E^1 - E^2$$

wherein $E^1$ is the percentage amount of the first enantiomer and $E^2$ is the percentage amount of the second enantiomer. Enantiomeric enrichment is readily determined by one of ordinary skill in the art using standard techniques and procedures, such as gas or high performance liquid chromatography with a chiral column.

It is preferred that the carbon to which $R^1$ is attached is in the R configuration:

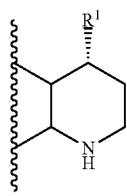

The term "R enantiomer" as used herein means that there is a % ee of the R enantiomer of greater than 90%, preferably greater than 95% and more preferably greater than 98%.

The skilled artisan will also appreciate that compounds of Formula I exist as tautomers, for example:

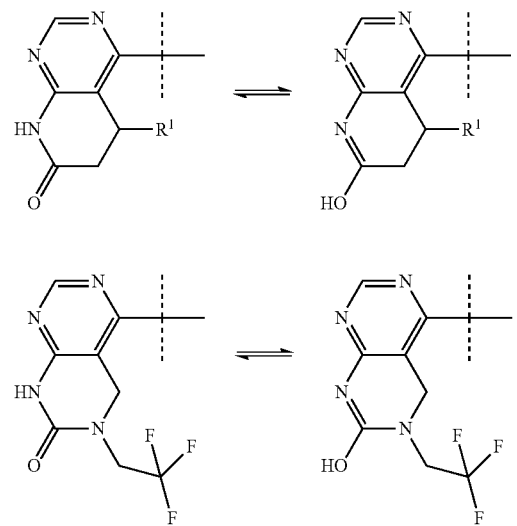

Although tautomers are structurally distinct, the skilled artisan will appreciate that they exist in equilibrium and are easily and rapidly interconvertible under ordinary conditions. (See, March, *Advanced Organic Chemistry*, Third Edition, Wiley Interscience, New York, N.Y. (1985), pages 66-70; and Allinger, Organic Chemistry, Second Edition, Worth Publishers, New York, N.Y., (1976), page 173). As such, the representation of a compound of Formula I in a single tautomeric form contemplates both tautomeric forms individually and mixtures thereof.

The exemplified compounds were named using the naming program within Chem Draw Ultra version v10 or Chem Bio Viz Ultra version v11.

In one embodiment, the present invention comprises compounds of Formula I wherein A is:

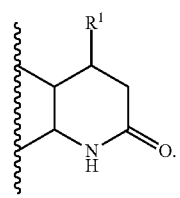

In particular, A is:

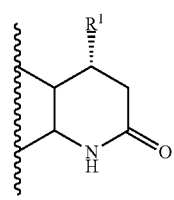

In one embodiment, $R^1$ is $CH_3$ or $CF_3$. In particular, $R^1$ is $CH_3$.

In an alternative embodiment, the present invention comprises compounds of Formula I wherein A is:

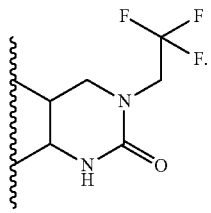

In one embodiment, the present invention comprises compounds of Formula I wherein $R^2$ is $CF_3$, $CH_2CF_3$, $CH_2CH_2CF_3$, $C_1$-$C_4$ alkyl, $C_3$-$C_6$ cycloalkyl, CN, Cl, Br, $CH$=$CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H; or $R^2$ and $R^3$ are both Cl. In particular, $R^2$ is $CF_3$, $CH_2CF_3$, $CH_2CH_2CF_3$, $CH_2CH_3$, $(CH_2)_2CH_3$, $(CH_2)_3CH_3$, $CH(CH_3)_2$, $CH_2CH(CH_3)_2$, $C_3$-$C_6$ cycloalkyl, Cl, Br, $CH$=$CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H; or $R^2$ and $R^3$ are both Cl. More particularly, $R^2$ is $CF_3$, $CH_2CF_3$, $CH_2CH_3$ or tetrahydropyran-4-yl and $R^3$ is H. Even more particularly, $R^2$ is tetrahydropyran-4-yl and $R^3$ is H.

In another embodiment, the present invention comprises compounds of Formula I wherein $R^2$ is $CF_3$, $CH_2CF_3$, $CH_2CH_2CF_3$, $CH_2CH_3$, $(CH_2)_2CH_3$, cyclopropyl, Br, $CH_2CH_2OCH_3$ or tetrahydropyran-4-yl, and $R^3$ is H. In particular, $R^2$ is $CH_2CF_3$, $CH_2CH_2CF_3$ or $CH_2CH_3$, and $R^3$ is H.

In one embodiment, the present invention comprises compounds of Formula I wherein $R^4$ is H and $R^5$ is $CH_3$, $C(CH_3)_3$, $CH(CH_3)_2$, cyclobutyl, cyclopentyl or $CH_2$-cyclopropyl; or $R^4$ and $R^5$ are both $CH_3$; or $R^4$ and $R^5$ together with the N to which they are attached form a pyrrolidine, optionally substituted by hydroxy at the 3-position, or an azetidine. In particular, $R^4$ is H and $R^5$ is $CH_3$, $C(CH_3)_3$, $CH(CH_3)_2$, cyclobutyl, cyclopentyl or $CH_2$-cyclopropyl; or $R^4$ and $R^5$ together with the N to which they are attached form a pyrrolidine or an azetidine. More particularly, $R^4$ and $R^5$ together with the N to which they are attached form a pyrrolidine.

In another embodiment, the present invention comprises compounds of Formula I wherein $R^4$ is H and $R^5$ is $C(CH_3)_3$; or $R^4$ and $R^5$ together with the N to which they are attached form a pyrrolidine or an azetidine. In particular, $R^4$ and $R^5$ together with the N to which they are attached form a pyrrolidine or azetidine.

In a further embodiment, the present invention comprises compounds of Formula I wherein:
A is

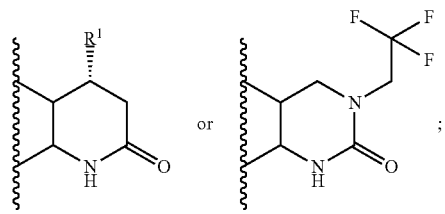

$R^1$ is $CH_3$ or $CF_3$;

$R^2$ is $CF_3$, $CH_2CF_3$, $CH_2CH_2CF_3$, $CH_2CH_3$, $(CH_2)_2CH_3$, $(CH_2)_3CH_3$, $CH(CH_3)_2$, $CH_2CH(CH_3)_2$, $C_3$-$C_6$ cycloalkyl, Cl, Br, $CH$=$CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H; or $R^2$ and $R^3$ are both Cl; and $R^4$ is H and $R^5$ is $CH_3$, $C(CH_3)_3$, $CH(CH_3)_2$, cyclobutyl, cyclopentyl or $CH_2$-cyclopropyl; or $R^4$ and $R^5$ together with the N to which they are attached form a pyrrolidine or an azetidine; or a pharmaceutically acceptable salt thereof.

In yet a further embodiment, the present invention comprises compounds of the formula:

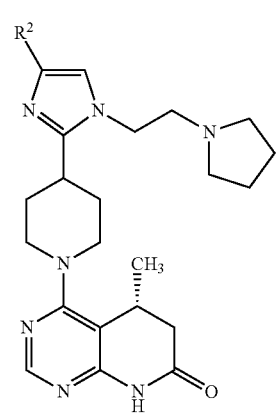

Formula II wherein:
$R^2$ is $CF_3$, $CH_2CF_3$, $CH_2CH_3$ or tetrahydropyran-4-yl; or pharmaceutically acceptable salts thereof.

In another embodiment, the present invention comprises compounds of Formula I
wherein:
A is

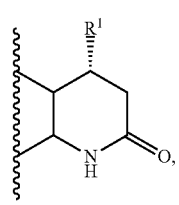

$R^1$ is $CH_3$, $CF_3$ or $CH_2CH_3$;

$R^2$ is $CF_3$, $CH_2CF_3$, $CH_2CH_2CF_3$, $CH_2CH_3$, $(CH_2)_2CH_3$, cyclopropyl, Br, $CH_2CH_2OCH_3$ or tetrahydropyran-4-yl, and $R^3$ is H;

$R^4$ is H and $R^5$ is $C(CH_3)_3$; or $R^4$ and $R^5$ together with the N to which they are attached form a pyrrolidine or an azetidine; or a pharmaceutically acceptable salt thereof.

In yet another embodiment, the present invention comprises compounds of the formula:

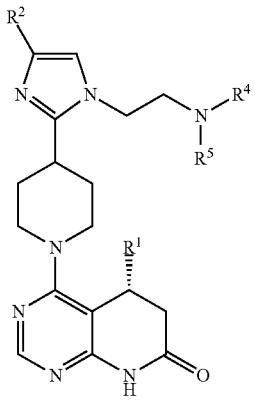

Formula III wherein:
R$^1$ is CH$_3$ or CF$_3$;
R$^2$ is CH$_2$CF$_3$, CH$_2$CH$_2$CF$_3$ or CH$_2$CH$_3$;
R$^4$ and R$^5$ together with the N to which they are attached form a pyrrolidine or an azetidine; or a pharmaceutically acceptable salt thereof.

In another embodiment, there is provided the following compounds, or pharmaceutically acceptable salts thereof:
(R)-5-methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one;
(R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one; and
(R)-4-(4-(1-(2-(azetidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one.

In an embodiment, the compound of the present invention is (R)-5-methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one, or a pharmaceutically acceptable salt thereof. In particular, the compound is (R)-5-methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one. More particularly, the compound is (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one crystalline form III. (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one crystalline form III is characterised by an X-ray powder diffraction pattern (CuKα radiation, λ=1.54056 Å) comprising a peak at 8.53 (2θ±0.1°) and optionally one or more peaks selected from 17.06, 7.97 and 14.17 (2θ±0.1°). Preferably, characterised by an X-ray powder diffraction pattern comprising peaks at 8.53, 17.06, 7.97 and 14.17 (2θ±0.1°).

The compounds of the present invention are inhibitors of AKT and are therefore useful in the treatment of cancer. In particular, the treatment of cancers in which the PI3K/AKT/mTOR pathway is activated, including breast cancer (Carpten et al., 448: 439-444 (2007)), in particular, HER2 positive breast cancer (Yakes et al., Cancer Research, 62: 4132-4141 (2003)); colorectal cancer (Parsons et al., Nature, 436: 792 (2005); Carpten et al., 448: 439-444 (2007)); ovarian cancer (Carpten et al., 448: 439-444 (2007)); lung cancer, in particular, squamous cell lung carcinoma (Malanga et al., Cell Cycle, 7:5: 665-669 (2008)); gastric carcinoma (Byun et al., Int. J. Cancer, 104: 318-327 (2003)); pancreatic cancer (Ruggeri et al., Molecular Carcinogenesis, 21: 81-86 (1998)); head and neck squamous cell carcinoma (Pedrero et al., Int. J. Cancer, 114: 242-248 (2005)); melanoma (Stahl et al., Cancer Research, 64: 7002-7010 (2004)); glioblastoma (The Cancer Genome Atlas Research Network, 455: 1061-1068 (2008)); prostate cancer (Sasaki et al., Biochem. Biophys. Res. Comm., 399(1): 79-83 (2010)); bladder cancer (Ching et al., Lab. Invest., Epub. 26 Jul. 2010); mesothelioma (Mohiuddin et al., Annals of Sur. Oncol., 9(3): 310-316 (2002)); sarcoma, in particular soft tissue sarcoma (Zhu et al., Cancer Res., 68(8): 2895-2903 (2008)); and renal cancer (Hara et al., Annals of Oncol., 16: 928-933 (2005)).

The compounds of the present invention, or pharmaceutically acceptable salts thereof, can be used in a method of treating cancer, in particular, the cancers described above, in a mammal comprising administering to a mammal in need of such treatment an effective amount of a compound of the present invention, or a pharmaceutically acceptable salt thereof. Further provided are the compounds of the present invention, or pharmaceutically acceptable salts thereof, for use in the treatment of cancer, in particular, the cancers described above. Furthermore, the compounds of the present invention, or pharmaceutically acceptable salts thereof, can be used in the manufacture of a medicament for the treatment of cancer, in particular, the cancers described above. There is also provided a pharmaceutical composition for treating cancer, in particular, the cancers described above, comprising a compound of the present invention, or a pharmaceutically acceptable salt thereof.

The compounds of the present invention may be used in combination with other therapeutic agents and in particular, mTOR (mammalian target of rapamycin) inhibitors, EGFR (epidermal growth factor receptor) inhibitors, gemcitabine (Gemzar®), cisplatin, tasisulam (sodium N-[(5-bromothiophen-2-yl)sulfonyl]-2,4-dichlorobenzamide), pemetrexed (Alimta®), docetaxel (Taxotere®), doxorubicin (Doxil®), irinotecan (Campto®; Camptosar®), paclitaxel (Taxol®) or tamoxifen. Preferred mTOR inhibitors include rapamycin (also known as sirolimus) and analogues thereof such as everolimus (42-O-(2-hydroxy)ethyl-rapamycin; disclosed in EP 1 413 581), temsirolimus (42-(3-hydroxy-2-(hydroxymethyl)-2-methyl propanoate)-rapamycin; Torisel®; disclosed in WO 95/28406) and deforolimus (42-(dimethylphosphinate)rapamycin; disclosed in WO 03/64383). Preferred EGFR inhibitors include erlotinib (Tarceva®), cetuximab (Erbitux®; disclosed in EP 0 359 282), panitumumab (Vectibix®; disclosed in EP 0 359 282) and gefinitib (Iressa®; disclosed in EP 0 566 226).

In one embodiment, the present invention provides a product containing a compound of the present invention, or a pharmaceutically acceptable salt thereof, and a therapeutic agent selected from those listed above as a combined preparation for simultaneous, separate or sequential use in therapy. The present invention further provides a compound of the present invention, or a pharmaceutically acceptable salt thereof, for use in simultaneous, separate and sequential combination with a therapeutic agent selected from those listed above in the treatment of breast cancer, colorectal cancer, ovarian cancer, lung cancer, gastric carcinoma, pancreatic cancer, head and neck squamous cell carcinoma, melanoma, glioblastoma, prostate cancer, bladder cancer, mesothelioma, sarcoma and renal cancer. The present invention further provides a method of treating a cancer selected from the group consisting of breast cancer, colorectal cancer, ovarian cancer, lung cancer, gastric carcinoma, pancreatic cancer, head and neck squamous cell carcinoma, melanoma, glioblastoma, prostate cancer, bladder cancer, mesothelioma, sarcoma and renal cancer comprising administering to a patient in need thereof a compound of the present invention, or a pharmaceutically acceptable salt thereof, and a therapeutic agent selected from those listed above in amounts that in combination are effective.

In another embodiment, the present invention provides a pharmaceutical composition comprising a compound of the present invention together with a pharmaceutically acceptable carrier and optionally other therapeutic agents. In particular, a therapeutic agent selected from those listed above.

Oral administration of the compounds of the present invention is preferred. Depending on the circumstances, other routes of administration, for example intravenous, may be used or even preferred. Transdermal administration may be very desirable for patients who are forgetful or petulant about taking oral medicine. Compounds of the present invention may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The compounds of Formula I can be prepared by one of ordinary skill in the art following art recognized techniques and procedures. More specifically, compounds of Formula I can be prepared as set forth in the schemes, preparations, and examples set forth below. It will be recognized by one of skill in the art that the individual steps in the following schemes may be varied to provide the compounds of Formula I. The reagents and starting materials are readily available to one of ordinary skill in the art. All substituents, unless otherwise specified, are as previously defined.

Scheme 1

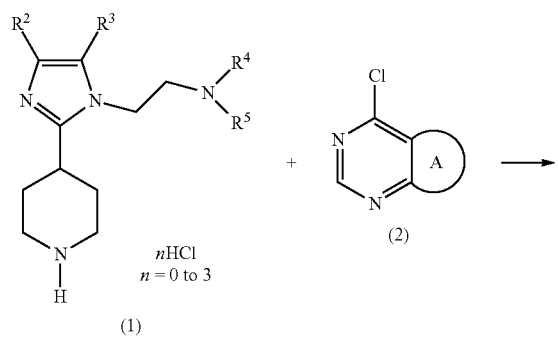

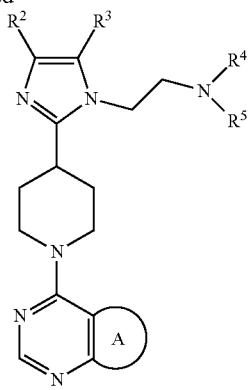

Formula I

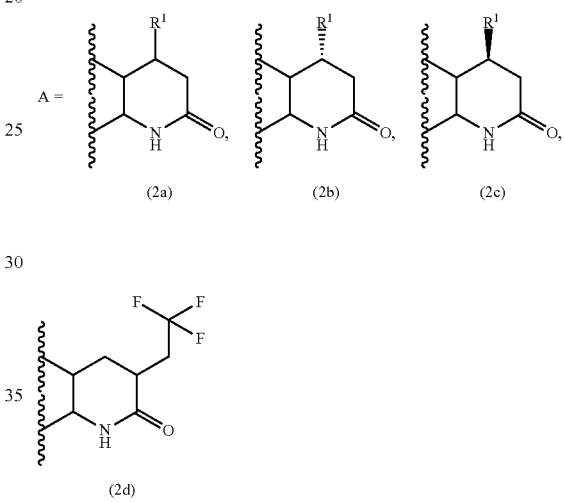

In Scheme 1, a compound of Formula I may be prepared by a nucleophilic substitution reaction between the amine group of the piperidine ring of compound (1) and the leaving group, chloro group of compound (2). Compound (1) and compound (2) are dissolved in suitable solvent such as N-methylpyrrolidinone, methanol or n-propanol with an appropriate base such as diisopropylethylamine, triethylamine or 1,8-diazabicyclo[5.4.0]undec-7-ene. The reaction may be heated in a flask or in a microwave tube. A compound of Formula I may be isolated by methods known in the art such as an aqueous workup which may include an acid wash with aqueous phosphoric acid followed by an aqueous base wash with aqueous sodium hydroxide and further purification such as silica gel chromatography or high pressure liquid chromatography (HPLC-Chiral AD). Alternatively, after the aqueous workup, a compound of Formula I may be isolated by recrystallization from a solvent such as a 75% mixture of methyl tert-butyl ether and hexanes.

A salt of a compound of Formula I may be prepared by dissolving a compound of Formula I in an appropriate aqueous acid such as 4M hydrochloric acid and may be isolated by concentration under reduced pressure. Alternatively, acidic reverse phase chromatography of a compound of Formula I may be used to provide the dihydrochloride or trifluoroacetate salt.

Scheme 2

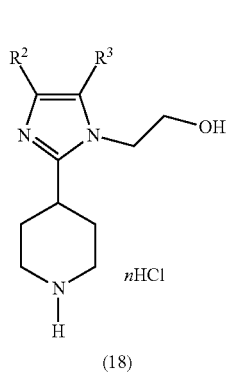

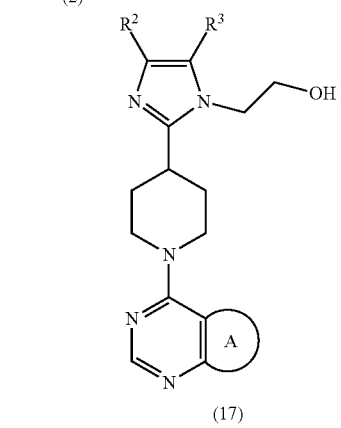

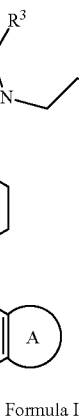

In Scheme 2, an alternative route is described for the preparation of a compound of Formula I (A is defined previously). This synthetic route involves an amine substitution reaction between compound (16) and an appropriate amine to give the —NR⁴R⁵ substituent defined for a compound of Formula I. Compound (16) is dissolved in an appropriate solvent such as dimethylformamide or dimethyl sulfoxide. A suitable base such as triethylamine is added. An appropriate amine that will result in the —NR⁴R⁵ substituent defined for a compound of Formula I is added. The reaction is heated at around 50° C. until completion of the reaction. A compound of Formula I is isolated by traditional means such as an aqueous work-up, concentration, and chromatography of the organic extracts.

Compound (16) is prepared by dissolving compound (17) in an appropriate solvent such as dichloromethane, adding an appropriate base such as triethylamine and cooling to around 0° C. Methanesulfonyl chloride is added dropwise. Afterwards the reaction is quenched with saturated aqueous sodium bicarbonate followed by the traditional methods known in the art to isolate compound (16). Compound (16) may be used without purification to prepare a compound of Formula I. Compound (17) may be prepared from compound (18) (n=1 to 2) and compound (2) by methods described in Scheme 1. Compound (17) may be used without purification to prepare compound (16).

If the resulting compound of Formula I is a racemate, it may be separated into the individual enantiomers by methods known in the art such as chiral chromatography.

The chiral purity of the individual enantiomers of a compound of Formula I can be determined by comparing the two enantiomers by HPLC (Chiralpak AD-H) and superfluid chromatography (Chiral AD-H).

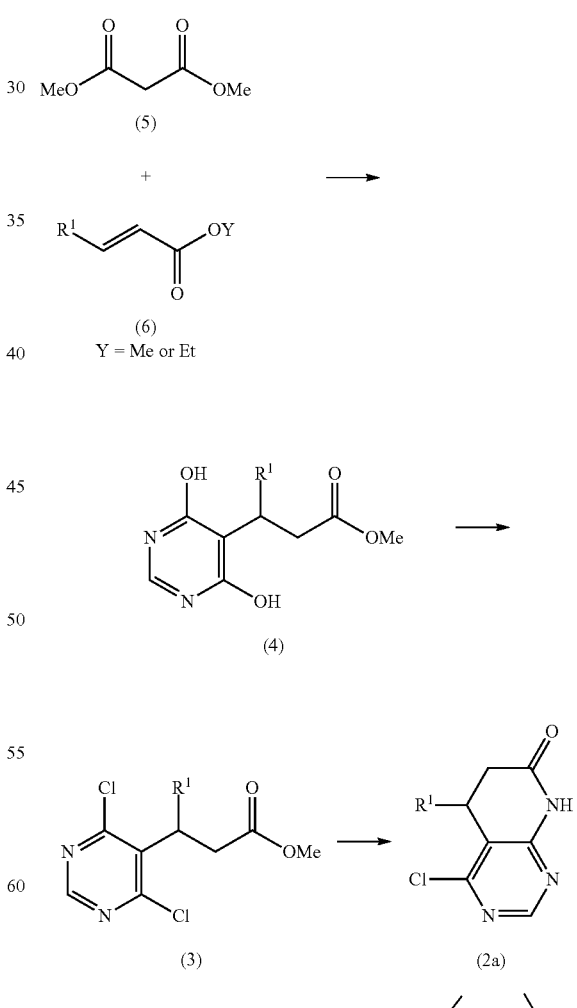

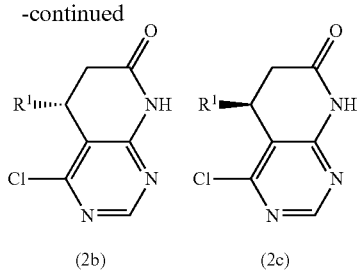

(2b)     (2c)

In Scheme 3, compound (2b) and (2c), enantiomers of the racemic mixture of compound (2a), 4-chloro-5-$R^1$-6,8-dihydro-5H-pyrido[2,3-d]pyrimidin-7-one, may be prepared by a series of reactions beginning with compound (5) and compound (6). Compound (2a) is prepared by combining compound (3) with aqueous ammonium hydroxide (20-30%) or a solution of ammonia gas in isopropanol with heating. Compound (2a) can be isolated by filtration after cooling and a subsequent wash with cold water. Further resolution of compound (2a) by chiral chromatography affords compound (2b) and compound (2c). Compound (2a), (2b) or (2c) may be used by following the synthetic pathway in Scheme 1 or Scheme 2 to form the racemate of a compound of Formula I or the individual enantiomers.

Alternatively, compound (2a) may be protected by a nitrogen protecting group such as a tert-butoxycarbonyl (BOC) moiety using tert-butoxycarbonyl tert-butyl carbonate and 4-(dimethylamino)pyridine in a solvent such as dichloromethane. Subsequent separation of the racemate by chiral chromatography affords the nitrogen BOC-protected compounds (2b) and (2c). Deprotection by methods known in the art such as reacting the BOC-protected compound (2b, 2c) with hydrochloric acid in dioxane affords the desired single enantiomer.

Compound (3) may be prepared by a halogen substitution reaction of compound (4). Compound (3) is dissolved in suitable solvent such as acetonitrile or toluene, in the presence of a base such as N,N-diethylaniline and a chlorinating reagent such as phosphoryl chloride. After refluxing the reaction mixture, compound (3) may be isolated by traditional means such as an aqueous workup with 3M aqueous solution of potassium phosphate dibasic, extraction with an appropriate solvent such as methyl tert-butyl ether, washing of the organic layer with water and concentration in vacuo.

Alternatively, compound (2a) may be synthesized to include a nitrogen protecting group such as a 2,4-dimethoxybenzyl group. Compound (3) is first dissolved in a suitable solvent such as dimethylformamide. A base such as diisopropylethylamine and the reagent 2,4-dimethoxybenzylamine are added. The 2,4-dimethoxybenzyl intermediate is isolated by methods known in the art such as an aqueous work-up. This intermediate is subjected to heating in the presence of a base such as diisopropylethylamine to form a 2,4 dimethoxybenzyl protected compound (3). This compound may be carried on in the synthesis of Scheme 1 to form a 2,4-dimethoxybenzyl protected compound of Formula I. A 2,4-dimethoxybenzyl protected compound of Formula I is deprotected by traditional means to afford the racemate and followed by chiral chromatography to separate the individual enantiomers.

Compound (4) may be prepared by a Michael addition reaction followed by an in situ ring formation reaction. Propanedioic acid dimethyl ester (compound (5)) and compound (6) are added to a mixture of sodium methoxide in methanol solution and formamidine acetate. Compound (4) may be isolated by traditional means by adjusting the pH of the reaction to around 3, filtering, and washing the product with a cooled solvent mixture such as methanol/water.

Scheme 4

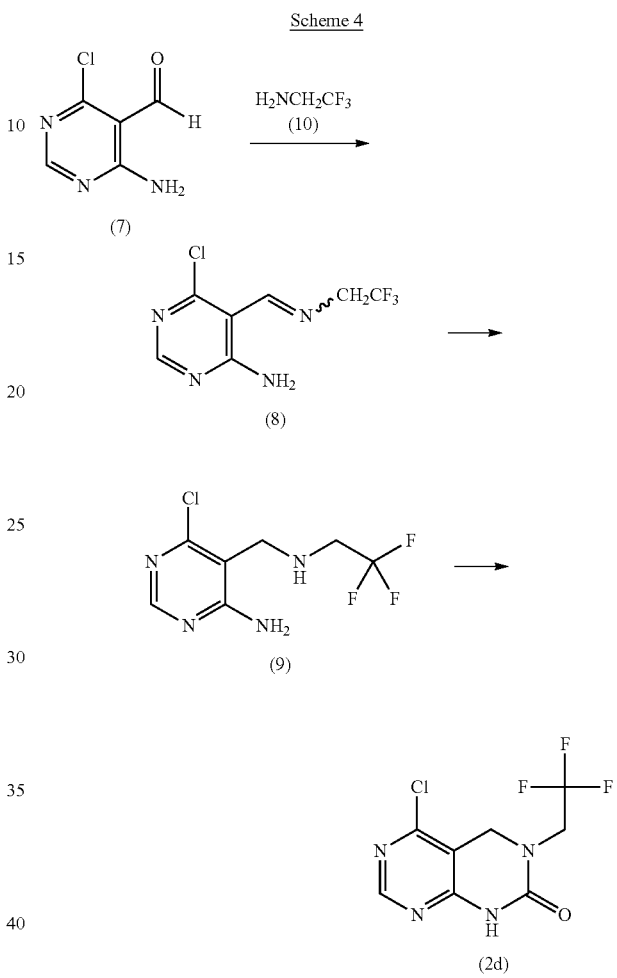

In Scheme 4, compound (2d) may be prepared by a series of reactions beginning with a reductive amination reaction between commercially available starting materials such as the amine (10), 2,2,2-trifluoroethylamine, and a commercially available aldehyde, 4-amino-6-chloropyrimidine-5-carbaldehyde (7), to form the imine (8) in a solvent mixture such as tetrahydrofuran and methanol in the presence of titanium tetraisopropoxide. The imine is reduced by dissolving compound (8) in a solvent such as dichloromethane, cooling under nitrogen, adding methanesulfonic acid and a suitable reducing agent such as borane tert-butylamine. The amine (9) is isolated by a basic aqueous work-up and drying the organics in vacuo. Compound (9) may be used directly in the next reaction without further purification. Compound (2d) is prepared by reacting compound (9) with triphosgene in the presence of a base such as triethylamine in an appropriate solvent such as dichloromethane with cooling to around 0° C. under nitrogen and with subsequent overnight heating of the reaction mixture to around 40° C. Compound (2d) is isolated by methods known in the art such as an aqueous work-up, concentration, and chromatography of the organic extracts. A compound of Formula I can be realized by utilizing compound (2d) as in Scheme 1 and 2.

Scheme 5

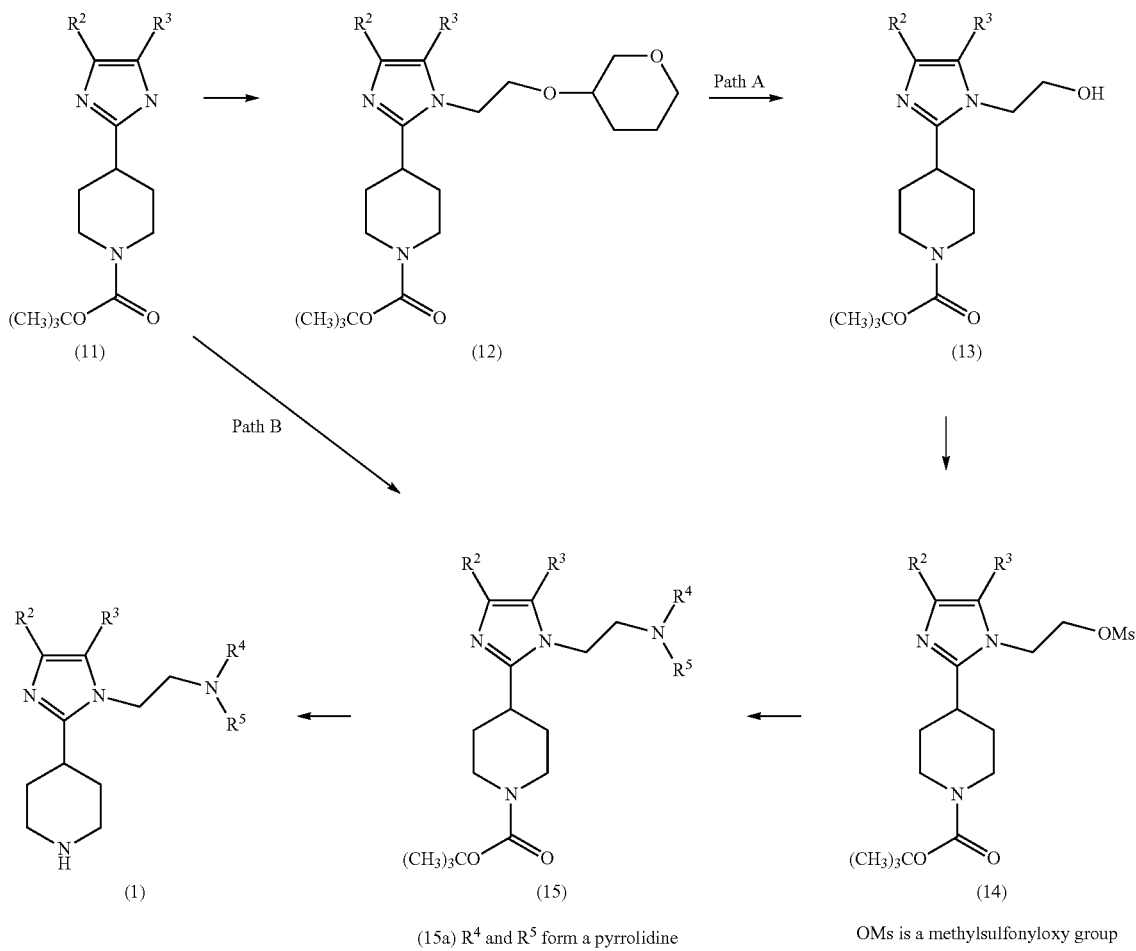

(15a) R⁴ and R⁵ form a pyrrolidine    OMs is a methylsulfonyloxy group

In Scheme 5, compound (1) may be prepared by deprotection of a corresponding tert-butoxycarbonyl compound (15) by traditional means such as adding to compound (15), which is optionally dissolved in a suitable solvent such as dichloromethane, methanol or isopropanol, hydrogen chloride in dioxane, isopropanol, methanol or ethanol. The reaction may be performed at temperatures ranging from room temperature to around 50° C. for about 2 hours to 18 hours. Traditional workup may include evaporating the volatiles followed by an optional basification step with a base such as 2M aqueous sodium hydroxide, extraction with a solvent such as ethyl acetate, and concentration in vacuo to give a compound (1) as the free base, n HCl or n acetate salt.

Compound (15) may be prepared from compound (14) by the same reaction described in Scheme 2 for the preparation of the compound of Formula I from compound (16).

Compound (14) may be prepared from compound (13) by the same reaction described in Scheme 2 for the preparation of compound (16), from compound (17).

Compound (13) may be prepared by an acid catalyzed deprotection reaction from compound (12) according to the synthetic Path A. Compound (12) is dissolved in suitable solvent such as tetrahydrofuran. An acid catalyst such as aqueous 1N hydrochloric acid is added. Compound (13) can be isolated by methods known in the art such as an aqueous workup.

Compound (12) is drawn as one regioisomer but may also represent the mixture of regioisomers. The synthesis and isolation of the regioisomers (12a) and (12b) are shown in Scheme 6. Compound (12) may be prepared by dissolving compound (11) in suitable solvent such as dimethyl sulfoxide with a base such as potassium hydroxide or potassium tert-butoxide. Sodium iodide may be optionally added. 2-(2-Haloethoxy)tetrahydropyran is added to the reaction. The reaction is maintained at room temperature for around 4 hours, or may be heated to around 45° C. to 50° C. for about 1 hour to 12 hours. Compound (12) may be isolated by methods known in the art such as an aqueous workup, concentration in vacuo and purification by chromatography.

Alternatively Path B may be followed to provide compound (1) wherein R⁴ and R⁵ together with the N to which they are attached form a pyrrolidine. Compound (15a) may be prepared by reacting compound (11) with 1-(2-chloroethyl)-pyrrolidine hydrochloride using the reaction conditions described above in relation to the conversion of compound (11) to compound (12). Compound (15a) is drawn as one regioisomer but may also represent the mixture of regioisomers. The synthesis and isolation of the regioisomers (15b) and (15c) are shown in Scheme 6. The BOC protecting group may be removed by traditional means as described above.

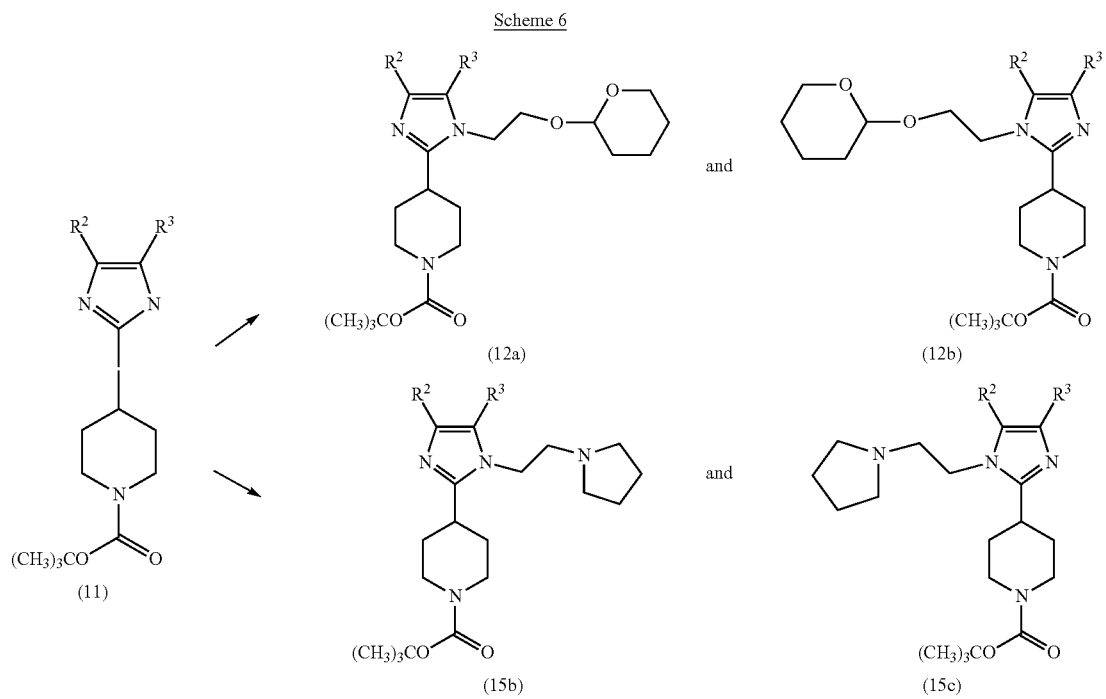

When alkylating compound (11) as in Scheme 5, regioisomers (12a) and (12b) of compound (12) and regioisomers (15b) and (15c) of compound (15a), respectively, may be formed in varying ratios as shown in Scheme 6. In some cases, only the desired isomer (12a) or (15b) is obtained. In other cases, the synthesis results in a ratio which is in favor of the desired compound (12a) or (15b). In this instance, further purification is optional and may occur at a later step to remove the minor impurity. If, however, the ratio between compound (12a) and compound (12b) or compound (15b) and compound (15c) is not as dominant for the desired isomer purification is necessary. Purification to isolate the desired isomer (12a) or (15b) includes column chromatography or recrystallization from an appropriate solvent such as isopropyl alcohol with butanedioic acid, or 1M or 3M hydrochloric acid in methanol or methanol/ethanol mixture with ethyl acetate.

-continued

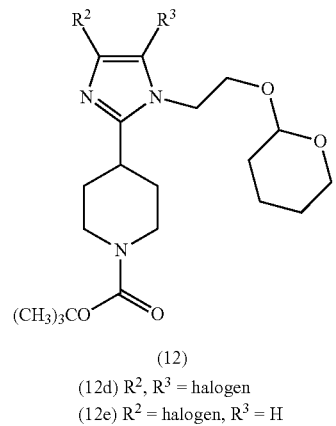

(12)
(12d) $R^2$, $R^3$ = halogen
(12e) $R^2$ = halogen, $R^3$ = H

In Scheme 7, the introduction of $R^2$ and $R^3$ may be achieved by a halogenation substitution reaction between compound (12c) and a halogenating agent such as N-bromosuccinimide to provide a dihalo (12d) or monohalo (12e) substituted compound. Compounds (12d) and (12e) may be carried on in the synthesis such as in Scheme 5. Also compound (12d) when $R^2$ and $R^3$ are bromo may be transformed into compound (12e) by reacting the compound with n-butyllithium at a reduced temperature in an appropriate solvent such as tetrahydrofuran followed by the addition of isopropyl alcohol.

Compound (12e) can be subjected to Suzuki coupling reaction conditions such as palladium acetate, tricyclohexylphosphine, tribasic potassium phosphate N-hydrate and a substituted boronic acid. For example, in the case of cyclopropylboronic acid the bromine will be substituted by cyclopropyl.

Scheme 7

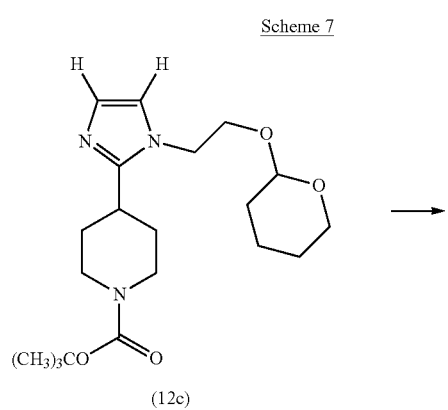

Scheme 8

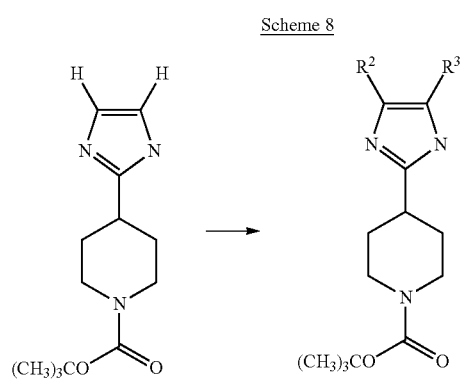

(11a)

(11)
(11b) $R^2 = R^3 = Cl$,
(11c) $R^2 = Cl$ $R^3 = H$
(11d) $R^2 = R^3 = I$

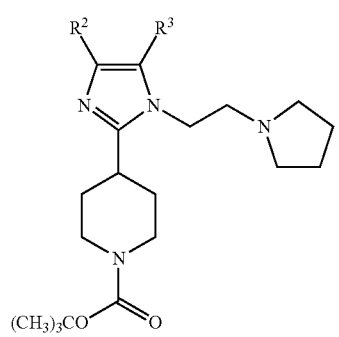

(15a)
(15d) $R^2 = R^3 = Cl$,
(15e) $R^2 = Cl$ $R^3 = H$
(15f) $R^2 = R^3 = I$
(15g) $R^2 = I$ $R^3 = H$

In Scheme 8, the introduction of $R^2$ and $R^3$, when $R^2$ and $R^3$ are chloro or iodo, may be achieved by a halogenation substitution reaction between compound (11a) and a halogenating agent such as N-chlorosuccinimide, N-iodosuccinimide or iodine to provide a dihalo (11b or 11d) or monohalo (11c) substituted compound under reactions conditions commonly found in the literature. Compound (11b) and (11c) may be isolated from the same reaction mixture by column chromatography. Compound (11d) may be isolated by pouring the reaction mixture over a solution of aqueous sodium bisulfate to form a yellow suspension, filtering and washing the solid. Compound (15d, 15e and 15f) may be prepared by following the synthesis found in Scheme 5 from the corresponding compound (11).

Compound (15f) may be mono-dehalogenated in the presence of isopropylmagnesium chloride and 2-methyltetrahydrofuran to form compound (15g). Compound (15g) can be subjected to Suzuki coupling reaction conditions such as palladium acetate, tri-tert-butylphosphonium tetrafluoroborate and a substituted boronate ester such as 2-(3,6 dihydro-2H-pyran-4-yl)-4,4,5,5-tetramethyl-1,3,2-dioxaborolane (compound (38) which may be prepared in accordance with Scheme 16) in an appropriate solvent such as dimethylsulfoxide with a base such as sodium carbonate. The resulting 3,6 dihydro-2H-pyran-4-yl substituted compound may be reduced under an atmosphere of hydrogen in the presence of palladium on charcoal in an appropriate solvent such as ethanol to form compound (15) wherein $R^2$=tetrahydro-2H-pyran-4-yl.

Scheme 9

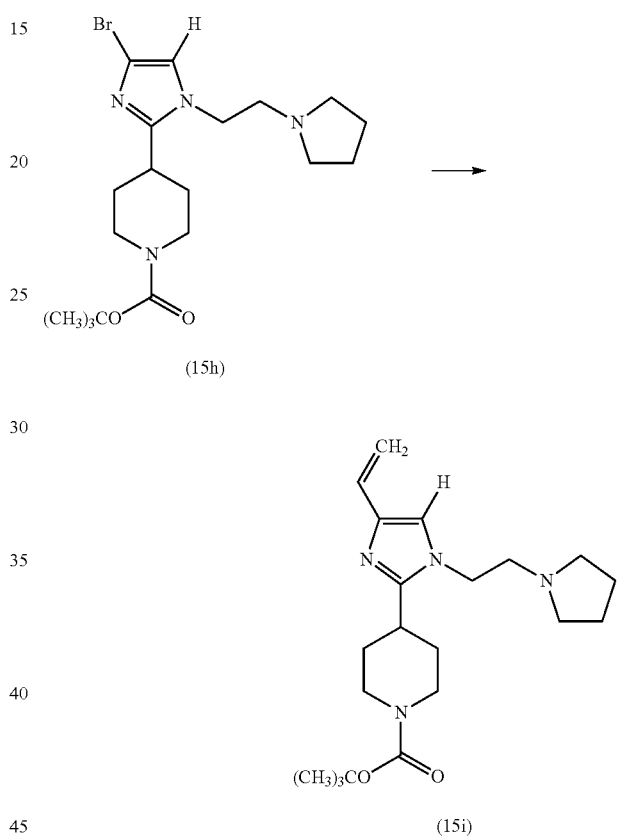

In Scheme 9, compound (15h) may be subjected to Suzuki coupling reaction conditions such as combining with the boronate ester 4,4,5,5-tetramethyl-2-vinyl-1,3,2-dioxaborolane, in the presence of a base, typically tribasic potassium phosphate N-hydrate, and a palladium catalyst typically bis (dibenzylideneacetone)palladium(0) or palladium acetate, and dicyclohexyl-[2-(2,6-dimethoxyphenyl)phenyl]phosphane. The resulting compound (15i) can be carried forward as in Scheme 5 to form compound (1).

Alternatively, this reaction may be performed on the hydroxy-ethyl substituted compound (13) rather than the pyrrolidine-ethyl substituted compound. The resulting alkene compound may be subjected to hydrogenation conditions which include 10% palladium on carbon in an appropriate solvent such as ethanol under a hydrogen atmosphere to form the alkyl substituted compound. The compound may be isolated by filtration through Celite®, a subsequent wash with methanol and concentration in vacuo.

Scheme 10

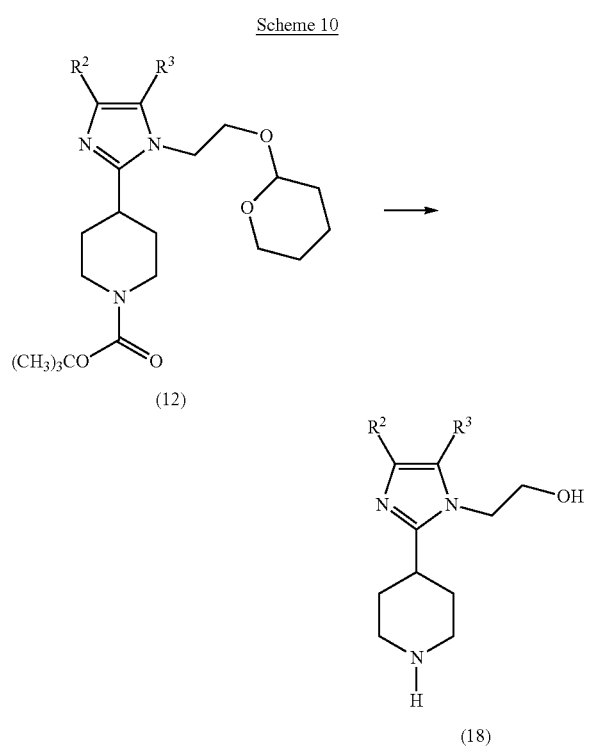

In Scheme 10, compound (18) may be prepared by traditional de-protection methods. Compound (12) is dissolved in a suitable solvent such as methanol, adding 4M hydrochloric acid in a dioxane solution and stirring overnight. Compound (18) can be isolated by methods known in the art such as concentrating in vacuo to give compound (18) as a nHCl salt. Compound (18) may be utilized in Scheme 2 to form a compound of Formula I.

In Scheme 11, compound (11e) may be prepared by a two step process which includes an oxidation reaction of a ketone (22) or aldehyde (26) to compound (23) and a condensation reaction between ammonia, compound (23) and the aldehyde moiety of compound (24). Selenium dioxide is combined in a suitable solvent mixture such as 1,4-dioxane and water with an acid such as acetic acid. The ketone (22) or the aldehyde (26) is added to the oxidizing agent, heated to around 90° C., stirred about 2 to 18 hours, and filtered to obtain the compound (23). An optional work-up might include filtering through Celite®, concentrating in vacuo and dissolving the residue in a solvent such as methanol. Compound (24) is dissolved in methanol with ammonium hydroxide or ammonium acetate and optionally cooled to around 0° C. The compound (23) is added dropwise and the reaction is stirred overnight. Compound (11e) can be isolated by methods known in the art such as filtration, an aqueous work-up and purification by silica gel chromatography. An optional work-up might include diluting the residue with methyl tert-butyl ether and water and adjusting the pH to around 2 by adding aqueous phosphoric acid, separating the aqueous layer, washing the aqueous layer with methyl tert-butyl ether, adjusting the pH to around 10 with sodium carbonate and a final extraction with ethyl acetate. The organic layers are combined, washed with saturated sodium chloride, filtered and concentrated in vacuo to give compound (11e).

Compound (23) may be prepared, if not commercially available, by a series of oxidation reactions starting from compound (25) or (26). 3,3,3-Triacetoxy-3-iodophthalide is dissolved in a suitable solvent such as dichloromethane. Compound (25) is dissolved in the same solvent and added dropwise to the oxidizing reagent. After about 4 hours, compound (26) can be isolated by methods known in the art such as filtration through Celite®, an aqueous workup involving an aqueous wash with sodium thiosulphate and sodium hydroxide, filtration and concentration in vacuo.

Scheme 11

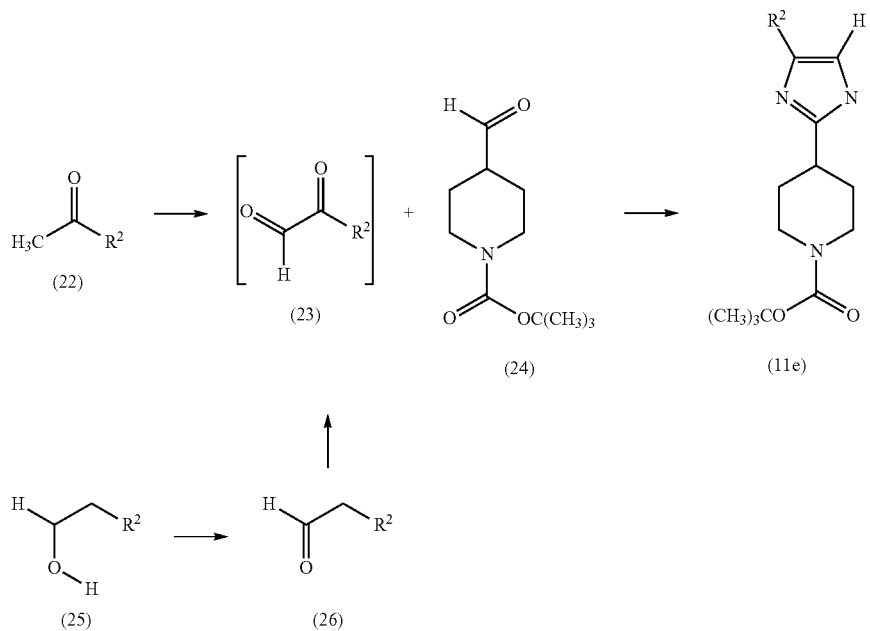

Scheme 12

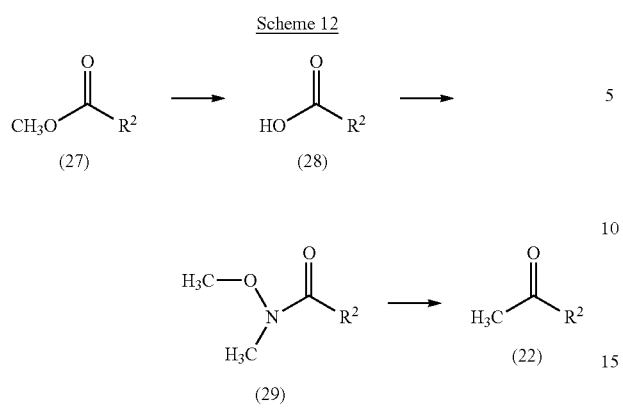

In Scheme 12, compound (22) may be prepared by a Weinreb ketone synthesis which involves forming a Weinreb amide followed by reaction with an organometallic nucleophile and hydrolysis to form the desired ketone. The ester (27) is dissolved in an appropriate solvent such as methanol and a base such as sodium hydroxide is added. The acid (28) may be isolated by traditional means such as an aqueous work-up with methyl tert-butyl ether and an acid wash with aqueous hydrochloric acid. The solid may be carried on in the next reaction without purification. The Weinreb amide (29) is prepared by stirring the acid (28) in an appropriate solvent such as dichloromethane in the presence of 1,1'-carbonyldiimidazole and adding N,O-dimethylhydroxylamine hydrochloride. The Weinreb amide is isolated by an aqueous work-up involving washing with aqueous ammonium chloride and saturated aqueous sodium chloride, and concentration in vacuo. Compound (29) may be used in the next step without further purification. The next step involves dissolving the Weinreb amide in a solvent such as tetrahydrofuran, cooling to around 0° C. and adding the organometallic nucleophile, methyl magnesium chloride. This complex is hydrolyzed by pouring the reaction mixture into an ice/water mixture or aqueous ammonium chloride. An aqueous work-up involving methyl tert-butyl ether and concentration in vacuo provides compound (22). Compound (22) may be utilized in the next step without purification or after purification by silica gel chromatography.

An alternative approach to compound (22) involves reacting compound (27) with isopropylmagnesium chloride and N,—O-dimethylhydroxylamine hydrochloride in a solvent such as tetrahydrofuran at a reduced temperature to form the Weinreb amide.

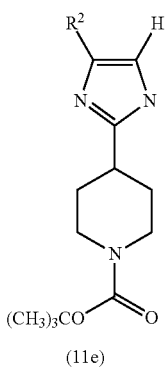

In Scheme 13, compound (11e) may also be prepared by reacting compound (30) with sodium acetate in water at an elevated temperature, then with compound (24) in an appropriate solvent such as methanol and aqueous ammonium hydroxide. Compound (11e) can be isolated by methods known in the art such as an aqueous workup and may be utilized without further purification.

Scheme 14

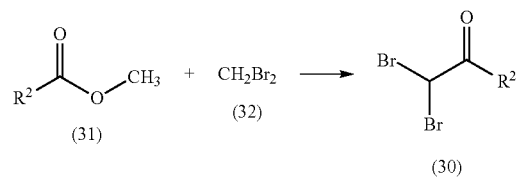

In Scheme 14, the preparation of compound (30) begins with the anion formation of 1,1-dibromomethane (32). The formation of the anion involves the preparation of lithium diisopropylamide from diisopropylamine and n-butyl lithium by methods commonly found in the literature. After formation of lithium diisopropylamide, compound (31) and compound (32) are stirred in an appropriate solvent such as tetrahydrofuran at a reduced temperature and lithium diisopropylamide is added dropwise while maintaining the reduced temperature. The reaction is quenched with aqueous hydrochloride acid followed by an aqueous work-up with solvents such as methyl tert-butyl ether and heptane.

Scheme 13

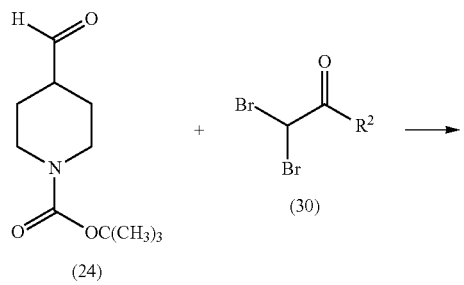

Scheme 15

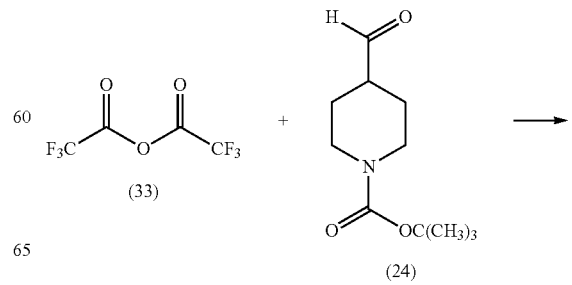

-continued

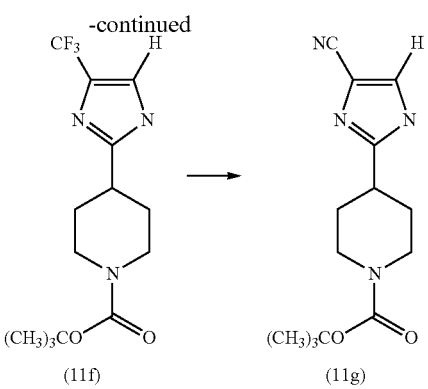

(11f)     (11g)

In Scheme 15, the synthesis of compound (110 is shown as beginning from the anhydride (33). The synthesis is accomplished by forming (E)-(dimethylhydrazono)-1,1,1-trifluoropropan-2-one by reacting N-methyl-N-(methyleneamino)-methanamine with a base such as 2,6-lutidine and adding trifluoroacetic anhydride at a reduced temperature. The intermediate is reacted with compound (24) in acetic acid and ammonium acetate to form compound (11f). Compound (11f) can be further transformed into compound (11g) by transforming the trifluoromethyl substitute into a cyano substitute by heating compound (11f) in ammonium hydroxide, cooling and filtering to isolate the solids.

Scheme 16

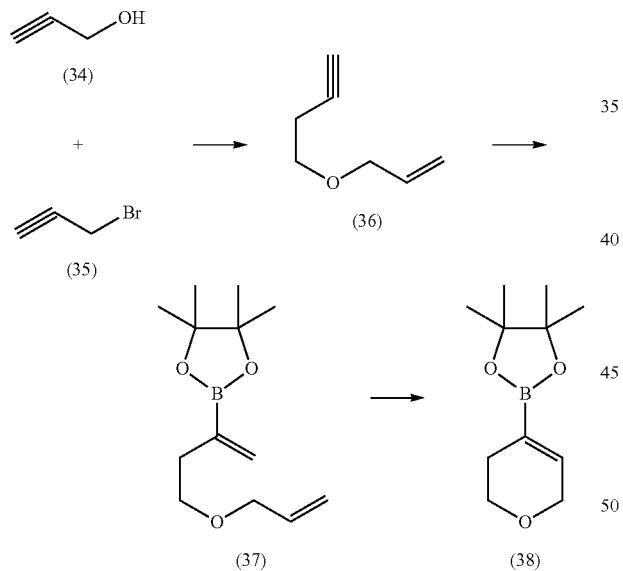

In Scheme 16, compound (38) can be prepared through a series of reactions beginning with a Williamson ether synthesis between compound (34) and (35) in the presence of a base such as sodium hydride and a solvent such as methyl tert-butyl ether to form the ether (36). Compound (36) is subjected to standard reaction conditions to form the boronate ester (37). These reagents may include lithium chloride, cuprous monochloride and bis(pinacolato)diboron and a suitable solvent such as dimethylormamide. Compound (38) may be prepared by a ruthenium catalyzed olefin metathesis utilizing the $2^{nd}$ generation Grubbs' catalyst in an appropriate solvent such as dichloromethane. Compound (38) may be utilized in the synthesis of a compound of Formula I as described in Scheme 8.

The skilled artisan will appreciate that not all of the substituents in the compounds of Formula I will tolerate certain reaction conditions employed to synthesize the compounds. These moieties may be introduced at a convenient point in the synthesis, or may be protected and then de-protected as necessary or desired. The skilled artisan will also appreciate that the protecting groups may be removed at any convenient point in the synthesis of the compounds of the present invention. Methods for introducing and removing nitrogen protecting groups are well known in the art; see, for example, Greene and Wuts, "Protective Groups in Organic Synthesis", $3^{rd}$ Ed., John Wiley and Sons, New York, Chapter 7 (1999). Furthermore, the skilled artisan will appreciate than in many circumstances, the order in which moieties are introduced is not critical. The particular order of steps required to produce the compounds of Formula I is dependent upon the particular compound being synthesized, the starting compound and the relative liability of the substituted intermediates and products.

Preparation 1

(E,Z)-6-Chloro-5-((2,2,2-trifluoroethylamino)methyl)pyrimidin-4-amine

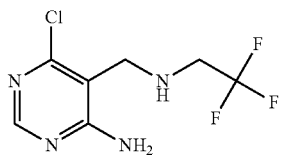 [SMILES: Nc1ncnc(Cl)c1CNCC(F)(F)F]

Add a solution of 4-amino-6-chloropyrimidine-5-carbaldehyde (0.31 g, 1.94 mmol) in tetrahydrofuran (4 mL) to a mixture of titaniumtetra(isopropoxide) (0.85 mL, 1.5 eq), 2,2,2-trifluoroethylamine (0.76 mL, 4.9 eq), and methanol (3.8 mL). Stir the reaction at room temperature overnight. Add 2:1 ammonium hydroxide:water to the reaction mixture, then dilute with ethyl acetate. Separate the layers. Dry the organics over anhydrous sodium sulfate, filter, and concentrate in vacuo to give the title compound as a white solid (0.44 g, 96%). MS (ES) m/z=239 [M]$^+$.

Preparation 2

6-Chloro-5-((2,2,2-trifluoroethylamino)methyl)pyrimidin-4-amine

Combine (E,Z)-6-chloro-5-((2,2,2-trifluoroethylamino)methyl)pyrimidin-4-amine (3.42 g, 14.35 mmol) and dichloromethane (34.8 mL). Cool to 0° C. under nitrogen. Add methanesulfonic acid (2.30 mL, 2.4 eq) dropwise via syringe, maintaining the temperature below 5° C. Add a solution of borane tert-butylamine complex (1.86 g, 1.5 eq) in dichloromethane (10 mL) dropwise via syringe, maintaining the temperature below 5° C. Stir the reaction mixture for 1 hour at 0° C. Add 2:1 ammonium hydroxide:water, then dilute with dichloromethane. Separate the layers. Dry the organics over anhydrous sodium sulfate, filter, and concentrate in vacuo to give the title compound as a yellow solid (2.39 g, 69%). MS (ES) m/z=241 [M]+.

Preparation 3

5-Chloro-3-(2,2,2-trifluoroethyl)-3,4-dihydropyrimido[4,5-d]pyrimidin-2(1H)-one

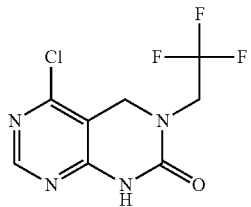 [SMILES: O=C1Nc2ncnc(Cl)c2CN1CC(F)(F)F]

Combine 6-chloro-5-((2,2,2-trifluoroethylamino)methyl) pyrimidin-4-amine (9.57 g, 39.78 mmol), triethylamine (5.50 mL, 2.0 eq), and dichloromethane (795 mL). Cool to 0° C. under nitrogen. Add a solution of triphosgene (11.85 g, 1.0 eq) in dichloromethane (228 mL). Stir at 0° C. for 30 min, and allow to warm to room temperature. Heat the reaction mixture to 40° C. overnight. Add aqueous sodium bicarbonate and extract with ethyl acetate. Dry the organics over anhydrous sodium sulfate, filter, and concentrate in vacuo. Purify by silica gel chromatography, eluting with 9:1 dichloromethane: methanol, to give the title compound (4.50 g, 42%). $^1$H NMR (400 MHz, DMSO-d6) δ 10.83 (s, 1H), 8.41 (s, 1H), 4.20 (m, 2H), 3.25 (s, 2H).

Preparation 4

Methyl 3-(4,6-dihydroxypyrimidin-5-yl)butanoate

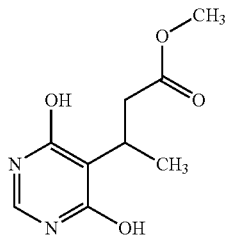

Add sodium methoxide (14.69 g, 0.85 eq) to methanol (70 mL). Heat to reflux over 15 minutes while adding a mixture of propanedioic acid dimethyl ester (36.64 mL, 320.00 mmol) and methyl crotonate (34.01 mL, 1.0 eq). Reflux the mixture for 40 minutes, then allow the mixture to cool to room temperature. Add a mixture of sodium methoxide (19.02 g, 1.1 eq), methanol (70 mL) and formamidine acetate (39.98 g, 1.2 eq). Stir at room temperature overnight. Cool the mixture in an ice bath and add 5 M aqueous hydrochloric acid, adjusting the pH to 3. Filter to give the title compound (41.00 g, 60%). MS (ES) m/z=213 [M]+.

Prepare the following compounds essentially as described for methyl 3-(4,6-dihydroxypyrimidin-5-yl)butanoate:

| Prep | Compound Name | MS (ES) m/z [M]+ |
|---|---|---|
| 5 | methyl 3-(4,6-dihydroxypyrimidin-5-yl) pentanoate | 227 |
| 6 | methyl 3-(4,6-dihydroxypyrimidin-5-yl)-4,4,4-trifluorobutanoate | 267 |

Preparation 7

Methyl 3-(4,6-dichloropyrimidin-5-yl)butanoate

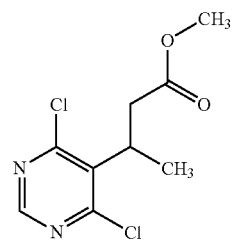

Add methyl 3-(4,6-dihydroxypyrimidin-5-yl)butanoate (41.00 g, 193.21 mmol) to acetonitrile (95 mL). Add phosphoryl chloride (39.50 mL, 2.2 eq) dropwise over ten minutes (exotherm evident). Stir the mixture for ten minutes and add N,N-diethylaniline (34.00 mL, 1.1 eq) dropwise over ten minutes (exotherm evident). Heat the mixture at reflux overnight. Cool the mixture in an ice bath. Add slowly to a pre-cooled mixture of potassium phosphate dibasic aqueous solution (336.52 g in 500 mL water, 10 eq). Extract the aqueous layer with ethyl acetate. Wash the organics with saturated aqueous sodium chloride, dry over anhydrous sodium sulfate, filter, and concentrate in vacuo. Purify by silica gel chromatography, eluting with 10% ethyl acetate in hexanes to 40% ethyl acetate in hexanes, to give the title compound (44.00 g, 55%). MS (ES) m/z=249 [M]+.

Prepare the following compounds essentially as described for methyl 3-(4,6-dichloropyrimidin-5-yl)butanoate:

| Prep | Compound Name | MS (ES) m/z [M]+ |
|---|---|---|
| 8 | methyl 3-(4,6-dichloropyrimidin-5-yl)-4,4,4-trifluorobutanoate | 304 |
| 9 | methyl 3-(4,6-dichloropyrimidin-5-yl) pentanoate | 263 |

Preparation 10

(R)-4-Chloro-5-ethyl-5,6-dihydropyrido[2,3-d]pyrimidin-7(8H)-one

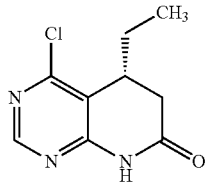

Dissolve methyl 3-(4,6-dichloropyrimidin-5-yl)pentanoate (10.00 g, 38.01 mmol) in 28% ammonium hydroxide in water (95 mL) and seal in a 350 mL tube. Heat the reaction mixture to 200° C. for 2 hours. Cool the reaction mixture in an ice bath, then filter and wash with cold water. Dry the solids under vacuum to give the racemate. Chiral separation (Chiralpak AS-H, 100% ethanol w/0.2% dimethyl ethylamine) provides the title compound as enantiomer 2 (3.19 g, 40%) (>99% ee). MS (ES) m/z=212 [M]$^+$.

Prepare the following compounds essentially as described for (R)-4-chloro-5-ethyl-5,6-dihydropyrido[2,3-d]pyrimidin-7(8H)-one:

| Prep | Compound Name | MS (ES) m/z [M]$^+$ | Chiral separation |
|---|---|---|---|
| 11 | (R)-4-chloro-5-(trifluoromethyl)-5,6-dihydropyrido[2,3-d]pyrimidin-7(8H)-one | 252 | Enantiomer 2 >99% ee 100% ethanol 0.2% DMEA Chrialpak AS-H |

Preparations 12 and 13

4-Chloro-5-methyl-5,6-dihydropyrido[2,3-d]pyrimidin-7(8H)-one and

(R)-4-Chloro-5-methyl-5,6-dihydropyrido[2,3-d]pyrimidin-7(8H)-one

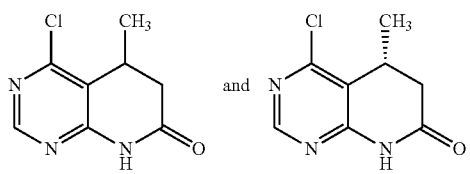

Add methyl 3-(4,6-dichloropyrimidin-5-yl)butanoate (24.00 g, 96.35 mmol) to 30% aqueous ammonium hydroxide (100.00 mL, 7.5 eq) in a sealed tube. Seal and stir the mixture at 60° C. overnight. Cool the mixture in an ice bath. Filter the solid and wash with cold water to give 4-chloro-5-methyl-5,6-dihydropyrido[2,3-d]pyrimidin-7(8H)-one (11.35 g, 60%). MS (ES) m/z=198 [M]$^+$.

Chiral separation (Chiralpak AS, ethanol with 0.2% dimethylethylamine) provides (R)-4-chloro-5-methyl-5,6-dihydropyrido[2,3-d]pyrimidin-7(8H)-one as enantiomer 2 (4.20 g, >99% ee). MS (ES) m/z=198 [M]$^+$.

Preparation 14

4-Chloro-8-(2,4-dimethoxybenzyl)-5-(trifluoromethyl)-5,6-dihydropyrido[2,3-d]pyrimidin-7(8H)-one

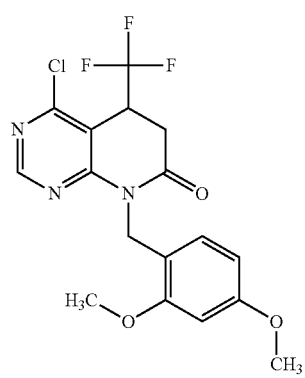 [SMILES: COc1ccc(CN2C(=O)CC(C(F)(F)F)c3c(Cl)ncnc32)c(OC)c1]

Combine methyl 3-(4,6-dichloropyrimidin-5-yl)-4,4,4-trifluorobutanoate (0.71 g, 1.98 mmol) diisopropylethylamine (0.38 mL, 1.1 eq), 2,4-dimethoxybenzylamine (0.32 mL, 1.05 eq), and dimethylformamide (6 mL). Heat at 50° C. overnight. Allow to cool to room temperature. Dilute with water and extract with methyl tert-butyl ether. Wash the organic layer with saturated aqueous sodium chloride. Dry the organics over anhydrous magnesium sulfate, filter, and concentrate in vacuo to give a mixture of the title compound and methyl 3-(4-chloro-6-(2,4-dimethoxybenzylamino)pyrimidin-5-yl)-4,4,4-trifluorobutanoate as an oil. Combine the crude mixture (0.78 g), diisopropylethylamine (0.63 mL), and ethanol (7.8 mL). Heat at reflux for four hours. Allow to cool to room temperature. Filter and rinse with ethanol to obtain the title compound as a white solid (0.43 g, 55%).

Preparation 15

5,5,5-Trifluoropentanal

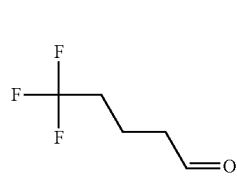

Combine 3,3,3-triacetoxy-3-iodophthalide (17.91 g, 1.2 eq) and dichloromethane (95 mL). Add 5,5,5-trifluoro-1-pentanol (5.00 g, 35.18 mmol) in dichloromethane (238 mL) dropwise under nitrogen. After 4 hours, filter the reaction mixture through Celite®. Concentrate the filtrate in vacuo; combine with 50 mL of dichloromethane and wash with 1:1 10% sodium thiosulphate:aqueous sodium hydroxide (1N). Dry the organics with anhydrous sodium sulfate, filter, and concentrate in vacuo to give the title compound as a colorless oil (2.13 g, 43%). ¹HNMR (400 MHz, DMSO-d6) δ 9.61 (s, 1H), 2.50 (m, 2H), 2.21 (m, 2H), 1.66 (m, 2H).

Preparation 16

5,5,5-Trifluoro-2-oxopentanal

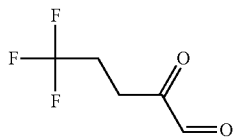

Combine 5,5,5-trifluoropentanal (2.01 g, 14.35 mmol), 1,4-dioxane (10 mL), selenium dioxide (1.62 g, 1.0 eq), water (0.51 mL), and acetic acid (0.69 mL). Heat the mixture at 90° C. and stir overnight. Allow the reaction mixture to cool to room temperature. Filter, wash the solids with dioxane. Combine the filtrate and washings to give the title compound (2.21 g, 100%). GCMS m/z=154.

Prepare the following compounds essentially as described for 5,5,5-trifluoro-2-oxopentanal:

| Prep | Compound Name | MS (ES) m/z [M]⁺ or [M + 18]⁺ |
|---|---|---|
| 17 | 2-cyclobutyl-2-oxoacetaldehyde | 112 |
| 18 | 2-oxopentanal | 119 |
| 19 | 4-methoxy-2-oxobutanal | 117 |
| 20 | 4-methoxy-3,3-dimethyl-2-oxobutanal | 145 |
| 21 | 4-methyl-2-oxopentanal | 115 |

Preparation 22

1-Methylcyclobutanecarboxylic acid

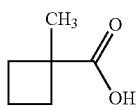

Add 2.5M n-butyllithium in hexanes (281.91 mL, 2.4 eq) to a solution of diisopropylamine (99.70 mL, 2.4 eq) in tetrahydrofuran (900 mL) at 0° C. Stir for 15 minutes, then add a solution of cyclobutanoic acid (28.65 mL, 293.66 mmol) in tetrahydrofuran (100 mL) dropwise, maintaining the temperature below 5° C. Stir the mixture at 5° C. for 5 minutes. Add methyl iodide (18.47 mL, 1.0 eq) dropwise. After 2 days, cool the mixture to 0° C. and acidify with 10% aqueous hydrochloric acid. Extract the aqueous phase with ether. Wash the organics with saturated aqueous sodium chloride, dry over anhydrous sodium sulfate, filter, and concentrate in vacuo to give a yellow oil. Purify by silica gel chromatography, eluting with 5% ethyl acetate in hexanes, to give the title compound as colorless oil (15.77 g, 47%). ¹H NMR (400 MHz, CDCl₃): δ 11.84 (bs, 1H), 2.47 (m, 2H), 1.86 (m, 4H), 1.42 (s, 3H).

Preparation 23

1-(1-Methylcyclobutyl)ethanone

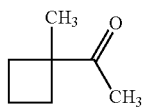

Add 1.6 M methyl lithium in diethyl ether (176.15 mL, 2.0 eq) dropwise to a solution of 1-methylcyclobutanecarboxylic acid (15.77 g, 138.16 mmol) in diethyl ether (500 mL) at 0° C. over 2 hours. Warm the mixture to room temperature and stir for 5 hours. Pour the mixture into ice-cold 3 M aqueous hydrochloric acid. Wash the organics with saturated aqueous sodium bicarbonate, then saturated aqueous sodium chloride. Dry the organics over anhydrous sodium sulfate, filter, and concentrate in vacuo to give the title compound as a colorless oil (11.70 g, 76% yield). ¹H NMR (400 MHz, CDCl₃-d3): δ 2.38 (m, 2H), 1.90 (m, 2H), 1.70 (m, 2H), 1.38 (s, 3H), 1.10 (s, 3H).

Prepare the following compounds essentially as described for 1-(1-methylcyclobutyl)ethanone:

| Prep | Compound Name | ¹H NMR |
|---|---|---|
| 24 | 1-(4-methyltetrahydropyran-4-yl)ethanone | ¹H NMR (400 MHz, DMSO-d6): δ 3.60 (m, 2H), 3.35 (m, 2H), 2.12 (s, 3H), 1.85 (m, 2H), 1.34 (m, 2H), 1.12 (s, 3H) |

Preparation 25

1-(Tetrahydro-pyran-4-yl)-ethanone

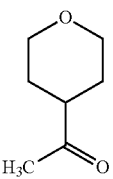

Add butanoic acid, 3-oxo-, methyl ester (18.60 mL, 172.20 mmol), bis(2-chloroethyl)ether (20.20 mL, 1.0 eq), potassium carbonate (52.42 g, 2.2 eq), and sodium iodide (25.88 g, 1.0 eq) in dimethylformamide (861 mL). Heat the reaction mixture at 80° C. overnight. Cool to room temperature. Add additional potassium carbonate (23.78 g) and sodium iodide (25.88 g). Heat the reaction mixture at 80° C. for two hours, then allow the mixture to cool to room temperature. Filter through Celite® and wash with ethyl acetate. Wash the filtrate with water and brine. Dry the organics over anhydrous sodium sulfate, filter, and concentrate in vacuo to give methyl 4-acetyltetrahydro-2H-pyran-4-carboxylate (23.06 g).

Combine methyl 4-acetyltetrahydro-2H-pyran-4-carboxylate (23.06 g, 123.84 mmol) with isopropyl alcohol (124 mL)

and water (124 mL). Add sulfuric acid (33.00 mL, 5.0 eq). Heat the reaction mixture to 100° C. over two nights. Cool and add the reaction mixture slowly to a mixture of sodium bicarbonate (136 g) in water (1 L). Extract with dichloromethane. Dry the organics over anhydrous sodium sulfate, filter, and concentrate in vacuo. Purify by silica gel chromatography, eluting with hexanes to 25% ethyl acetate in hexanes to 50% ethyl acetate in hexanes, to give the title compound (7.39 g, 34%). $^1$H NMR (400 MHz, DMSO-d6) δ 3.79 (m, 2H), 3.27 (m, 2H), 2.54 (m, 1H), 2.05 (s, 3H), 1.66 (m, 2H), 1.38 (m, 2H).

Preparation 26 tert-Butyl 4-(4-(2,2,2-trifluoroethyl)-1H-imidazol-2-yl)piperidine-1-carboxylate

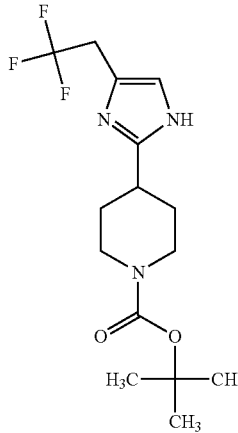

Combine selenium dioxide (10.45 g, 94.15 mmol), 1,4-dioxane (60 mL), acetic acid (5 mL), and water (5 mL). Heat to 80° C. under nitrogen, then slowly add 4,4,4-trifluorobutan-2-one (9.01 mL, 1.0 eq) dropwise. Heat at 90° C. under nitrogen for 12 hours, then let cool to room temperature. Filter the reaction mixture to give an orange-red filtrate. To a separate flask, add tert-butyl 4-formylpiperidine-1-carboxylate (20.08 g, 1.0 eq) in methanol (150 mL) and ammonium hydroxide (117.84 mL, 10.0 eq). Cool to 0° C. under nitrogen. Add the filtrate dropwise via addition funnel Allow to warm to room temperature and stir overnight under nitrogen. Concentrate to dryness in vacuo. Add water and extract with ethyl acetate. Dry the organics over anhydrous magnesium sulfate, filter, and concentrate in vacuo. Purify by silica gel chromatography, eluting with hexanes to 4:1 hexanes:ethyl acetate to 2:1 hexanes:ethyl acetate to 1:1 hexanes:ethyl acetate to 1:2 hexanes:ethyl acetate to ethyl acetate, to give the title compound as a light brown solid (8.06 g, 26%). MS (ES) m/z=334 [M]$^+$.

Prepare the following compounds essentially as described for tert-butyl 4-(4-(2,2,2-trifluoroethyl)-1H-imidazol-2-yl)piperidine-1-carboxylate:

| Prep | Compound Name | MS (ES) m/z [M]$^+$ |
|---|---|---|
| 27 | tert-butyl 4-(4-ethyl-1H-imidazol-2-yl)piperidine-1-carboxylate | 280 |
| 28 | tert-butyl 4-(4-(1-methylcyclobutyl)-1H-imidazol-2-yl)piperidine-1-carboxylate | 320 |
| 29 | tert-butyl 4-(4-(1-methylcyclopropyl)-1H-imidazol-2-yl)piperidine-1-carboxylate | 306 |
| 30 | tert-butyl 4-(4-cyclopentyl-1H-imidazol-2-yl)piperidine-1-carboxylate | 320 |
| 31 | tert-butyl 4-(4-isopropyl-1H-imidazol-2-yl)piperidine-1-carboxylate | 294 |
| 32 | tert-butyl 4-(4-butyl-1H-imidazol-2-yl)piperidine-1-carboxylate | 308 |
| 33 | tert-butyl 4-(4-(4-methyltetrahydro-2H-pyran-4-yl)-1H-imidazol-2-yl)piperidine-1-carboxylate | 350 |
| 34 | tert-butyl 4-(4-cyclohexyl-1H-imidazol-2-yl)piperidine-1-carboxylate | 333 |

Preparation 35 tert-Butyl 4-(4-(tetrahydro-2H-pyran-4-yl)-1H-imidazol-2-yl)piperidine-1-carboxylate

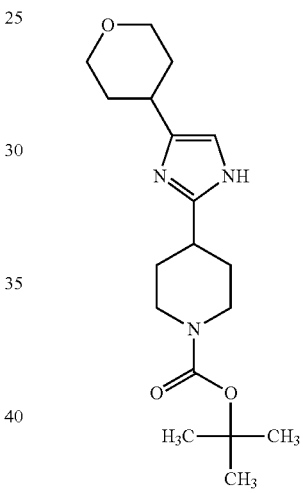

Combine selenium dioxide (5.72 g, 51.54 mmol), 1,4-dioxane (52 mL), acetic acid (2.4 mL, 0.81 eq), water (2.4 mL), and 1-(tetrahydro-pyran-4-yl)-ethanone (6.28 g, 1.0 eq). Stir at 90° C. overnight. Cool and filter, then wash with 1,4-dioxane. Add this filtrate to a solution of tert-butyl 4-formylpiperidine-1-carboxylate (10.47 g, 1.0 eq), methanol (78 mL) and 30% aqueous ammonium hydroxide (30.8 mL) at 0° C. Allow the mixture to warm to room temperature and stir overnight. Concentrate in vacuo and add ethyl acetate and saturated aqueous sodium chloride. Separate the layers. Extract the aqueous layer further with 9:1 dichloromethane:isopropyl alcohol.

Combine selenium dioxide (0.91 g, 8.17 mmol), 1,4-dioxane (8.3 mL), acetic acid (0.4 mL, 0.81 eq), water (0.41 mL), and 1-(tetrahydro-pyran-4-yl)-ethanone (1.00 g, 1.0 eq). Stir at 90° C. overnight. Cool and filter, then wash with 1,4-dioxane. Add this filtrate to a solution of tert-butyl 4-formylpiperidine-1-carboxylate (1.66 g, 1.0 eq), methanol (12.4 mL) and 30% aqueous ammonium hydroxide (4.9 mL) at 0° C. Allow the mixture to warm to room temperature and stir overnight. Concentrate in vacuo and add ethyl acetate and saturated aqueous sodium chloride. Separate the layers. Extract the aqueous layer further with 9:1 dichloromethane:isopropyl alcohol.

Dry the combined organic layers from both reactions over anhydrous sodium sulfate, filter, and concentrate in vacuo. Purify by silica gel chromatography, eluting with hexanes to ethyl acetate to 5% methanol in ethyl acetate to 10% methanol in ethyl acetate, to give the title compound (6.68 g, 35%). MS (ES) m/z=336 [M]⁺.

Preparation 36

N-Methyl-N-(methyleneamino)methanamine

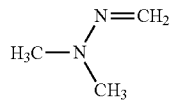

Combine dimethyl hydrazine (10.63 mL, 139.77 mmol) and paraformaldehyde (4.20 g, 0.33 eq). Stir the reaction for 1 hour. Add heptane (20 mL) and sodium sulfate (20 g). Stir 5 minutes, then filter off the sodium sulfate. Distill the filtrate with a short path distillation apparatus, collecting the title compound as a 75% w/w solution with heptane (10.3 g, 77%). ¹H NMR (400 MHz, CDCl₃) δ 6.10 (m, 2H), 2.80 (s, 6H).

Preparation 37 tert-Butyl 4-(4-(trifluoromethyl)-1H-imidazol-2-yl)piperidine-1-carboxylate

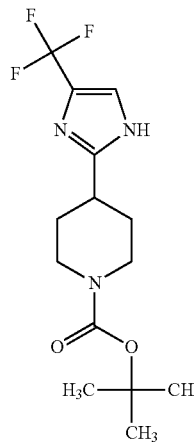

Add N-methyl-N-(methyleneamino)methanamine (1.30 g, 18.03 mmol) into chloroform (100 mL), then add 2,6-lutidine (3.2 mL, 1.5 eq). Cool the reaction mixture to 0° C. and add trifluoroacetic anhydride (3.9 mL, 1.5 eq) over one minute. Allow the reaction to stir at 0° C. for 10 minutes. Wash sequentially with 0.5 M aqueous HCl, water, and 0.1 M aqueous sodium carbonate. Dry the organics over anhydrous sodium sulfate, filter, and concentrate in vacuo to afford crude (E)-3-(dimethylhydrazono)-1,1,1-trifluoro-propan-2-one (1.80 g).

Add a portion of the intermediate (0.21 g, 1.25 mmol) and tert-butyl 4-formylpiperidine-1-carboxylate (0.33 g, 1.24 eq) in acetic acid (8 mL) and ammonium acetate (3.0 g). Heat at 80° C. for 12 hours, then allow the mixture to cool to room temperature. Dilute with dichloromethane and saturated aqueous sodium bicarbonate. Stir for ten minutes, then extract twice with dichloromethane. Concentrate the organics in vacuo and purify by silica gel chromatography to give the title compound (0.19 g, 28%). ¹H NMR (400 MHz, CD₃OD) δ 7.40 (s, 1H), 4.15 (m, 2H), 2.90 (m, 3H), 1.90 (m, 2H), 1.65 (m, 2H), 1.40 (s, 9H).

Preparation 37 (Alternate)

tert-Butyl 4-(4-(trifluoromethyl)-1H-imidazol-2-yl)piperidine-1-carboxylate

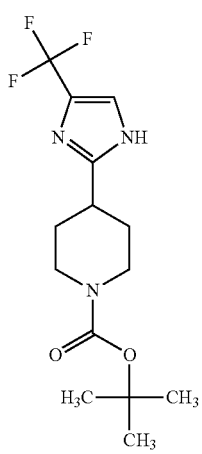 [SMILES: CC(C)(C)OC(=O)N1CCC(c2nc(C(F)(F)F)c[nH]2)CC1]

Add sodium acetate (360.8 g, 2.0 eq) to water (3.54 L) at 30° C. Add 1,1-dibromo-3,3,3-trifluoroacetone (653.01 g, 1.10 mol) dropwise. Heat the mixture at 90° C. under nitrogen for 1 hour. Add tert-butyl 4-formylpiperidine-1-carboxylate (470.00 g, 2.0 eq) to methanol (10 L) in another flask at 30° C. Add a solution of 28% aqueous ammonium hydroxide (2.53 L, 8.18 eq) into the methanol solution. Cool the first mixture to 30° C. and add dropwise to the methanol solution over 45 minutes. Stir overnight under nitrogen. Remove solvent from the reaction mixture. Add water (2 L) and dichloromethane (6 L) and stir for 15 minutes at 25° C. Extract the aqueous layer with dichloromethane three times (1 L ×3). Wash the organics with saturated aqueous sodium chloride solution. Dry over anhydrous sodium sulfate and concentrate in vacuo. Add 5 L solution of 2% ethyl acetate in hexanes and stir at 30° C. for 30 minutes. Filter the solid, wash with hexanes, and concentrate in vacuo to give the title compound as a white solid (618.0 g, 88%). ¹H NMR (400 MHz, CDCl₃) δ 10.5 (s, 1H), 7.4 (s, 1H), 4.18 (s, 2H), 2.98 (m, 1H), 2.80 (m, 2H), 2.01 (m, 2H), 1.71 (m, 2H), 1.45 (s, 9H).

Prepare the following compound essentially as described for tert-butyl 4-(4-(trifluoromethyl)-1H-imidazol-2-yl)piperidine-1-carboxylate:

| Prep | Compound Name | MS (ES) m/z [M]⁺ |
|---|---|---|
| 38 | tert-butyl 4-(4-tert-butyl-1H-imidazol-2-yl)piperidine-1-carboxylate | 308 |

Preparation 39 tert-Butyl 4-(4-cyano-1H-imidazol-2-yl)piperidine-1-carboxylate

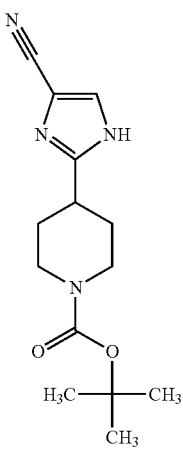 [SMILES: CC(C)(C)OC(=O)N1CCC(c2nc(C#N)c[nH]2)CC1]

Combine tert-butyl 4-(4-(trifluoromethyl)-1H-imidazol-2-yl)piperidine-1-carboxylate (1.50 g, 4.70 mmol) and ammonium hydroxide (90 mL). Heat the reaction mixture at 60° C. for two days. Let cool to room temperature, then filter via Buchner funnel Wash the solids with water and hexanes to give the title compound as a white solid (1.08 g, 83%). MS (ES) m/z=221 [M]+.

Preparation 40 tert-Butyl 4-(1H-imidazol-2-yl)piperidine-1-carboxylate

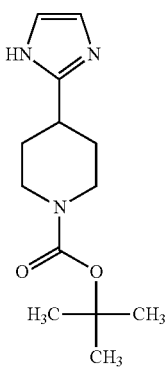 [SMILES: CC(C)(C)OC(=O)N1CCC(c2ncc[nH]2)CC1]

Combine ammonium hydroxide (150 mL), tert-butyl 4-formylpiperidine-1-carboxylate (29.82 g, 139.81 mmol), and methanol (600 mL). Add ethanedial (16.10 mL, 1.0 eq) (40% in water) under nitrogen. Stir overnight. Then concentrate in vacuo to remove methanol. Dilute with water, then extract with dichloromethane. Wash the organics with saturated aqueous sodium chloride. Dry the organics over magnesium sulfate, filter, and concentrate in vacuo to give the title compound (33.30 g, 95%). MS (ES) m/z=252 [M]+.

Prepare the following compounds essentially as described for tert-butyl 4-(1H-imidazol-2-yl)piperidine-1-carboxylate:

| Prep | Compound Name | MS (ES) m/z [M]+ |
|---|---|---|
| 41 | tert-butyl 4-(4-(3,3,3-trifluoropropyl)-1H-imidazol-2-yl)piperidine-1-carboxylate | 348 |
| 42 | tert-butyl 4-(4-cyclobutyl-1H-imidazol-2-yl)piperidine-1-carboxylate | 306 |
| 43 | tert-butyl 4-(4-methyl-1H-imidazol-2-yl)piperidine-1-carboxylate | 266 |
| 44 | tert-butyl 4-(4-propyl-1H-imidazol-2-yl)piperidine-1-carboxylate | 294 |
| 45 | tert-butyl 4-(4-(2-methoxyethyl)-1H-imidazol-2-yl)piperidine-1-carboxylate | 310 |
| 46 | tert-butyl 4-(4-(1-methoxy-2-methylpropan-2-yl)-2-1H-imidazol-yl) piperidine-1-carboxylate | 338 |
| 47 | tert-butyl 4-(4-isobutyl-1H-imidazol-2-yl)piperidine-1-carboxylate | 308 |

Preparations 48 and 49 tert-Butyl 4-(4,5-dichloro-1H-imidazol-2-yl)piperidine-1-carboxylate and tert-Butyl 4-(4-chloro-1H-imidazol-2-yl)piperidine-1-carboxylate

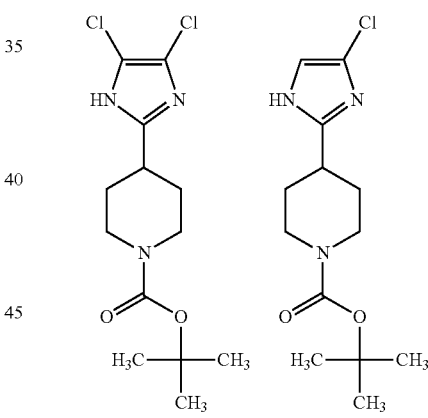

Add tert-butyl 4-(1H-imidazol-2-yl)piperidine-1-carboxylate (6.00 g, 23.87 mmol) in dichloroethane (200 mL). Add N-chlorosuccinimide (3.19 g, 1.0 eq). Stir at room temperature under nitrogen for 14 hours. Concentrate the reaction mixture in vacuo. Purify by silica gel chromatography, eluting with hexanes to 9:1 hexanes:ethyl acetate to 4:1 hexanes:ethyl acetate to 2:1 hexanes:ethyl acetate to 1:1 hexanes:ethyl acetate, to give two major spots. Concentrate fractions containing the higher Rf spot in vacuo to give tert-butyl 4-(4,5-dichloro-1H-imidazol-2-yl)piperidine-1-carboxylate (2.25 g, 29%). MS (ES) m/z=321 [M]+. Concentrate fractions containing the lower spot in vacuo. Slurry the resulting solid into diethyl ether/chloroform, then filter. Concentrate the filtrate in vacuo to give tert-butyl 4-(4-chloro-1H-imidazol-2-yl)piperidine-1-carboxylate (1.16 g, 17%). MS (ES) m/z=286 [M]+.

Preparation 50 tert-Butyl 4-(4-isobutyl-1-(2-(pyrrolidin-1-yl)ethyl)-1H-imidazol-2-yl)piperidine-1-carboxylate

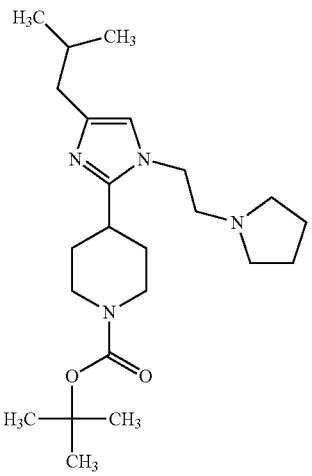 [SMILES: CC(C)Cc1cn(CCN2CCCC2)c(C2CCN(C(=O)OC(C)(C)C)CC2)n1]

Combine tert-butyl 4-(4-isobutyl-1H-imidazol-2-yl)piperidine-1-carboxylate (1.50 g, 4.88 mmol) and potassium hydroxide (1.65 g, 6.0 eq) (freshly powdered) in dimethyl sulfoxide (30 mL). Heat the reaction mixture to 45° C. under nitrogen. After 5 minutes, add 1-(2-chloroethyl)pyrrolidine hydrochloride (1.08 g, 1.3 eq). Stop heating after 2 hours. Add water and extract with ethyl acetate. Dry the organics over anhydrous magnesium sulfate, filter, and concentrate in vacuo to give the title compound as a yellow oil (2.11 g, 100%). MS (ES) m/z=405 [M]+.

Prepare the following compounds essentially as described for tert-butyl 4-(4-isobutyl-1-(2-(pyrrolidin-1-yl)ethyl)-1H-imidazol-2-yl)piperidine-1-carboxylate (Note 1: A mix of 4- and 5-substituted alkylation isomers may be obtained. In some cases, purification by normal phase chromatography can afford the desired isomer. Note 2: Use of the reagents 2-(2-bromoethoxy)tetrahydro-2H-pyran or 2-(2-chloroethoxy)tetrahydro-2H-pyran can afford the 2-(tetrahydro-2H-pyran-2-yloxy)ethyl compounds):

| Prep | Compound Name | MS (ES) m/z [M]+ |
|---|---|---|
| 51 | tert-butyl 4-(1-(2-(pyrrolidin-1-yl)ethyl)-4-(3,3,3-trifluoropropyl)-1H-imidazol-2-yl)piperidine-1-carboxylate | 445 |
| 52 | tert-butyl 4-(4-(1-methylcyclobutyl)-1-(2-(pyrrolidin-1-yl)ethyl)-1H-imidazol-2-yl)piperidine-1-carboxylate | 417 |
| 53 | tert-butyl 4-(4-cyclobutyl-1-(2-(pyrrolidin-1-yl)ethyl)-1H-imidazol-2-yl)piperidine-1-carboxylate | 403 |
| 54 | tert-butyl 4-(1-(2-(pyrrolidin-1-yl)ethyl)-1H-imidazol-2-yl)piperidine-1-carboxylate | 349 |
| 55 | tert-butyl 4-(4-(1-methylcyclopropyl)-1-(2-(pyrrolidin-1-yl)ethyl)-1H-imidazol-2-yl)piperidine-1-carboxylate | 403 |
| 56 | tert-butyl 4-(4-cyclopentyl-1-(2-(pyrrolidin-1-yl)ethyl)-1H-imidazol-2-yl)piperidine-1-carboxylate | 417 |
| 57 | tert-butyl 4-(4-cyclohexyl-1-(2-(pyrrolidin-1-yl)ethyl)-1H-imidazol-2-yl)piperidine-1-carboxylate | 431 |
| 58 | tert-butyl 4-(1-(2-(pyrrolidin-1-yl)ethyl)-4-(2,2,2-trifluoroethyl)-1H-imidazol-2-yl)piperidine-1-carboxylate | 431 |
| 59 | tert-butyl 4-(4-cyano-1-(2-(pyrrolidin-1-yl)ethyl)-1H-imidazol-2-yl)piperidine-1-carboxylate | 374 |
| 60 | tert-butyl 4-(4-tert-butyl-1-(2-(pyrrolidin-1-yl)ethyl)-1H-imidazol-2-yl)piperidine-1-carboxylate | 405 |
| 61 | tert-butyl 4-(4,5-dichloro-1-(2-(pyrrolidin-1-yl)ethyl)-1H-imidazol-2-yl)piperidine-1-carboxylate | 417 |
| 62 | tert-butyl 4-(4-ethyl-1-(2-(tetrahydro-2H-pyran-2-yloxy)ethyl)-1H-imidazol-2-yl)piperidine-1-carboxylate | 408 |
| 63 | tert-butyl 4-(4-propyl-1-(2-(tetrahydro-2H-pyran-2-yloxy)ethyl)-1H-imidazol-2-yl)piperidine-1-carboxylate | 422 |
| 64 | tert-butyl 4-(1-(2-(tetrahydro-2H-pyran-2-yloxy)ethyl)-1H-imidazol-2-yl)piperidine-1-carboxylate | 477 |
| 65 | tert-butyl 4-(1-(2-(tetrahydro-2H-pyran-2-yloxy)ethyl)-4-(tetrahydro-2H-pyran-4-yl)-1H-imidazol-2-yl)piperidine-1-carboxylate | 464 |
| 66 | tert-butyl 4-(1-(2-(tetrahydro-2H-pyran-2-yloxy)ethyl)-4-(trifluoromethyl)-1H-imidazol-2-yl)piperidine-1-carboxylate | 448 |
| 67 | tert-butyl 4-(4-methyl-1-(2-(tetrahydro-2H-pyran-2-yloxy)ethyl)-1H-imidazol-2-yl)piperidine-1-carboxylate | 394 |
| 68 | tert-butyl 4-(4-isopropyl-1-(2-(tetrahydro-2H-pyran-2-yloxy) ethyl)-1H-imidazol-2-yl) piperidine-1-carboxylate | 422 |
| 69 | tert-butyl 4-(4-(2-methoxyethyl)-1-(2-(tetrahydro-2H-pyran-2-yloxy) ethyl)-1H-imidazol-2-yl) piperidine-1-carboxylate | 438 |
| 70 | tert-butyl 4-(4-cyclopentyl-1-(2-(tetrahydro-2H-pyran-2-yloxy)-ethyl)-1H-imidazol-2-yl) piperidine-1-carboxylate | 448 |

-continued

| Prep | Compound Name | MS (ES) m/z [M]+ |
|------|---------------|------------------|
| 71 | tert-butyl 4-(1-(2-(tetrahydro-2H-pyran-2-yloxy) ethyl)-4-(2,2,2-trifluoroethyl)-1H-imidazol-2-yl) piperidine-1-carboxylate | 462 |
| 72 | tert-butyl 4-(4-(1-methoxy-2-methylpropan-2-yl)-1-(2-(tetrahydro-2H-pyran-2-yloxy)ethyl)-1H-imidazol-2-yl)piperidine-1-carboxylate | 466 |
| 73 | tert-butyl 4-(4-chloro-1-(2-(pyrrolidin-1-yl)ethyl)-1H-imidazol-2-yl)piperidine-1-carboxylate | 383 |
| 74 | tert-butyl 4-(4-butyl-1-(2-(pyrrolidin-1-yl)ethyl)-1H-imidazol-2-yl)piperidine-1-carboxylate | 405 |
| 75 | tert-butyl 4-(4-butyl-1-(2-(tetrahydro-2H-pyran-2-yloxy) ethyl)-1H-imidazol-2-yl) piperidine-1-carboxylate | 436 |
| 76 | tert-butyl 4-(4-(4-methyltetrahydro-2H-pyran-4-yl)-1-(2-(tetrahydro-2H-pyran-2-yloxy) ethyl)-1H-imidazol-2-yl)-piperidine-1-carboxylate | 478 |
| 77 | tert-butyl 4-(1-(2-(pyrrolidin-1-yl)ethyl)-4-(trifluoromethyl)-1H-imidazol-2-yl)piperidine-1-carboxylate | 417 |

Preparation 78 tert-Butyl 4-(1-(2-(tetrahydro-2H-pyran-2-yloxy) ethyl)-4-(tetrahydro-2H-pyran-4-yl)-1H-imidazol-2-yl)piperidine-1-carboxylate

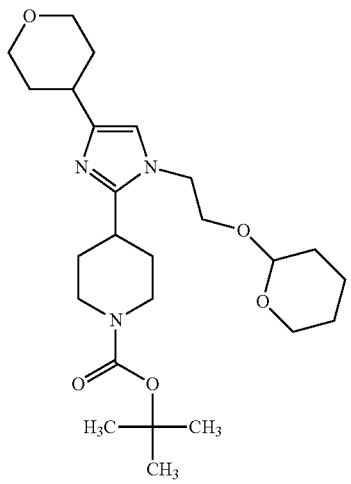 [SMILES: CC(C)(C)OC(=O)N1CCC(c2nc(C3CCOCC3)cn2CCOC2CCCCO2)CC1]

Combine tert-butyl 4-(4-(tetrahydro-2H-pyran-4-yl)-1H-imidazol-2-yl)piperidine-1-carboxylate (5.84 g, 17.40 mmol) and potassium hydroxide (5.91 g, 6.0 eq) (freshly powdered) in dimethyl sulfoxide (30 mL). Heat the reaction mixture to 45° C. under nitrogen. After 15 minutes, add 2-(2-bromoethoxy)tetrahydro-2H-pyran (2.90 mL, 1.1 eq). Continue to heat the reaction overnight. Add water and extract with ethyl acetate. Wash the organics with saturated aqueous sodium chloride. Dry the organics over anhydrous magnesium sulfate, filter, and concentrate in vacuo. Purify by silica gel chromatography, eluting with hexanes to 50% ethyl acetate in hexanes to ethyl acetate to 10% methanol in ethyl acetate, to give the title compound as a thick yellow oil (6.94 g, 86%). MS (ES) m/z=464 [M]+.

Preparation 79 tert-Butyl 4-(4-(trifluoromethyl)-1-(2-pyrrolidin-1-ylethyl)-1H-imidazol-2-yl)piperidine-1-carboxylate succinate

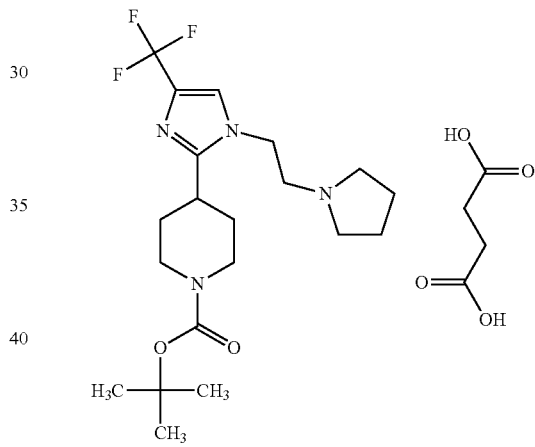

Add 1-(2-chloro-ethyl)-pyrrolidinium chloride (73.50 g, 1.15 eq) to a mixture of tert-butyl 4-(4-(trifluoromethyl)-1H-imidazol-2-yl)piperidine-1-carboxylate (120.00 g, 375.79 mmol) and potassium hydroxide (54.82 g, 2.60 eq) in dimethyl sulfoxide (1.1 L). Stir the resulting suspension at 50° C. overnight. Cool the reaction mixture to room temperature and add ice/water (1.50 l). Extract with ethyl acetate (3×500 mL). Wash the organics with water (2×300 mL) and saturated aqueous sodium chloride (300 mL), dry over anhydrous sodium sulfate. Purify by silica gel chromatography, eluting with 5% to 15% isopropyl alcohol in dichloromethane, to give a mixture of tert-butyl 4-(4-(trifluoromethyl)-1-(2-pyrrolidin-1-ylethyl)-1H-imidazol-2-yl)piperidine-1-carboxylate (122.00 g, 78%) and tert-butyl 4-(5-(trifluoromethyl)-1-(2-pyrrolidin-1-ylethyl)-1H-imidazol-2-yl)piperidine-1-carboxylate (14.00 g, 9%). Add isopropyl alcohol (470 mL) and heat to 70° C. Add a solution of butanedioic acid (35 g, 1 eq) in isopropyl alcohol (350 mL) preheated at 75° C. Stop heating and let stir at room temperature overnight. Filter the solid and wash with isopropyl alcohol (300 mL). Suspend the solid in isopropyl alcohol (500 mL) and stir 15 minutes. Filter and stir the solid in isopropyl alcohol (500 mL) 15 minutes one more time, then filter to give the title compound (124.00 g, 82%) as a white solid. MS (ES) m/z=417 [M]+.

Preparation 80 tert-Butyl 4-(4,5-dibromo-1-(2-(tetrahydro-2H-pyran-2-yloxy)ethyl)-1H-imidazol-2-yl)piperidine-1-carboxylate

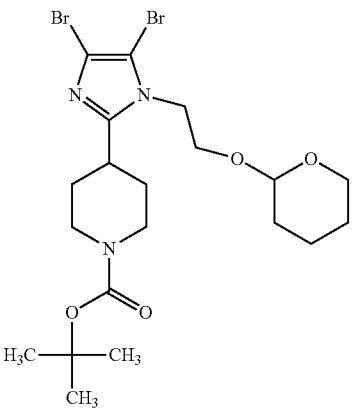 [SMILES: CC(C)(C)OC(=O)N1CCC(c2nc(Br)c(Br)n2CCOC2CCCCO2)CC1]

Add tert-butyl 4-(1-(2-(tetrahydro-2H-pyran-2-yloxy)ethyl)-1H-imidazol-2-yl)piperidine-1-carboxylate (121.70 g, 320.69 mmol) in dichloromethane (1750 mL). Add N-bromosuccinimide (114.15 g, 2.0 eq). Stir at room temperature under nitrogen. Stop the reaction after 90 minutes. Dilute the reaction mixture with water and extract with dichloromethane. Dry the organics over anhydrous magnesium sulfate, filter, and concentrate in vacuo. Purify by silica gel chromatography, eluting with hexanes to 1:1 hexanes:ethyl acetate to ethyl acetate, to give the title compound as a light-orange sticky oil (125.40 g, 73%). MS (ES) m/z=538 [M]+.

Preparation 81 tert-Butyl 4-(4-bromo-1-(2-(tetrahydro-2H-pyran-2-yloxy)ethyl)-1H-imidazol-2-yl)piperidine-1-carboxylate

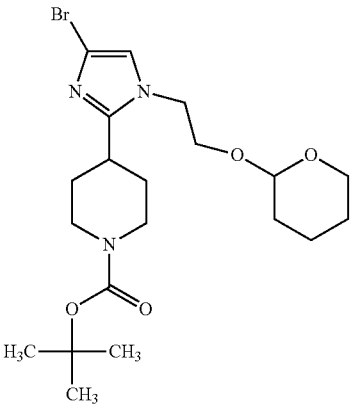 [SMILES: CC(C)(C)OC(=O)N1CCC(c2nc(Br)cn2CCOC2CCCCO2)CC1]

Add tert-butyl 4-(4,5-dibromo-1-(2-(tetrahydro-2H-pyran-2-yloxy)ethyl)-1H-imidazol-2-yl)piperidine-1-carboxylate (46.00 g, 85.61 mmol) in tetrahydrofuran (1 L). Cool to −78° C. under nitrogen. Add 1.6 M butyllithium in hexanes (90.97 mL, 1.7 eq) dropwise over 15 minutes. Maintain the internal temperature below −65° C. After 65 minutes, add isopropyl alcohol (50 mL). Allow to warm to room temperature over 2 hr. Dilute with saturated aqueous ammonium chloride, then extract with ethyl acetate three times. Wash the organics with saturated aqueous sodium chloride. Dry over anhydrous magnesium sulfate, filter, and concentrate in vacuo to give the title compound (43.00 g, 100%). MS (ES) m/z=460 [M]+.

Preparation 82 tert-Butyl 4-(4-cyclopropyl-1-(2-(tetrahydro-2H-pyran-2-yloxy)ethyl)-1H-imidazol-2-yl)piperidine-1-carboxylate

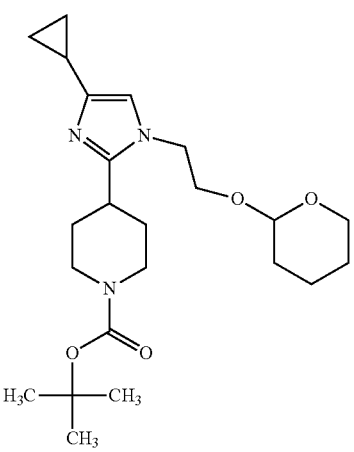

Add tert-butyl 4-(4-bromo-1-(2-(tetrahydro-2H-pyran-2-yloxy)ethyl)-1H-imidazol-2-yl)piperidine-1-carboxylate (1.82 g, 3.97 mmol), cyclopropylboronic acid (0.44 g, 1.3 eq), tricyclohexylphosphine (0.11 g, 0.1 eq), and potassium phosphate (2.95 g, 3.5 eq) in toluene (18 mL) and water (0.9 mL). Degas with nitrogen for 5 minutes. Add palladium acetate (0.045 g, 0.05 eq) and heat at 90° C. overnight. Stop heating after 12 hrs. Dilute with water then extract with ethyl acetate three times. Dry over anhydrous magnesium sulfate and concentrate in vacuo. Purify by silica gel chromatography, eluting with 0-20-50% ethyl acetate/hexanes, then with 1-3-5-7% methanol/dichloromethane, to give the title compound (0.61 g, 37%). MS (ES) m/z=420 [M]+.

Preparation 83

2-(4-Ethyl-2-(piperidin-4-yl)-1H-imidazol-1-yl)ethanol dihydrochloride

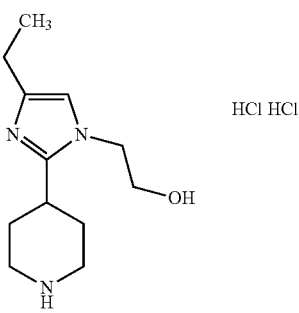 [SMILES: CCc1cn(CCO)c(C2CCNCC2)n1 ; "HCl HCl"]

Combine tert-butyl 4-(4-ethyl-1-(2-(tetrahydro-2H-pyran-2-yloxy)ethyl)-1H-imidazol-2-yl)piperidine-1-carboxylate (4.70 g, 11.53 mmol), dichloromethane (100 mL), and methanol (50 mL). Add hydrogen chloride (20 mL) (4 M in dioxane) slowly. Stir overnight under nitrogen. Concentrate in vacuo to give the title compound (3.40 g, 100%). MS (ES) m/z=224 [M]+.

Prepare the following compounds essentially as described for 2-(4-ethyl-2-(piperidin-4-yl)-1H-imidazol-1-yl)ethanol dihydrochloride:

| Prep | Compound Name | MS (ES) m/z [M]+ |
|---|---|---|
| 84 | 2-(4-methyl-2-(piperidin-4-yl)-1H-imidazol-1-yl)ethanol dihydrochloride | 210 |
| 85 | 2-(2-(piperidin-4-yl)-4-(trifluoromethyl)-1H-imidazol-1-yl)ethanoldihydrochloride | 264 |
| 86 | 2-(4-butyl-2-(piperidin-4-yl)-1H-imidazol-1-yl)ethanol dihydrochloride | 252 |
| 87 | 2-(2-(piperidin-4-yl)-4-propyl-1H-imidazol-1-yl)ethanol dihydrochloride | 238 |
| 88 | 2-(2-(piperidin-4-yl)-4-(tetrahydro-2H-pyran-4-yl)-1H-imidazol-1-yl)ethanol dihydrochloride | 280 |
| 89 | 2-(4-cyclopropyl-2-(piperidin-4-yl)-1H-imidazol-1-yl)ethanol dihydrochloride | 236 |
| 90 | 2-(4-(4-methyltetrahydro-2H-pyran-4-yl)-2-(piperidin-4-yl)-1H-imidazol-1-yl)ethanol dihydrochloride | 294 |
| 90a | 2-(2-(Piperidin-4-yl)-4-(2,2,2-trifluoroethyl)-1H-imidazol-1-yl)ethanol dihydrochloride | 278 |

Preparation 91 tert-Butyl 4-(4-bromo-1-(2-hydroxyethyl)-1H-imidazol-2-yl)piperidine-1-carboxylate

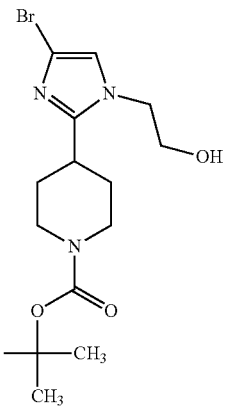

Combine tert-butyl 4-(4-bromo-1-(2-(tetrahydro-2H-pyran-2-yloxy)ethyl)-1H-imidazol-2-yl)piperidine-1-carboxylate (5.00 g, 10.91 mmol), tetrahydrofuran (150 mL), and 1 M aqueous hydrochloric acid (50 mL); let stir overnight at room temperature. Dilute with ethyl acetate. Wash with excess 1M aqueous sodium hydroxide, followed by saturated aqueous sodium chloride. Dry the organics over anhydrous magnesium sulfate, filter, and concentrate in vacuo to give the title compound as a yellow foam (3.84 g, 94%). MS (ES) m/z=376 [M]+.

Prepare the following compounds essentially as described for tert-Butyl 4-(4-bromo-1-(2-hydroxyethyl)-1H-imidazol-2-yl)piperidine-1-carboxylate:

| Prep | Compound Name | MS (ES) m/z [M]+ or 1H NMR |
|---|---|---|
| 92 | tert-butyl 4-(1-(2-hydroxyethyl)-4-propyl-1H-imidazol-2-yl)piperidine-1-carboxylate | 338 |
| 93 | tert-butyl 4-(1-(2-hydroxyethyl)-4-(tetrahydro-2H-pyran-4-yl)-1H-imidazol-2-yl)piperidine-1-carboxylate | 380 |
| 94 | tert-butyl 4-(1-(2-hydroxyethyl)-4-(trifluoromethyl)-1H-imidazol-2-yl)piperidine-1-carboxylate | 364 |
| 95 | tert-butyl 4-(1-(2-hydroxyethyl)-4-methyl-1H-imidazol-2-yl) piperidine-1-carboxylate | 1H NMR (DMSO, 400 MHz) δ 6.70 (s, 1H), 4.91 (m, 1H), 3.97 (m, 3H), 3.91 (m, 2H), 2.90 (m, 3H), 2.00 (s, 3H), 1.70 (m, 2H), 1.60 (m, 4H), 1.40 (s, 9H) |
| 96 | tert-butyl 4-(4-isopropyl-1-(2-hydroxyethyl)-1H-imidazol-2-yl) piperidine-1-carboxylate | 338 |
| 97 | tert-butyl 4-(1-(2-hydroxyethyl)-4-(2-methoxyethyl)-1H-imidazol-2-yl) piperidine-1-carboxylate | 354 |
| 98 | tert-butyl 4-(4-cyclopentyl-1-(2-hydroxyethyl)-1H-imidazol-2-yl) piperidine-1-carboxylate | 364 |
| 99 | tert-butyl 4-(1-(2-hydroxyethyl)-4-(2,2,2-trifluoroethyl)-1H-imidazol-2-yl) piperidine-1-carboxylate | 378 |
| 100 | tert-butyl 4-(4-cyclopropyl-1-(2-hydroxyethyl)-1H-imidazol-2-yl)piperidine-1-carboxylate | 336 |
| 101 | tert-butyl 4-(1-(2-hydroxyethyl)-4-(1-methoxy-2-methylpropan-2-yl)-1H-imidazol-2-yl)piperidine-1-carboxylate | 383 |

Preparation 102 tert-Butyl 4-(1-(2-hydroxyethyl)-4-(tetrahydro-2H-pyran-4-yl)-1H-imidazol-2-yl)piperidine-1-carboxylate

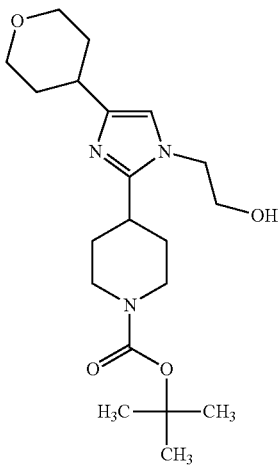 [SMILES: CC(C)(C)OC(=O)N1CCC(c2nc(C3CCOCC3)cn2CCO)CC1]

Combine tert-butyl 4-(1-(2-(tetrahydro-2H-pyran-2-yloxy)ethyl)-4-(tetrahydro-2H-pyran-4-yl)-1H-imidazol-2-yl)piperidine-1-carboxylate (6.88 g, 14.84 mmol), tetrahydrofuran (136 mL) and 1 N aqueous hydrochloric acid (25 mL). Stir the reaction at room temperature overnight. Dilute with ethyl acetate and wash with saturated aqueous sodium chloride and saturated aqueous sodium bicarbonate. Extract the combined aqueous layers with 9:1 dichloromethane:isopropyl alcohol. Dry the combined organic layers over anhydrous sodium sulfate, filter, and concentrate in vacuo. Purify by silica gel chromatography, eluting with hexanes to 50% ethyl acetate in hexanes to ethyl acetate to 10% methanol in ethyl acetate to 10% methanol in dichloromethane, to give the title compound as a white solid (4.48 g, 79%). MS (ES) m/z=380 [M]$^+$.

Preparation 103 tert-Butyl 4-(4-vinyl-1-(2-hydroxyethyl)-1H-imidazol-2-yl)piperidine-1-carboxylate

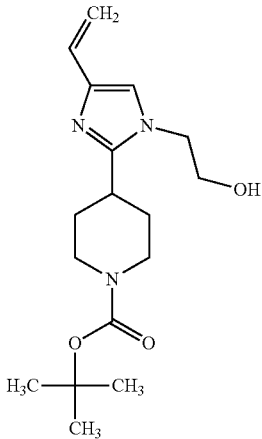

Add tert-butyl 4-(4-bromo-1-(2-hydroxyethyl)-1H-imidazol-2-yl)piperidine-1-carboxylate (42.00 g, 112.22 mmol) in 1,4-dioxane (400 mL) and water (200 mL). Add potassium phosphate, tribasic, N-hydrate (47.64 g, 2.0 eq) and dicyclohexyl-[2-(2,6-dimethoxyphenyl)phenyl]phosphane (5.76 g, 0.12 eq). Degas with nitrogen for 5 minutes. Add 4,4,5,5-tetramethyl-2-vinyl-1,3,2-dioxaborolane (30.25 mL, 1.5 eq) then degas for another 10 minutes. Add palladium acetate (1.26 g, 0.05 eq) and reflux at 120° C. overnight. Stop heating after 12 hrs. Filter through Celite®. Wash with dichloromethane and methanol. Concentrate to dryness in vacuo. Dilute with saturated aqueous sodium chloride then extract with ethyl acetate three times. Dry over anhydrous sodium sulfate and concentrate in vacuo. Purify by silica gel chromatography, eluting with 50-90% ethyl acetate/hexanes, to give the title compound as a yellow foam (20.50 g, 56%). MS (ES) m/z=322 [M]$^+$.

Preparation 104 tert-Butyl 4-(4-ethyl-1-(2-hydroxyethyl)-1H-imidazol-2-yl)piperidine-1-carboxylate

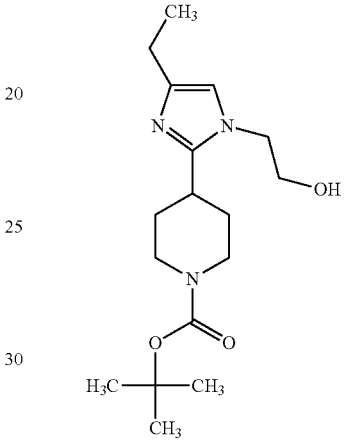

Add 10% palladium on carbon (2.10 g) in ethanol (50 mL). Then add a solution of tert-butyl 4-(1-(2-hydroxyethyl)-4-vinyl-1H-imidazol-2-yl)piperidine-1-carboxylate (20.00 g, 62.22 mmol) in ethanol (200 mL). Cycle through nitrogen and vacuum three times, then hydrogen and vacuum three times. Allow to stir at room temperature under 1 atmosphere hydrogen. After two hours, filter through Celite®. Wash with methanol. Concentrate the filtrate in vacuo to give a light yellow solid as the title compound (20.00 g, 99%). MS (ES) m/z=324 [M]$^+$.

Preparation 105

5-(4-(4-Ethyl-1-(2-hydroxyethyl)-1H-imidazol-2-yl)piperidin-1-yl)-3-(2,2,2-trifluoroethyl)-3,4-dihydropyrimido[4,5-d]pyrimidin-2(1H)-one

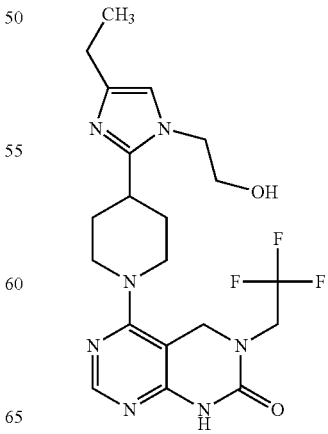

Add 5-chloro-3-(2,2,2-trifluoroethyl)-3,4-dihydropyrimido[4,5-d]pyrimidin-2(1H)-one (0.28 g, 1.05 mmol), 2-(4-ethyl-2-(piperidin-4-yl)-1H-imidazol-1-yl)ethanol dihydrochloride (0.38 g, 1.3 eq), methanol (15 mL) and diisopropylethylamine (0.91 mL, 5.0 eq) into a 20 mL microwave vial. Seal the tube and heat in a microwave reactor to 150° C., for 1 hour. Filter through silica gel, eluting with 10% ammonia-methanol/dichloromethane. Concentrate the filtrate in vacuo. Purify by silica gel chromatography, eluting with 3:1 ethyl acetate/methanol, to give the title compound as a yellow foam (0.67 g, 70%). MS (ES) m/z=454 [M]$^+$.

Prepare the following compounds essentially as described for 5-(4-(4-ethyl-1-(2-hydroxyethyl)-1H-imidazol-2-yl)piperidin-1-yl)-3-(2,2,2-trifluoroethyl)-3,4-dihydropyrimido[4,5-d]pyrimidin-2(1H)-one:

| Prep | Compound Name | MS (ES) m/z [M]$^+$ |
|---|---|---|
| 106 | (R)-4-(4-(4-ethyl-1-(2-hydroxyethyl)-1H-imidazol-2-yl)piperidin-1-yl)-5-methyl-5,6-dihydropyrido[2,3-d]pyrimidin-7(8H)-one | 385 |
| 107 | (R)-4-(4-(1-(2-hydroxyethyl)-4-methyl-1H-imidazol-2-yl)piperidin-1-yl)-5-methyl-5,6-dihydropyrido[2,3-d]pyrimidin-7(8H)-one | 371 |
| 108 | (R)-4-(4-(1-(2-hydroxyethyl)-4-(trifluoromethyl)-1H-imidazol-2-yl)piperidin-1-yl)-5-methyl-5,6-dihydropyrido[2,3-d]pyrimidin-7(8H)-one | 425 |
| 109 | (R)-4-(4-(4-butyl-1-(2-hydroxyethyl)-1H-imidazol-2-yl)piperidin-1-yl)-5-(trifluoromethyl)-5,6-dihydropyrido[2,3-d]pyrimidin-7(8H)-one | 467 |
| 110 | (R)-4-(4-(4-butyl-1-(2-hydroxyethyl)-1H-imidazol-2-yl)piperidin-1-yl)-5-methyl-5,6-dihydropyrido[2,3-d]pyrimidin-7(8H)-one | 413 |
| 111 | (R)-4-(4-(1-(2-hydroxyethyl)-4-propyl-1H-imidazol-2-yl)piperidin-1-yl)-5-(trifluoromethyl)-5,6-dihydropyrido[2,3-d]pyrimidin-7(8H)-one | 453 |
| 112 | (R)-4-(4-(4-ethyl-1-(2-hydroxyethyl)-1H-imidazol-2-yl)piperidin-1-yl)-5-(trifluoromethyl)-5,6-dihydropyrido[2,3-d]pyrimidin-7(8H)-one | 439 |
| 113 | (R)-4-(4-(1-(2-hydroxyethyl)-4-(tetrahydro-2H-pyran-4-yl)-1H-imidazol-2-yl)piperidin-1-yl)-5-methyl-5,6-dihydropyrido[2,3-d]pyrimidin-7(8H)-one | 441 |
| 114 | (R)-4-(4-(4-cyclopropyl-1-(2-hydroxyethyl)-1H-imidazol-2-yl)piperidin-1-yl)-5-(trifluoromethyl)-5,6-dihydropyrido[2,3-d]pyrimidin-7(8H)-one | 451 |
| 115 | (R)-4-(4-(1-(2-hydroxyethyl)-4-(4-methyltetrahydro-2H-pyran-4-yl)-1H-imidazol-2-yl)piperidin-1-yl)-5-(trifluoromethyl)-5,6-dihydropyrido[2,3-d]pyrimidin-7(8H)-one | 509 |
| 115a | (R)-4-(4-(1-(2-Hydroxyethyl)-4-propyl-1H-imidazol-2-yl)piperidin-1-yl)-5-methyl-5,6-dihydropyrido[2,3-d]pyrimidin-7(8H)-one | 399 |
| 115b | (R)-4-(4-(1-(2-Hydroxyethyl)-4-(2,2,2-trifluoroethyl)-1H-imidazol-2-yl)piperidin-1-yl)-5-methyl-5,6-dihydropyrido[2,3-d]pyrimidin-7(8H)-one | 439 |
| 115c | (R)-4-(4-(1-(2-Hydroxyethyl)-4-(4-methyltetrahydro-2H-pyran-4-yl)-1H-imidazol-2-yl)piperidin-1-yl)-5-methyl-5,6-dihydropyrido[2,3-d]pyrimidin-7(8H)-one | 455 |

Preparation 116 tert-Butyl 4-(4-bromo-1-(2-(methylsulfonyloxy)ethyl)-1H-imidazol-2-yl)piperidine-1-carboxylate

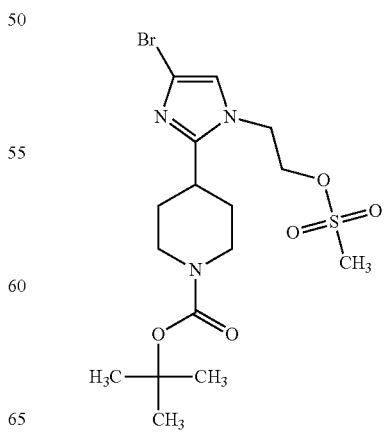

Combine tert-butyl 4-(4-bromo-1-(2-hydroxyethyl)-1H-imidazol-2-yl)piperidine-1-carboxylate (3.84 g, 10.26 mmol), dichloromethane (60 mL), and triethylamine (4.29 mL, 3.0 eq). Place under nitrogen and cool to 0° C. Add methanesulfonyl chloride (0.95 mL, 1.2 eq) dropwise. After 15 minutes, quench with saturated aqueous sodium bicarbonate. Wash the organics with saturated aqueous sodium chloride. Dry the organics over anhydrous magnesium sulfate, filter, and concentrate in vacuo to give the title compound (4.45 g, 96%). MS (ES) m/z=452 [M]+.

Prepare the following compounds essentially as described for tert-butyl 4-(4-bromo-1-(2-(methylsulfonyloxy)ethyl)-1H-imidazol-2-yl)piperidine-1-carboxylate:

| Prep | Compound Name | MS (ES) m/z [M]+ |
|---|---|---|
| 117 | tert-butyl 4-(4-ethyl-1-(2-(methylsulfonyloxy)ethyl)-1H-imidazol-2-yl)piperidine-1-carboxylate | 402 |
| 118 | tert-butyl 4-(1-(2-(methylsulfonyloxy)ethyl)-4-(tetrahydro-2H-pyran-4-yl)-1H-imidazol-2-yl)piperidine-1-carboxylate | 458 |
| 119 | tert-butyl 4-(1-(2-(methylsulfonyloxy)ethyl)-4-propyl-1H-imidazol-2-yl)piperidine-1-carboxylate | 416 |
| 120 | (R)-2-(4-ethyl-2-(1-(5-methyl-7-oxo-5,6,7,8-tetrahydropyrido[2,3-d]pyrimidin-4-yl)piperidin-4-yl)-1H-imidazol-1-yl)ethyl methanesulfonate | 463 |
| 121 | 2-(4-ethyl-2-(1-(7-oxo-6-(2,2,2-trifluoroethyl)-5,6,7,8-tetrahydropyrimido[4,5-d]pyrimidin-4-yl)piperidin-4-yl)-1H-imidazol-1-yl)ethyl methanesulfonate | 532 |
| 122 | (R)-2-(4-methyl-2-(1-(5-methyl-7-oxo-5,6,7,8-tetrahydropyrido[2,3-d]pyrimidin-4-yl)piperidin-4-yl)-1H-imidazol-1-yl)ethyl methanesulfonate | 449 |
| 123 | (R)-2-(2-(1-(5-methyl-7-oxo-5,6,7,8-tetrahydropyrido[2,3-d]pyrimidin-4-yl)piperidin-4-yl)-4-(trifluoromethyl)-1H-imidazol-1-yl)ethyl methanesulfonate | 503 |
| 124 | tert-butyl 4-(4-methyl-1-(2-(methylsulfonyloxy) ethyl)-1H-imidazol-2-yl) piperidine-1-carboxylate | 388 |
| 125 | tert-butyl 4-(4-isopropyl-1-(2-(methylsulfonyloxy) ethyl)-1H-imidazol-2-yl) piperidine-1-carboxylate | 416 |
| 126 | tert-butyl 4-(4-(2-methoxyethyl)-1-(2-(methylsulfonyloxy) ethyl)-1H-imidazol-2-yl) piperidine-1-carboxylate | 433 |
| 127 | tert-butyl 4-(4-cyclopentyl-1-(2-(methylsulfonyloxy) ethyl)-1H-imidazol-2-yl) piperidine-1-carboxylate | 442 |
| 128 | tert-butyl 4-(1-(2-(methylsulfonyloxy) ethyl)-4-(2,2,2-trifluoroethyl)-1H-imidazol-2-yl) piperidine-1-carboxylate | 456 |
| 129 | tert-butyl 4-(4-cyclopropyl-1-(2-(methylsulfonyloxy)ethyl)-1H-imidazol-2-yl)piperidine-1-carboxylate | 414 |
| 130 | tert-butyl 4-(4-(1-methoxy-2-methylpropan-2-yl)-1-(2-(methylsulfonyloxy)ethyl)-1H-imidazol-2-yl)piperidine-1-carboxylate | 443 |
| 131 | tert-butyl 4-(1-(2-(methylsulfonyloxy)ethyl)-4-(trifluoromethyl)-1H-imidazol-2-yl)piperidine-1-carboxylate | 442 |
| 132 | (R)-2-(2-(1-(7-oxo-5-trifluoromethyl-5,6,7,8-tetrahydropyrido[2,3-d]pyrimidin-4-yl)piperidin-4-yl)-4-butyl-1H-imidazol-1-yl)ethyl methanesulfonate | 545 |
| 133 | (R)-2-(2-(1-(5-methyl-7-oxo-5,6,7,8-tetrahydropyrido[2,3-d]pyrimidin-4-yl)piperidin-4-yl)-4-butyl-1H-imidazol-1-yl)ethyl methanesulfonate | 491 |
| 134 | (R)-2-(2-(1-(7-oxo-5-trifluoromethyl-5,6,7,8-tetrahydropyrido[2,3-d]pyrimidin-4-yl)piperidin-4-yl)-4-propyl-1H-imidazol-1-yl)ethyl methanesulfonate | 531 |
| 135 | (R)-2-(2-(1-(7-oxo-5-trifluoromethyl-5,6,7,8-tetrahydropyrido[2,3-d]pyrimidin-4-yl)piperidin-4-yl)-4-ethyl-1H-imidazol-1-yl)ethyl methanesulfonate | 517 |
| 136 | (R)-2-(2-(1-(5-methyl-7-oxo-5,6,7,8-tetrahydropyrido[2,3-d]pyrimidin-4-yl)piperidin-4-yl)-4-(tetrahydro-2H-pyran-4-yl)-1H-imidazol-1-yl)ethyl methanesulfonate | 519 |
| 137 | (R)-2-(2-(1-(7-oxo-5-trifluoromethyl-5,6,7,8-tetrahydropyrido[2,3-d]pyrimidin-4-yl)piperidin-4-yl)-4-cyclopropyl-1H-imidazol-1-yl)ethyl methanesulfonate | 529 |
| 138 | (R)-2-(2-(1-(7-oxo-5-trifluoromethyl-5,6,7,8-tetrahydropyrido[2,3-d]pyrimidin-4-yl)piperidin-4-yl)-4-(4-methyltetrahydro-2H-pyran-4-yl)-1H-imidazol-1-yl)ethyl methanesulfonate | 587 |
| 138a | (R)-2-(2-(1-(5-Methyl-7-oxo-5,6,7,8-tetrahydropyrido[2,3-d]pyrimidin-4-yl)piperidin-4-yl)-4-propyl-1H-imidazol-1-yl)ethyl methanesulfonate | 477 |
| 138b | (R)-2-(2-(1-(5-Methyl-7-oxo-5,6,7,8-tetrahydropyrido[2,3-d]pyrimidin-4-yl)piperidin-4-yl)-4-(2,2,2-trifluoroethyl)-1H-imidazol-1-yl)ethyl methanesulfonate | 517 |
| 138c | (R)-2-(2-(1-(5-Methyl-7-oxo-5,6,7,8-tetrahydropyrido[2,3-d]pyrimidin-4-yl)piperidin-4-yl)-4-(4-methyltetrahydro-2H-pyran-4-yl)-1H-imidazol-1-yl)ethyl methanesulfonate | 533 |

Preparation 139 tert-Butyl 4-(1-(2-(methylsulfonyloxy)ethyl)-4-(tetrahydro-2H-pyran-4-yl)-1H-imidazol-2-yl)piperidine-1-carboxylate

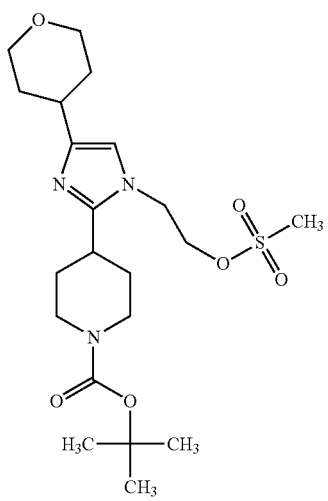 [SMILES: CC(C)(C)OC(=O)N1CCC(c2nc(C3CCOCC3)cn2CCOS(C)(=O)=O)CC1]

Combine tert-butyl 4-(1-(2-hydroxyethyl)-4-(tetrahydro-2H-pyran-4-yl)-1H-imidazol-2-yl)piperidine-1-carboxylate (4.40 g, 11.60 mmol) and triethylamine (4.9 mL, 3.0 eq) in dichloromethane (72 mL). Cool to 0° C. and add methanesulfonyl chloride (1.1 mL, 1.2 eq). After 1 hour, dilute with additional dichloromethane and saturated aqueous sodium bicarbonate. Separate the layers. Dry the organics over anhydrous sodium sulfate, filter, and concentrate in vacuo to give the title compound as a light yellow solid (5.05 g, 95%). MS (ES) m/z=458 [M]$^+$.

Preparation 140 tert-Butyl 4-(4-bromo-1-(2-(pyrrolidin-1-yl)ethyl)-1H-imidazol-2-yl)piperidine-1-carboxylate

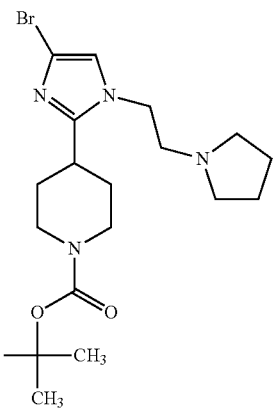

Combine tert-butyl 4-(4-bromo-1-(2-(methylsulfonyloxy)ethyl)-1H-imidazol-2-yl)piperidine-1-carboxylate (4.45 g, 9.84 mmol), dimethylformamide (25 mL), and pyrrolidine (2.46 mL, 3.0 eq) under nitrogen. Heat the reaction mixture at 50° C. overnight, then allow to cool to room temperature. Dilute with ethyl acetate. Wash with water followed by saturated aqueous sodium chloride. Dry the organics over anhydrous magnesium sulfate, filter, and concentrate in vacuo to give the title compound (4.12 g, 98%). MS (ES) m/z=427 [M]$^+$.

Prepare the following compounds essentially as described for tert-butyl 4-(4-bromo-1-(2-(pyrrolidin-1-yl)ethyl)-1H-imidazol-2-yl)piperidine-1-carboxylate:

| Prep | Compound Name | MS (ES) m/z [M]$^+$ |
|---|---|---|
| 141 | tert-butyl 4-(4-propyl-1-(2-(pyrrolidin-1-yl)ethyl)-1H-imidazol-2-yl)piperidine-1-carboxylate | 391 |
| 142 | tert-butyl 4-(4-methyl-1-(2-(pyrrolidin-1-yl)ethyl)-1H-imidazol-2-yl)piperidine-1-carboxylate | 363 |
| 143 | (S)-tert-butyl 4-(1-(2-(3-hydroxypyrrolidin-1-yl)ethyl)-4-isopropyl-1H-imidazol-2-yl)piperidine-1-carboxylate | 407 |
| 144 | (R)-tert-butyl 4-(1-(2-(3-hydroxypyrrolidin-1-yl)ethyl)-4-isopropyl-1H-imidazol-2-yl)piperidine-1-carboxylate | 407 |
| 145 | tert-butyl 4-(1-(2-(dimethylamino)ethyl)-4-ethyl-1H-imidazol-2-yl)piperidine-1-carboxylate | 351 |
| 146 | tert-butyl 4-[1-[2-(cyclopentylamino)ethyl]-4-ethyl-imidazol-2-yl]piperidine-1-carboxylate | 391 |
| 147 | tert-butyl 4-(1-(2-(tert-butylamino)ethyl)-4-cyclopentyl-1H-imidazol-2-yl)piperidine-1-carboxylate | 419 |
| 148 | tert-butyl 4-(1-(2-(tert-butylamino)ethyl)-4-(trifluoromethyl)-1H-imidazol-2-yl)piperidine-1-carboxylate | 419 |
| 149 | tert-butyl 4-(1-(2-(tert-butylamino)ethyl)-4-(tetrahydro-2H-pyran-4-yl)-1H-imidazol-2-yl)piperidine-1-carboxylate | 435 |
| 150 | tert-butyl 4-(1-(2-(tert-butylamino)ethyl)-4-(2,2,2-trifluoroethyl)-1H-imidazol-2-yl)piperidine-1-carboxylate | 433 |
| 151 | tert-butyl 4-(1-(2-(cyclopropylmethylamino)ethyl)-4-ethyl-1H-imidazol-2-yl)piperidine-1-carboxylate | 377 |
| 152 | tert-butyl 4-(1-(2-(tert-butylamino)ethyl)-4-isopropyl-1H-imidazol-2-yl)piperidine-1-carboxylate | 393 |
| 153 | tert-butyl 4-(4-ethyl-1-(2-(pyrrolidin-1-yl)ethyl)-1H-imidazol-2-yl)piperidine-1-carboxylate | 377 |

-continued

| Prep | Compound Name | MS (ES) m/z [M]+ |
|---|---|---|
| 154 | tert-butyl 4-(4-ethyl-1-(2-(isopropylamino)ethyl)-1H-imidazol-2-yl)piperidine-1-carboxylate | 365 |
| 155 | tert-butyl 4-(4-isopropyl-1-(2-(isopropylamino)ethyl)-1H-imidazol-2-yl)piperidine-1-carboxylate | 379 |
| 156 | tert-butyl 4-[4-cyclopropyl-1-(2-pyrrolidin-1-ylethyl)imidazol-2-yl]piperidine-1-carboxylate | 389 |
| 157 | tert-butyl 4-[4-isopropyl-1-(2-pyrrolidin-1-ylethyl)imidazol-2-yl]piperidine-1-carboxylate | 391 |
| 158 | tert-butyl 4-(1-(2-(cyclobutylamino)ethyl)-4-(trifluoromethyl)-1H-imidazol-2-yl)piperidine-1-carboxylate | 417 |
| 159 | tert-butyl 4-(1-(2-(tert-butylamino)ethyl)-4-cyclopropyl-1H-imidazol-2-yl)piperidine-1-carboxylate | 392 |
| 160 | tert-butyl 4-(1-(2-(tert-butylamino)ethyl)-4-ethyl-1H-imidazol-2-yl)piperidine-1-carboxylate | 377 |
| 161 | tert-butyl 4-(4-(2-methoxyethyl)-1-(2-(pyrrolidin-1-yl)ethyl)-1H-imidazol-2-yl)piperidine-1-carboxylate | 407 |
| 162 | tert-butyl 4-(4-(1-methoxy-2-methylpropan-2-yl)-1-(2-(pyrrolidin-1-yl)ethyl)-1H-imidazol-2-yl)piperidine-1-carboxylate | 435 |
| 163 | tert-butyl 4-(4-ethyl-1-(2-(tetrahydropyran-4-ylamino)ethyl)-1H-imidazol-2-yl)piperidine-1-carboxylate | 407 |

Preparation 164 tert-Butyl 4-(1-(2-(pyrrolidin-1-yl)ethyl)-4-(tetrahydro-2H-pyran-4-yl)-1H-imidazol-2-yl)piperidine-1-carboxylate

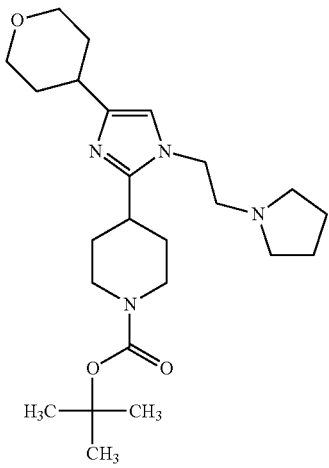 [SMILES: CC(C)(C)OC(=O)N1CCC(c2nc(C3CCOCC3)cn2CCN2CCCC2)CC1]

Combine tert-butyl 4-(1-(2-(methylsulfonyloxy)ethyl)-4-(tetrahydro-2H-pyran-4-yl)-1H-imidazol-2-yl)piperidine-1-carboxylate (2.02 g, 4.42 mmol), pyrrolidine (1.1 mL, 3.0 eq), and dimethylformamide (19 mL). Heat the reaction mixture to 50° C. overnight. Dilute with dichloromethane and saturated aqueous sodium bicarbonate. Separate the layers. Wash the organics with water. Dry the organics over anhydrous sodium sulfate, filter, and concentrate in vacuo. Purify by silica gel chromatography, eluting with hexanes to ethyl acetate to 10% methanol in dichloromethane, to give the title compound as a yellow oil (1.79 g, 93%). MS (ES) m/z=433 [M]+.

Preparation 165 tert-Butyl 4-(1-(2-(pyrrolidin-1-yl)ethyl)-4-vinyl-1H-imidazol-2-yl)piperidine-1-carboxylate

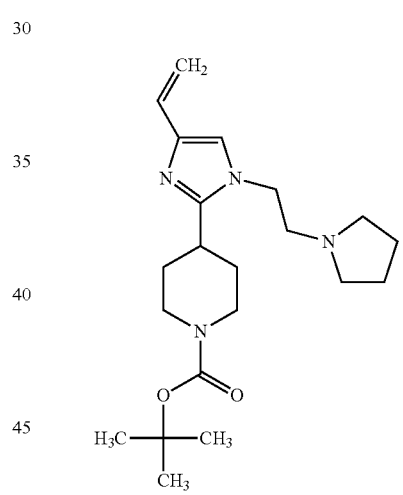

Add tert-butyl 4-(4-bromo-1-(2-(pyrrolidin-1-yl)ethyl)-1H-imidazol-2-yl)piperidine-1-carboxylate (0.26 g, 0.60 mmol) in 1,4-dioxane (4 mL) and water (1 mL). Add potassium phosphate, tribasic, N-hydrate (0.26 g, 2.0 eq) and dicyclohexyl-[2-(2,6-dimethoxyphenyl)phenyl]phosphane (0.036 g, 0.15 eq). Add 4,4,5,5-tetramethyl-2-vinyl-1,3,2-dioxaborolane (0.22 mL, 2.05 eq) and degas for 10 minutes. Add bis(dibenzylideneacetone)palladium(0) (0.03 g, 0.06 eq) and reflux at 150° C. for 1 hour. Filter through Celite®. Wash with dichloromethane. Concentrate the filtrate to dryness in vacuo. Purify by silica gel chromatography, eluting with 25% methanol/ethyl acetate, to give the title compound as a yellow foam (0.14 g, 38%). MS (ES) m/z=375 [M]+.

Preparation 166
4-(4-Bromo-1-(2-(pyrrolidin-1-yl)ethyl)-1H-imidazol-2-yl)piperidine trihydrochloride

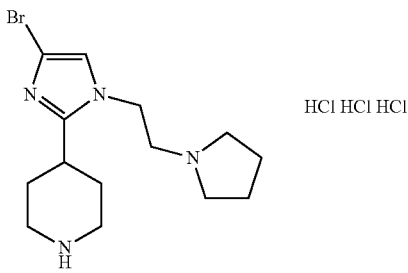 [SMILES: Brc1cn(CCN2CCCC2)c(C2CCNCC2)n1]

Combine tert-butyl 4-(4-bromo-1-(2-(pyrrolidin-1-yl)ethyl)-1H-imidazol-2-yl)piperidine-1-carboxylate (0.80 g, 1.87 mmol), dichloromethane (20 mL), methanol (8 mL), and 4M hydrochloric acid in dioxane (9.36 mL, 20.0 eq) under nitrogen and let stir at room temperature. After 1.5 hours, concentrate in vacuo to give the title compound (0.82 g, 100%). MS (ES) m/z=327 [M]$^+$.

Prepare the following compounds essentially as described for 4-(4-bromo-1-(2-(pyrrolidin-1-yl)ethyl)-1H-imidazol-2-yl)piperidine trihydrochloride (a basic workup affords the free base in some instances):

| Prep | Compound Name | MS (ES) m/z [M]$^+$ |
|---|---|---|
| 167 | 4-(4-propyl-1-(2-(pyrrolidin-1-yl)ethyl)-1H-imidazol-2-yl)piperidine trihydrochloride | 291 |
| 168 | 4-(4-methyl-1-(2-(pyrrolidin-1-yl)ethyl)-1H-imidazol-2-yl)piperidine | 263 |
| 169 | 4-(4-(3,3,3-trifluoropropyl)-1-(2-(pyrrolidin-1-yl)ethyl)-1H-imidazol-2-yl)piperidine tris(2,2,2-trifluoroacetate) | 345 |
| 170 | 4-(4-(1-methylcyclobutyl)-1-(2-(pyrrolidin-1-yl)ethyl)-1H-imidazol-2-yl)piperidine dihydrochloride | 317 |
| 171 | 4-(4-(2-methoxyethyl)-1-(2-(pyrrolidin-1-yl)ethyl)-1H-imidazol-2-yl)piperidine tris(2,2,2-trifluoroacetate) | 307 |
| 172 | 4-(4-cyclobutyl-1-(2-(pyrrolidin-1-yl)ethyl)-1H-imidazol-2-yl)piperidine trihydrochloride | 303 |
| 173 | 4-(1-(2-(pyrrolidin-1-yl)ethyl)-1H-imidazol-2-yl)piperidine trihydrochloride | 249 |
| 174 | N-(2-(4-ethyl-2-(piperidin-4-yl)-1H-imidazol-1-yl)ethyl)cyclopentanamine | 290 |
| 175 | 4-(4-(1-methylcyclopropyl)-1-(2-(pyrrolidin-1-yl)ethyl)-1H-imidazol-2-yl)piperidine | 302 |
| 176 | N-(2-(4-cyclopentyl-2-(piperidin-4-yl)-1H-imidazol-1-yl)ethyl)-2-methylpropan-2-amine | 319 |
| 177 | 2-methyl-N-(2-(2-(piperidin-4-yl)-4-(trifluoromethyl)-1H-imidazol-1-yl)ethyl)propan-2-amine | 319 |
| 178 | 2-methyl-N-(2-(2-(piperidin-4-yl)-4-(tetrahydro-2H-pyran-4-yl)-1H-imidazol-1-yl)ethyl)propan-2-amine trihydrochloride | 335 |
| 179 | 2-methyl-N-(2-(2-(piperidin-4-yl)-4-(2,2,2-trifluoroethyl)-1H-imidazol-1-yl)ethyl)propan-2-amine trihydrochloride | 333 |
| 180 | N-(2-(4-isopropyl-2-(piperidin-4-yl)-1H-imidazol-1-yl)ethyl)-2-methylpropan-2-amine | 293 |
| 181 | 4-(4-cyclopentyl-1-(2-(pyrrolidin-1-yl)ethyl)-1H-imidazol-2-yl)piperidine hydrochloride | 317 |
| 182 | 4-(4-cyclohexyl-1-(2-(pyrrolidin-1-yl)ethyl)-1H-imidazol-2-yl)piperidine | 330 |
| 183 | N-(2-(4-isopropyl-2-(piperidin-4-yl)-1H-imidazol-1-yl)ethyl)propan-2-amine trihydrochloride | 279 |
| 184 | 4-(4-cyclopropyl-1-(2-(pyrrolidin-1-yl)ethyl)-1H-imidazol-2-yl)piperidine | 289 |
| 185 | 4-(4-isopropyl-1-(2-(pyrrolidin-1-yl)ethyl)-1H-imidazol-2-yl)piperidine | 291 |
| 186 | N-(2-(2-(piperidin-4-yl)-4-(trifluoromethyl)-1H-imidazol-1-yl)ethyl)cyclobutanamine | 317 |
| 187 | 4-(4-vinyl-1-(2-(pyrrolidin-1-yl)ethyl)-1H-imidazol-2-yl)piperidine tris(2,2,2-trifluoroacetate) | 275 |
| 188 | 2-(piperidin-4-yl)-1-(2-(pyrrolidin-1-yl)ethyl)-1H-imidazole-4-carbonitrile trihydrochloride | 274 |
| 189 | 4-(4-isobutyl-1-(2-(pyrrolidin-1-yl)ethyl)-1H-imidazol-2-yl)piperidine trihydrochloride | 305 |
| 190 | 4-(4-(2,2,2-trifluoroethyl)-1-(2-(pyrrolidin-1-yl)ethyl)-1H-imidazol-2-yl)piperidine trihydrochloride | 331 |
| 191 | 4-(4-ethyl-1-(2-(pyrrolidin-1-yl)ethyl)-1H-imidazol-2-yl)piperidine trihydrochloride | 277 |
| 192 | 4-(4-tert-butyl-1-(2-(pyrrolidin-1-yl)ethyl)-1H-imidazol-2-yl)piperidine trihydrochloride | 305 |
| 193 | N-(2-(4-cyclopropyl-2-(piperidin-4-yl)-1H-imidazol-1-yl)ethyl)-2-methylpropan-2-amine | 291 |
| 194 | N-(2-(4-ethyl-2-(piperidin-4-yl)-1H-imidazol-1-yl)ethyl)-2-methylpropan-2-amine trihydrochloride | 279 |
| 195 | 4-(4-(1-methoxy-2-methylpropan-2-yl)-1-(2-(pyrrolidin-1-yl)ethyl)-1H-imidazol-2-yl) piperidine | 335 |

| Prep | Compound Name | MS (ES) m/z [M]+ |
|---|---|---|
| 196 | 4-(4,5-dichloro-1-(2-(pyrrolidin-1-yl)ethyl)-1H-imidazol-2-yl) piperidine | 317 |
| 197 | 4-(4-chloro-1-(2-(pyrrolidin-1-yl)ethyl)-1H-imidazol-2-yl) piperidine trihydrochloride | 283 |
| 198 | 4-(4-butyl-1-(2-(pyrrolidin-1-yl)ethyl)-1H-imidazol-2-yl) piperidine trihydrochloride | 305 |
| 199 | N-(2-(4-ethyl-2-(piperidin-4-yl)-1H-imidazol-1-yl)ethyl)tetrahydropyran-4-amine trihydrochloride | 307 |
| 200 | 4-(1-(2-(pyrrolidin-1-yl)ethyl)-4-(trifluoromethyl)-1H-imidazol-2-yl)piperidine trihydrochloride | 317 |

Preparation 201

4-(4-(Tetrahydro-2H-pyran-4-yl)-1-(2-(pyrrolidin-1-yl)ethyl)-1H-imidazol-2-yl)piperidine

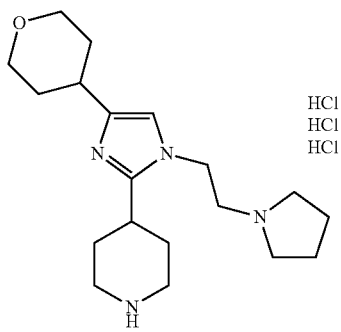 [SMILES: c1c(C2CCOCC2)nc(C2CCNCC2)n1CCN1CCCC1]

Combine tert-butyl 4-(1-(2-(pyrrolidin-1-yl)ethyl)-4-(tetrahydro-2H-pyran-4-yl)-1H-imidazol-2-yl)piperidine-1-carboxylate (1.74 g, 4.03 mmol), dichloromethane (53 mL) and methanol (21 mL). Add 4 M hydrogen chloride in 1,4-dioxane (10.4 mL, 10.3 eq). After one hour, concentrate in vacuo. Dry the resulting residue under vacuum to give the title compound as a white solid (1.67 g, 94%). MS (ES) m/z=333 [M]+.

Preparation 202

4-(4-Trifluoromethyl-1-(2-(pyrrolidin-1-yl)ethyl)-1H-imidazol-2-yl)piperidine

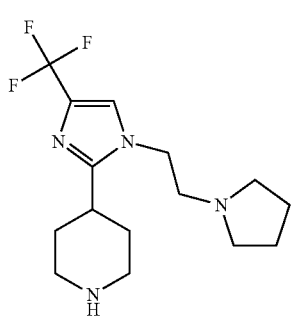 [SMILES: FC(F)(F)c1cn(CCN2CCCC2)c(C2CCNCC2)n1]

Add tert-butyl 4-(4-(trifluoromethyl)-1-(2-pyrrolidin-1-ylethyl)-1H-imidazol-2-yl)piperidine-1-carboxylate succinate (120 g, 224.48 mmol) in methanol (720 mL) to 37% aqueous hydrogen chloride (76.08 mL, 4 eq) at room temperature. Stir the solution at 50° C. Concentrate the reaction mixture. Add 500 mL water and wash with methyl tert-butyl ether (200 mL). Basify the aqueous solution with 6M aqueous sodium hydroxide at 0° C. Extract with ethyl acetate (4×200 mL). Dry the organics over anhydrous sodium sulfate and concentrate in vacuo to give the title compound (68 g, 96%). MS (ES) m/z=317 [M]+.

EXAMPLE 1

(R)-4-(4-(1-(2-(tert-Butylamino)ethyl)-4-(trifluoromethyl)-1H-imidazol-2-yl)piperidin-1-yl)-5-methyl-5,6-dihydropyrido[2,3-d]pyrimidin-7(8H)-one

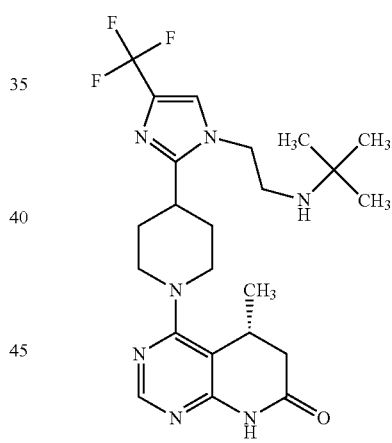

Add (R)-2-(2-(1-(5-methyl-7-oxo-5,6,7,8-tetrahydropyrido[2,3-d]pyrimidin-4-yl)piperidin-4-yl)-4-(trifluoromethyl)-1H-imidazol-1-yl)ethyl methanesulfonate (0.50 g, 0.99 mmol), tert-butylamine (0.52 mL, 7.1 eq), and triethylamine (0.69 mL, 5.0 eq) in dimethylformamide (5 mL). Heat to 50° C. in a sealed tube for 48 hours. Dilute the solution with saturated aqueous sodium chloride. Add the mixture into ethyl acetate. Wash the organics with saturated aqueous sodium chloride and concentrate in vacuo. Purify by silica gel chromatography, eluting with 20% ethanol/acetone, to give the title compound (0.27 g, 55%). MS (ES) m/z=480 [M]+.

Prepare the following compounds essentially as described for (R)-4-(4-(1-(2-(tert-butylamino)ethyl)-4-(trifluoromethyl)-1H-imidazol-2-yl)piperidin-1-yl)-5-methyl-5,6-dihydropyrido[2,3-d]pyrimidin-7(8H)-one (alternative purification for Ex 3; concentrate the reaction mixture and filter from isopropanol to give the desired product as the mesylate salt):

| Ex | Compound Name | Structure | MS (ES) m/z [M]+ |
|---|---|---|---|
| 2 | (R)-4-(4-(1-(2-(azetidin-1-yl)ethyl)-4-ethyl-1H-imidazol-2-yl)piperidin-1-yl)-5-methyl-5,6-dihydropyrido[2,3-d]pyrimidin-7(8H)-one | 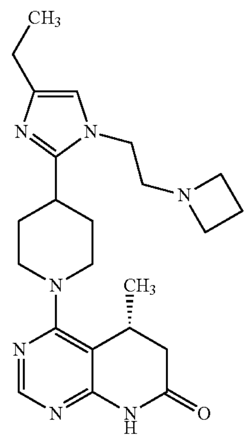 [SMILES: CCc1cn(CCN2CCC2)c(C2CCN(c3ncnc4c3[C@H](C)CC(=O)N4)CC2)n1] | 424 |
| 3 | (R)-5-methyl-4-(4-(1-(2-(methylamino)ethyl)-4-(trifluoromethyl)-1H-imidazol-2-yl)piperidin-1-yl)-5,6-dihydropyrido[2,3-d]pyrimidin-7(8H)-one methanesulfonate | 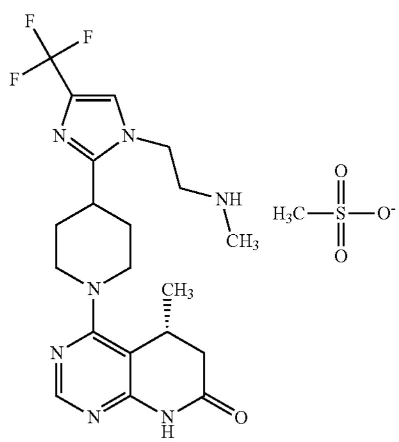 | 438 |
| 4 | 5-(4-(4-ethyl-1-(2-(pyrrolidin-1-yl)ethyl)-1H-imidazol-2-yl)piperidin-1-yl)-3-(2,2,2-trifluoroethyl)-3,4-dihydropyrimido[4,5-d]pyrimidin-2(1H)-one | 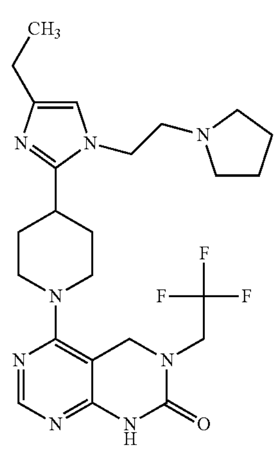 [SMILES: CCc1cn(CCN2CCCC2)c(C2CCN(c3ncnc4c3CN(CC(F)(F)F)C(=O)N4)CC2)n1] | 507 |

-continued

| Ex | Compound Name | Structure | MS (ES) m/z [M]+ |
|---|---|---|---|
| 5 | (R)-5-methyl-4-(4-(1-(2-(tert-pentylamino)ethyl)-4-(trifluoromethyl)-1H-imidazol-2-yl)piperidin-1-yl)-5,6-dihydropyrido[2,3-d]pyrimidin-7(8H)-one | 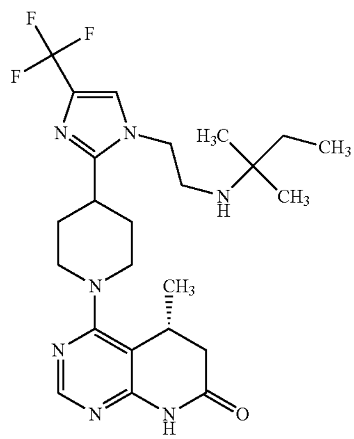 [SMILES: CCC(C)(C)NCCn1cc(C(F)(F)F)nc1C1CCN(c2ncnc3c2[C@H](C)CC(=O)N3)CC1] | 494 |
| 6 | (R)-4-(4-(1-(2-(cyclopropylmethylamino)ethyl)-4-(trifluoromethyl)-1H-imidazol-2-yl)piperidin-1-yl)-5-methyl-5,6-dihydropyrido[2,3-d]pyrimidin-7(8H)-one | 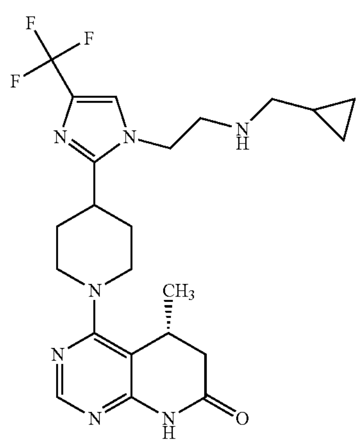 [SMILES: C[C@@H]1CC(=O)Nc2ncnc(N3CCC(c4nc(C(F)(F)F)cn4CCNCC4CC4)CC3)c21] | 478 |
| 7 | (R)-5-methyl-4-(4-(4-methyl-1-(2-(pyrrolidin-1-yl)ethyl)-1H-imidazol-2-yl)piperidin-1-yl)-5,6-dihydropyrido[2,3-d]pyrimidin-7(8H)-one | 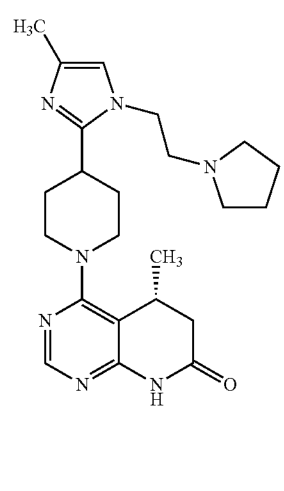 [SMILES: Cc1cn(CCN2CCCC2)c(C2CCN(c3ncnc4c3[C@H](C)CC(=O)N4)CC2)n1] | 424 |

| Ex | Compound Name | Structure | MS (ES) m/z [M]+ |
|---|---|---|---|
| 8 | (R)-4-(4-(1-(2-(azetidin-1-yl)ethyl)-4-(trifluoromethyl)-1H-imidazol-2-yl)piperidin-1-yl)-5-methyl-5,6-dihydropyrido[2,3-d]pyrimidin-7(8H)-one | 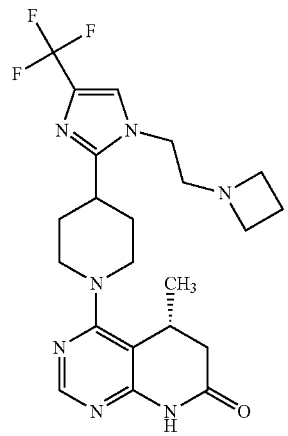 [SMILES: C[C@@H]1CC(=O)Nc2ncnc(N3CCC(c4nc(C(F)(F)F)cn4CCN4CCC4)CC3)c21] | 464 |
| 9 | (R)-4-(4-(1-(2-(cyclopentylamino)ethyl)-4-(trifluoromethyl)-1H-imidazol-2-yl)piperidin-1-yl)-5-methyl-5,6-dihydropyrido[2,3-d]pyrimidin-7(8H)-one | 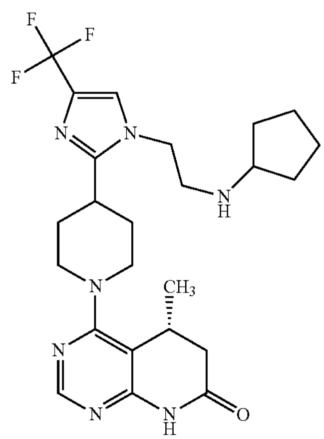 [SMILES: C[C@@H]1CC(=O)Nc2ncnc(N3CCC(c4nc(C(F)(F)F)cn4CCNC4CCCC4)CC3)c21] | 492 |
| 10 | (R)-4-(4-(1-(2-(isopropylamino)ethyl)-4-(trifluoromethyl)-1H-imidazol-2-yl)piperidin-1-yl)-5-methyl-5,6-dihydropyrido[2,3-d]pyrimidin-7(8H)-one | 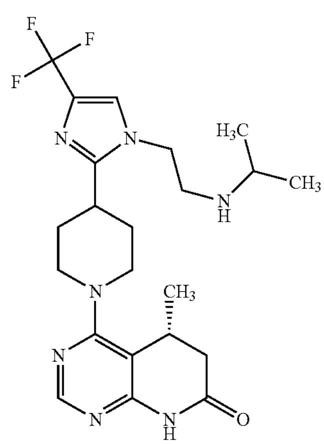 [SMILES: CC(C)NCCn1cc(C(F)(F)F)nc1C1CCN(c2ncnc3c2[C@H](C)CC(=O)N3)CC1] | 466 |

| Ex | Compound Name | Structure | MS (ES) m/z [M]+ |
|---|---|---|---|
| 11 | (R)-4-(4-(1-(2-(azetidin-1-yl)ethyl)-4-butyl-1H-imidazol-2-yl)piperidin-1-yl)-5-(trifluoromethyl)-5,6-dihydropyrido[2,3-d]pyrimidin-7(8H)-one | 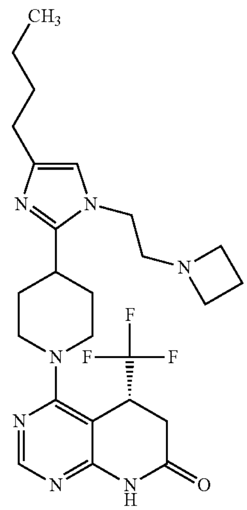 [SMILES: CCCCc1cn(CCN2CCC2)c(C2CCN(c3ncnc4c3[C@H](C(F)(F)F)CC(=O)N4)CC2)n1] | 506 |
| 12 | (R)-4-(4-(1-(2-(azetidin-1-yl)ethyl)-4-butyl-1H-imidazol-2-yl)piperidin-1-yl)-5-methyl-5,6-dihydropyrido[2,3-d]pyrimidin-7(8H)-one | 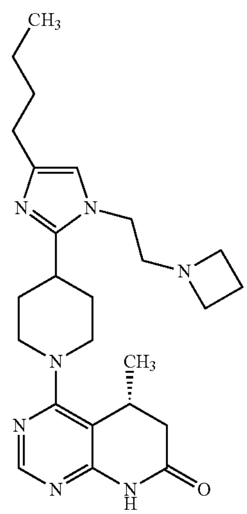 [SMILES: CCCCc1cn(CCN2CCC2)c(C2CCN(c3ncnc4c3[C@H](C)CC(=O)N4)CC2)n1] | 452 |
| 13 | (R)-5-methyl-4-(4-(4-butyl-1-(2-(pyrrolidin-1-yl)ethyl)-1H-imidazol-2-yl)piperidin-1-yl)-5,6-dihydropyrido[2,3-d]pyrimidin-7(8H)-one | 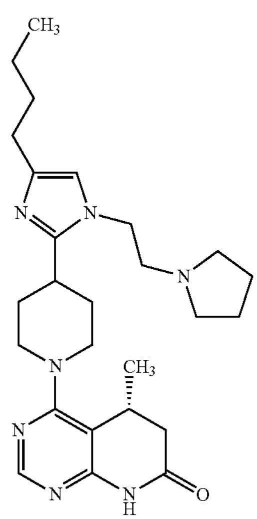 [SMILES: CCCCc1cn(CCN2CCCC2)c(C2CCN(c3ncnc4c3[C@H](C)CC(=O)N4)CC2)n1] | 466 |

-continued

| Ex | Compound Name | Structure | MS (ES) m/z [M]+ |
|---|---|---|---|
| 14 | (R)-4-(4-(1-(2-(azetidin-1-yl)ethyl)-4-propyl-1H-imidazol-2-yl)piperidin-1-yl)-5-(trifluoromethyl)-5,6-dihydropyrido[2,3-d]pyrimidin-7(8H)-one | 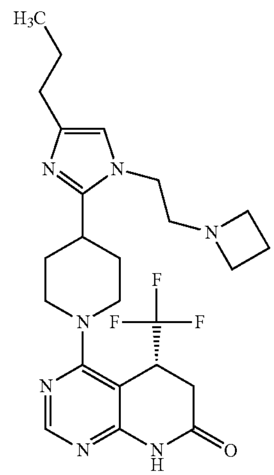 [SMILES: CCCc1cn(CCN2CCC2)c(C2CCN(c3ncnc4c3[C@H](C(F)(F)F)CC(=O)N4)CC2)n1] | 492 |
| 15 | (R)-4-(4-(1-(2-(azetidin-1-yl)ethyl)-4-ethyl-1H-imidazol-2-yl)piperidin-1-yl)-5-(trifluoromethyl)-5,6-dihydropyrido[2,3-d]pyrimidin-7(8H)-one | 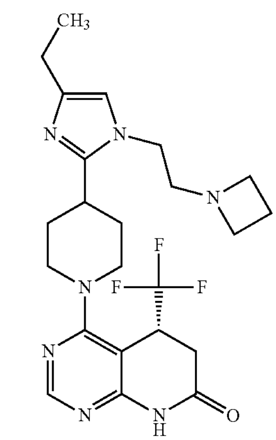 [SMILES: CCc1cn(CCN2CCC2)c(C2CCN(c3ncnc4c3[C@H](C(F)(F)F)CC(=O)N4)CC2)n1] | 478 |
| 16 | (R)-4-(4-(1-(2-(azetidin-1-yl)ethyl)-4-(tetrahydro-2H-pyran-4-yl)-1H-imidazol-2-yl)piperidin-1-yl)-5-methyl-5,6-dihydropyrido[2,3-d]pyrimidin-7(8H)-one | 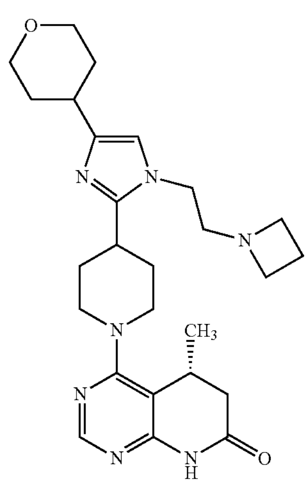 [SMILES: C[C@@H]1CC(=O)Nc2ncnc(N3CCC(c4nc(C5CCOCC5)cn4CCN4CCC4)CC3)c21] | 480 |

| Ex | Compound Name | Structure | MS (ES) m/z [M]+ |
|---|---|---|---|
| 17 | (R)-4-(4-(1-(2-(azetidin-1-yl)ethyl)-4-cyclopropyl-1H-imidazol-2-yl)piperidin-1-yl)-5-(trifluoromethyl)-5,6-dihydropyrido[2,3-d]pyrimidin-7(8H)-one | 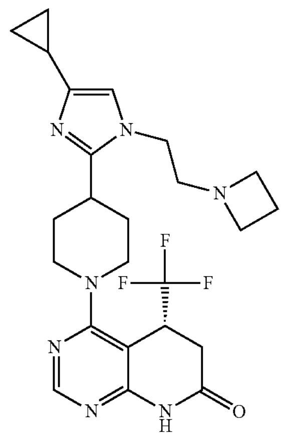 [SMILES: O=C1C[C@@H](C(F)(F)F)c2c(ncnc2N2CCC(c3nc(C4CC4)cn3CCN3CCC3)CC2)N1] | 490 |
| 18 | (R)-4-(4-(1-(2-(azetidin-1-yl)ethyl)-4-(4-methyltetrahydro-2H-pyran-4-yl)-1H-imidazol-2-yl)piperidin-1-yl)-5-(trifluoromethyl)-5,6-dihydropyrido[2,3-d]pyrimidin-7(8H)-one | 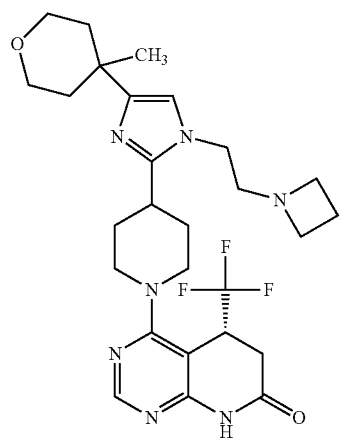 [SMILES: CC1(c2cn(CCN3CCC3)c(C3CCN(c4ncnc5c4[C@H](C(F)(F)F)CC(=O)N5)CC3)n2)CCOCC1] | 548 |
| 18a | (R)-4-(4-(1-(2-(Azetidin-1-yl)ethyl)-4-propyl-1H-imidazol-2-yl)piperidin-1-yl)-5-methyl-5,6-dihydropyrido[2,3-d]pyrimidin-7(8H)-one | 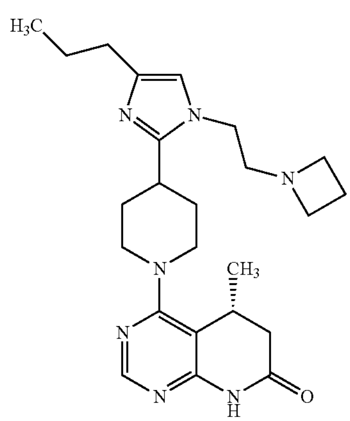 [SMILES: CCCc1cn(CCN2CCC2)c(C2CCN(c3ncnc4c3[C@H](C)CC(=O)N4)CC2)n1] | 438 |

| Ex | Compound Name | Structure | MS (ES) m/z [M]+ |
|---|---|---|---|
| 18b | (R)-4-(4-(1-(2-(Azetidin-1-yl)ethyl)-4-(2,2,2-trifluoroethyl)-1H-imidazol-2-yl)piperidin-1-yl)-5-methyl-5,6-dihydropyrido[2,3-d]pyrimidin-7(8H)-one | 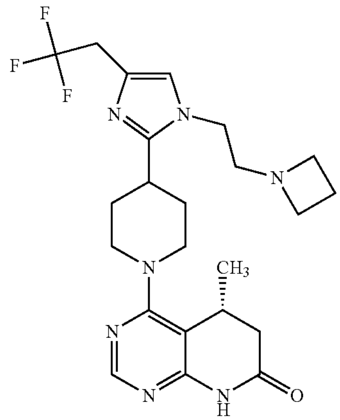 [SMILES: C[C@@H]1CC(=O)Nc2ncnc(N3CCC(c4nc(CC(F)(F)F)cn4CCN4CCC4)CC3)c21] | 478 |
| 18c | (R)-4-(4-(4-(4-Methyltetrahydro-2H-pyran-4-yl)-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 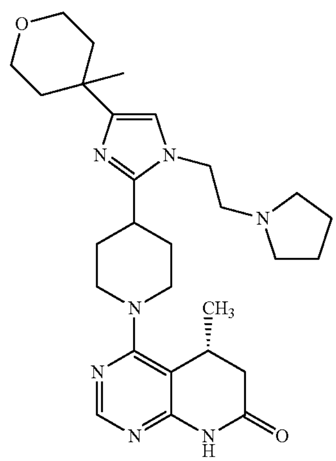 [SMILES: C[C@@H]1CC(=O)Nc2ncnc(N3CCC(c4nc(C5(C)CCOCC5)cn4CCN4CCCC4)CC3)c21] | 508 |

EXAMPLE 19

(R)-4-(4-(4-isoButyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one

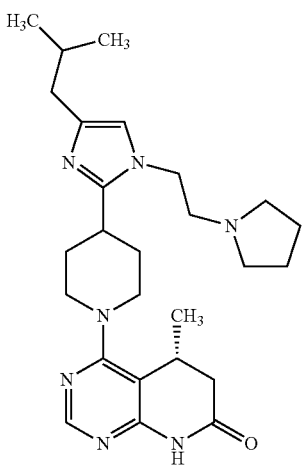 [SMILES: CC(C)Cc1cn(CCN2CCCC2)c(C2CCN(c3ncnc4c3[C@H](C)CC(=O)N4)CC2)n1]

Add (R)-4-chloro-5-methyl-5,6-dihydropyrido[2,3-d]pyrimidin-7(8H)-one (0.23 g, 1.18 mmol), 4-(4-isobutyl-1-(2-(pyrrolidin-1-yl)ethyl)-1H-imidazol-2-yl)piperidine trihydrochloride (0.64 g, 1.3 eq), N-methylpyrrolidinone (10 mL) and diisopropylethylamine (1.65 mL, 8.0 eq) in a microwave tube. Seal with crimp cap. Heat in a microwave reactor at 200° C. for 40 minutes. Dilute the reaction mixture with water and extract with ethyl acetate. Wash with saturated aqueous sodium chloride. Dry the organics over anhydrous magnesium sulfate, filter, and concentrate in vacuo. Purify by normal phase chromatography, eluting with hexanes to ethyl acetate to 5% methanol/ethyl acetate to 3% to 5% to 7% to 10% methanol/dichloromethane, to give the title compound (0.13 g, 23%). MS (ES) m/z=466 [M]+.

Prepare the following compounds essentially as described for (R)-4-(4-(4-(4-isobutyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one (alternative purification; treat the free base with 4 M hydrochloric acid in 1,4-dioxane, then concentrate in vacuo to afford the dihydrochloride salt. A second alternative is to further purify the free base with acidic reverse phase chromatography; concentrate clean fractions in vacuo to afford the dihydrochloride or trifluoroacetate salt.):

| Ex | Compound Name | Structure | MS (ES) m/z [M]+ |
|---|---|---|---|
| 20 | (R)-5-methyl-4-(4-(4-propyl-1-(2-(pyrrolidin-1-yl)ethyl)-1H-imidazol-2-yl)piperidin-1-yl)-5,6-dihydropyrido[2,3-d]pyrimidin-7(8H)-one | 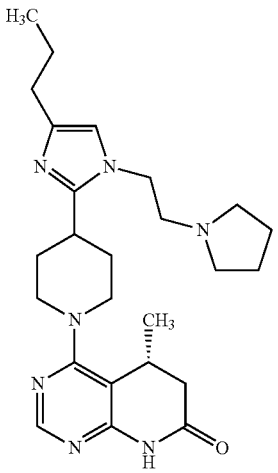 [SMILES: CCCc1cn(CCN2CCCC2)c(C2CCN(c3ncnc4c3[C@H](C)CC(=O)N4)CC2)n1] | 452 |
| 21 | (R)-4-(4-(4-methyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 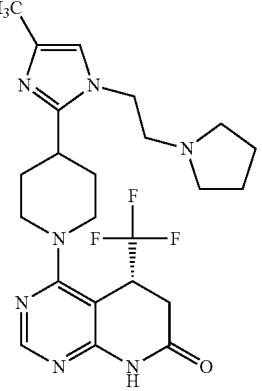 | 478 |
| 22 | (R)-5-methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one; 2,2,2-trifluoroacetic acid | 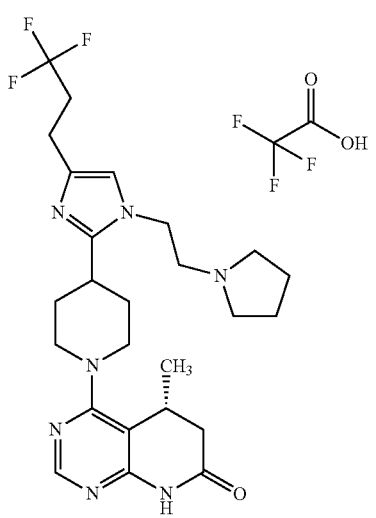 [SMILES: C[C@@H]1CC(=O)Nc2ncnc(N3CCC(c4nc(CCC(F)(F)F)cn4CCN4CCCC4)CC3)c21 ; O=C(O)C(F)(F)F] | 506 |

| Ex | Compound Name | Structure | MS (ES) m/z [M]+ |
|---|---|---|---|
| 23 | (R)-4-(4-(4-(1-methylcyclobutyl)-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 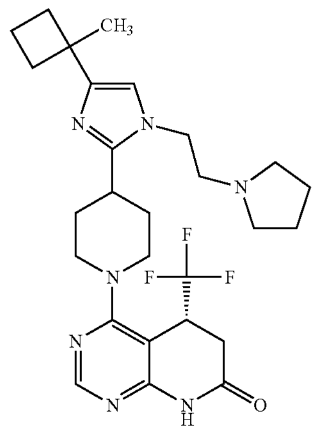 [SMILES: CC1(c2cn(CCN3CCCC3)c(C3CCN(c4ncnc5c4[C@H](C(F)(F)F)CC(=O)N5)CC3)n2)CCC1] | 532 |
| 24 | (R)-5-methyl-4-(4-(4-(1-methylcyclobutyl)-1-(2-(pyrrolidin-1-yl)ethyl)-1H-imidazol-2-yl)piperidin-1-yl)-5,6-dihydropyrido[2,3-d]pyrimidin-7(8H)-one | 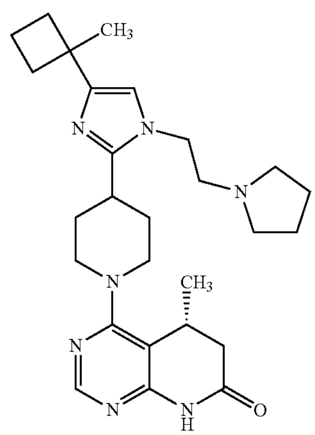 [SMILES: C[C@@H]1CC(=O)Nc2ncnc(N3CCC(c4nc(C5(C)CCC5)cn4CCN4CCCC4)CC3)c21] | 478 |
| 25 | (R)-4-(4-(4-(2-methoxyethyl)-1-(2-(pyrrolidin-1-yl)ethyl)-1H-imidazol-2-yl)piperidin-1-yl)-5-methyl-5,6-dihydropyrido[2,3-d]pyrimidin-7(8H)-one; 2,2,2-trifluoroacetic acid | 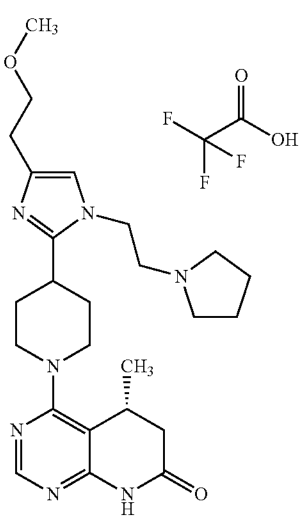 [SMILES: COCCc1cn(CCN2CCCC2)c(C2CCN(c3ncnc4c3[C@H](C)CC(=O)N4)CC2)n1 ; O=C(O)C(F)(F)F] | 468 |

-continued

| Ex | Compound Name | Structure | MS (ES) m/z [M]+ |
|---|---|---|---|
| 26 | (R)-4-(4-(4-ethyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 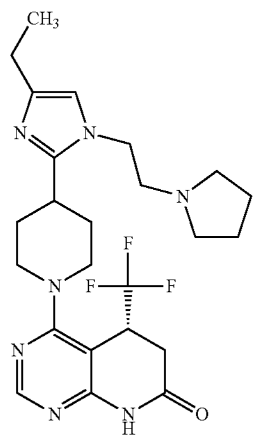 [SMILES: CCc1cn(CCN2CCCC2)c(C2CCN(c3ncnc4c3[C@H](C(F)(F)F)CC(=O)N4)CC2)n1] | 492 |
| 27 | (R)-4-(4-(4-cyclobutyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 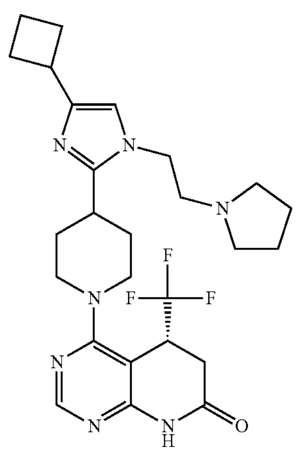 [SMILES: O=C1C[C@@H](C(F)(F)F)c2c(ncnc2N2CCC(c3nc(C4CCC4)cn3CCN3CCCC3)CC2)N1] | 518 |
| 28 | (R)-4-(4-(1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 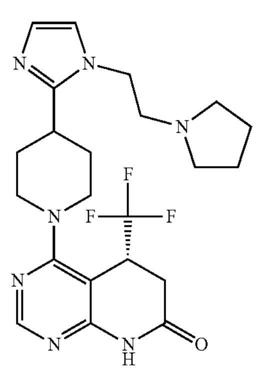 [SMILES: O=C1C[C@@H](C(F)(F)F)c2c(ncnc2N2CCC(c3nccn3CCN3CCCC3)CC2)N1] | 464 |

-continued

| Ex | Compound Name | Structure | MS (ES) m/z [M]+ |
|---|---|---|---|
| 29 | (R)-4-(4-(1-(2-(cyclopentylamino)ethyl)-4-ethyl-1H-imidazol-2-yl)piperidin-1-yl)-5-(trifluoromethyl)-5,6-dihydropyrido[2,3-d]pyrimidin-7(8H)-one | 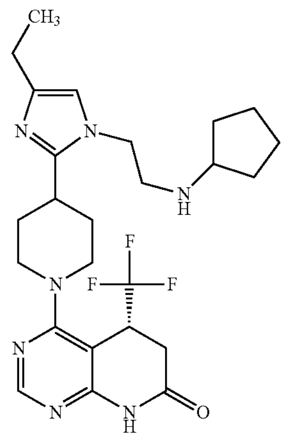 [SMILES: CCc1cn(CCNC2CCCC2)c(C2CCN(c3ncnc4c3[C@H](C(F)(F)F)CC(=O)N4)CC2)n1] | 506 |
| 30 | (R)-4-(4-(4-(1-methylcyclopropyl)-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 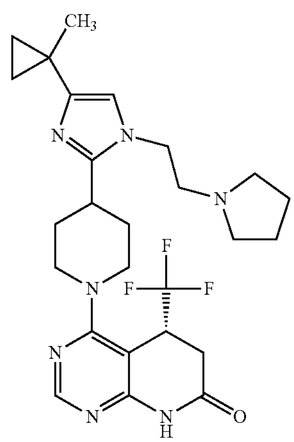 [SMILES: CC1(c2cn(CCN3CCCC3)c(C3CCN(c4ncnc5c4[C@H](C(F)(F)F)CC(=O)N5)CC3)n2)CC1] | 518 |
| 31 | (R)-4-(4-(1-(2-(tert-butylamino)ethyl)-4-cyclopentyl-1H-imidazol-2-yl)piperidin-1-yl)-5-(trifluoromethyl)-5,6-dihydropyrido[2,3-d]pyrimidin-7(8H)-one | 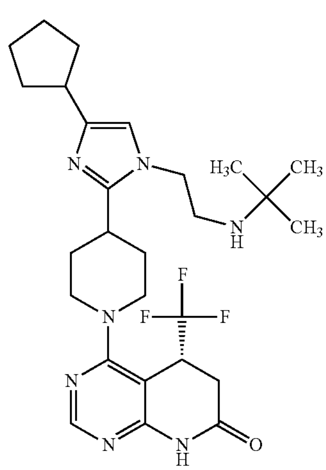 [SMILES: CC(C)(C)NCCn1cc(C2CCCC2)nc1C1CCN(c2ncnc3c2[C@H](C(F)(F)F)CC(=O)N3)CC1] | 534 |

-continued

| Ex | Compound Name | Structure | MS (ES) m/z [M]+ |
|---|---|---|---|
| 32 | (R)-4-(4-(1-(2-(tert-butylamino)ethyl)-4-(trifluoromethyl)-1H-imidazol-2-yl)piperidin-1-yl)-5-(trifluoromethyl)-5,6-dihydropyrido[2,3-d]pyrimidin-7(8H)-one | 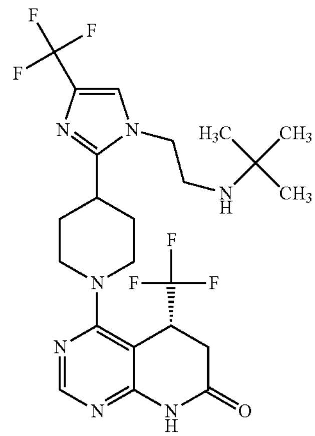 [SMILES: CC(C)(C)NCCn1cc(C(F)(F)F)nc1C1CCN(c2ncnc3c2[C@H](C(F)(F)F)CC(=O)N3)CC1] | 534 |
| 33 | (R)-4-(4-(1-(2-(pyrrolidin-1-yl)ethyl)-4-(tetrahydro-2H-pyran-4-yl)-1H-imidazol-2-yl)piperidin-1-yl)-5-(trifluoromethyl)-5,6-dihydropyrido[2,3-d]pyrimidin-7(8H)-one | 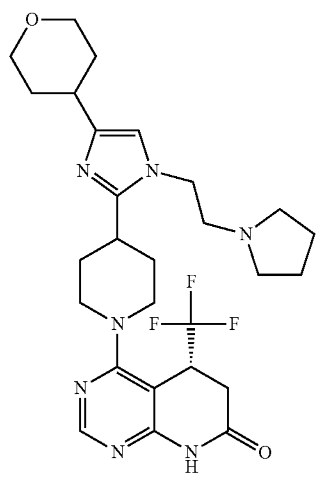 [SMILES: O=C1C[C@@H](C(F)(F)F)c2c(ncnc2N2CCC(c3nc(C4CCOCC4)cn3CCN3CCCC3)CC2)N1] | 548 |
| 34 | (R)-4-(4-(1-(2-(tert-butylamino)ethyl)-4-(tetrahydro-2H-pyran-4-yl)-1H-imidazol-2-yl)piperidin-1-yl)-5-methyl-5,6-dihydropyrido[2,3-d]pyrimidin-7(8H)-one | 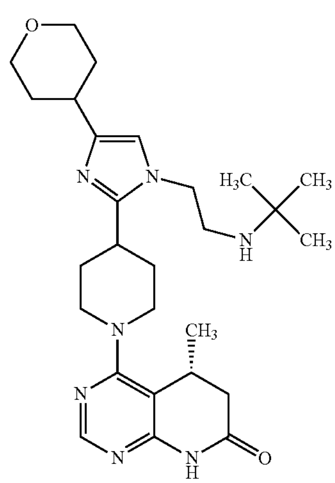 [SMILES: C[C@@H]1CC(=O)Nc2ncnc(N3CCC(c4nc(C5CCOCC5)cn4CCNC(C)(C)C)CC3)c21] | 496 |

-continued

| Ex | Compound Name | Structure | MS (ES) m/z [M]+ |
|---|---|---|---|
| 35 | (R)-4-(4-(1-(2-(tert-butylamino)ethyl)-4-(2,2,2-trifluoroethyl)imidazol-2-yl)-1-piperidyl)-5-methyl-6,8-dihydro-5H-pyrido[2,3-d]pyrimidin-7-one dihydrochloride | 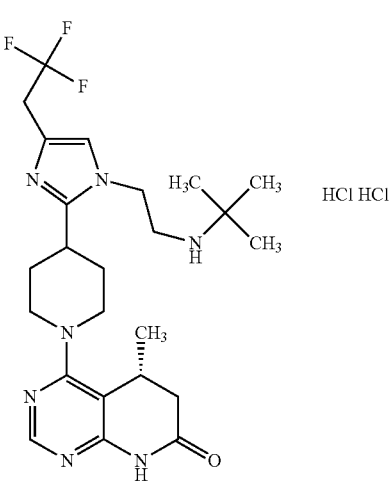 [SMILES: C[C@@H]1CC(=O)Nc2ncnc(N3CCC(c4nc(CC(F)(F)F)cn4CCNC(C)(C)C)CC3)c21 ; "HCl HCl"] | 494 |
| 36 | (R)-4-(4-(1-(2-(tert-butylamino)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one | 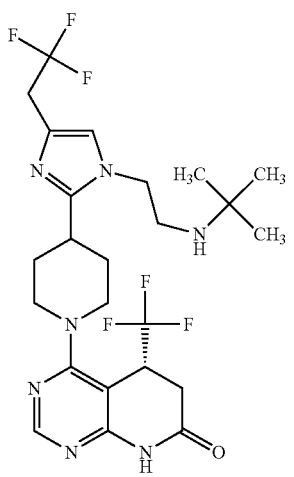 [SMILES: CC(C)(C)NCCn1cc(CC(F)(F)F)nc1C1CCN(c2ncnc3c2[C@H](C(F)(F)F)CC(=O)N3)CC1] | 548 |
| 37 | (R)-4-(4-(1-(2-(tert-butylamino)ethyl)-4-(tetrahydro-2H-pyran-4-yl)-1H-imidazol-2-yl)piperidin-1-yl)-5-(trifluoromethyl)-5,6-dihydropyrido[2,3-d]pyrimidin-7(8H)-one | 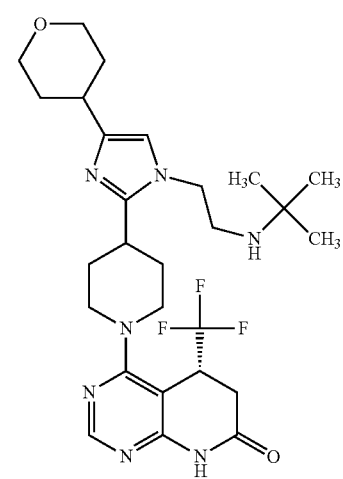 [SMILES: CC(C)(C)NCCn1cc(C2CCOCC2)nc1C1CCN(c2ncnc3c2[C@H](C(F)(F)F)CC(=O)N3)CC1] | 550 |

| Ex | Compound Name | Structure | MS (ES) m/z [M]+ |
|---|---|---|---|
| 38 | (R)-4-(4-(1-(2-(tert-butylamino)ethyl)-4-ethyl-1H-imidazol-2-yl)piperidin-1-yl)-5-methyl-5,6-dihydropyrido[2,3-d]pyrimidin-7(8H)-one | 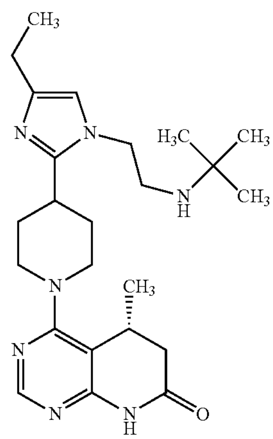 [SMILES: CCc1cn(CCNC(C)(C)C)c(C2CCN(c3ncnc4c3[C@H](C)CC(=O)N4)CC2)n1] | 440 |
| 39 | (R)-4-(4-(1-(2-(tert-butylamino)ethyl)-4-cyclopropyl-1H-imidazol-2-yl)piperidin-1-yl)-5-(trifluoromethyl)-5,6-dihydropyrido[2,3-d]pyrimidin-7(8H)-one | 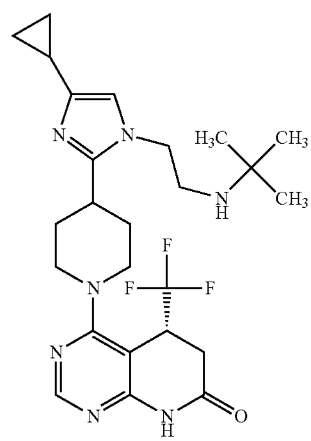 [SMILES: CC(C)(C)NCCn1cc(C2CC2)nc1C1CCN(c2ncnc3c2[C@H](C(F)(F)F)CC(=O)N3)CC1] | 506 |
| 40 | (R)-4-(4-(1-(2-(tert-butylamino)ethyl)-4-isopropyl-1H-imidazol-2-yl)piperidin-1-yl)-5-(trifluoromethyl)-5,6-dihydropyrido[2,3-d]pyrimidin-7(8H)-one | 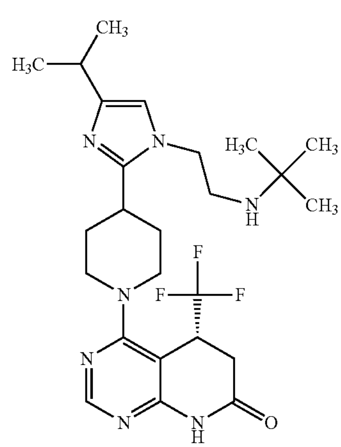 [SMILES: CC(C)c1cn(CCNC(C)(C)C)c(C2CCN(c3ncnc4c3[C@H](C(F)(F)F)CC(=O)N4)CC2)n1] | 508 |

| Ex | Compound Name | Structure | MS (ES) m/z [M]+ |
|---|---|---|---|
| 41 | (R)-4-(4-(4-chloro-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 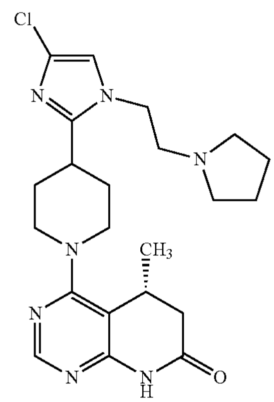 [SMILES: C[C@@H]1CC(=O)Nc2ncnc(N3CCC(c4nc(Cl)cn4CCN4CCCC4)CC3)c21] | 444 |
| 42 | (R)-5-ethyl-4-(4-(4-ethyl-1-(2-(pyrrolidin-1-yl)ethyl)-1H-imidazol-2-yl)piperidin-1-yl)-5,6-dihydropyrido[2,3-d]pyrimidin-7(8H)-one | 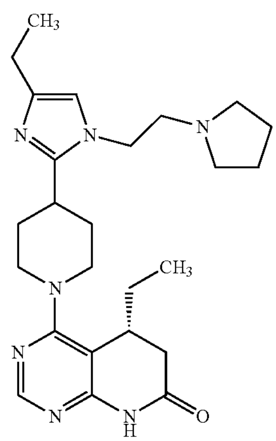 [SMILES: CCc1cn(CCN2CCCC2)c(C2CCN(c3ncnc4c3[C@H](CC)CC(=O)N4)CC2)n1] | 452 |
| 43 | (R)-4-(4-(1-(2-(tert-butylamino)ethyl)-4-cyclopropyl-1H-imidazol-2-yl)piperidin-1-yl)-5-methyl-5,6-dihydropyrido[2,3-d]pyrimidin-7(8H)-one dihydrochloride | 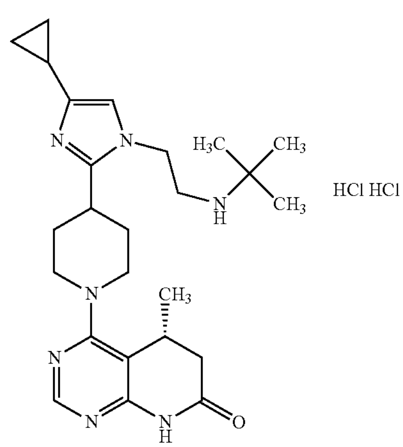 [SMILES: C[C@@H]1CC(=O)Nc2ncnc(N3CCC(c4nc(C5CC5)cn4CCNC(C)(C)C)CC3)c21 ; "HCl HCl"] | 452 |

-continued

| Ex | Compound Name | Structure | MS (ES) m/z [M]+ |
|---|---|---|---|
| 44 | (R)-4-(4-(4-(1-methoxy-2-methylpropan-2-yl)-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 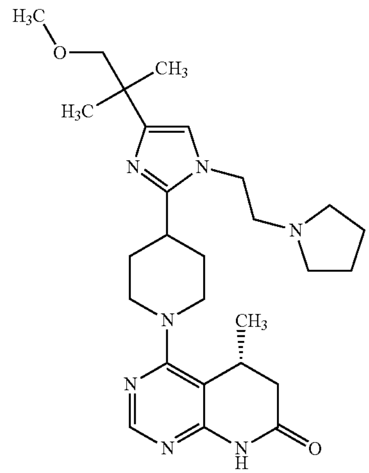 [SMILES: COCC(C)(C)c1cn(CCN2CCCC2)c(C2CCN(c3ncnc4c3[C@H](C)CC(=O)N4)CC2)n1] | 496 |
| 45 | 5-(4-(4-cyclopentyl-1-(2-(pyrrolidin-1-yl)ethyl)-1H-imidazol-2-yl)piperidin-1-yl)-3-(2,2,2-trifluoroethyl)-3,4-dihydropyrimido[4,5-d]pyrimidin-2(1H)-one | 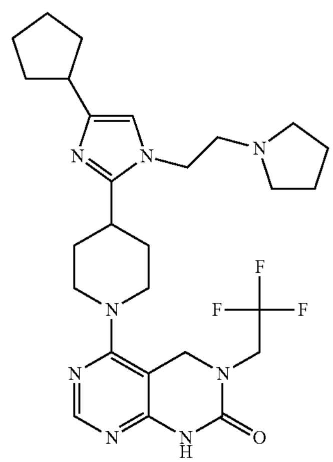 [SMILES: O=C1Nc2ncnc(N3CCC(c4nc(C5CCCC5)cn4CCN4CCCC4)CC3)c2CN1CC(F)(F)F] | 547 |
| 46 | (R)-4-(4-(4-cyclopentyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 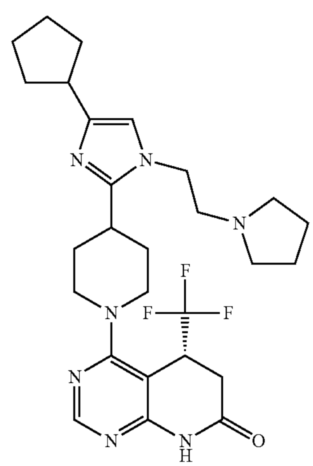 [SMILES: O=C1C[C@@H](C(F)(F)F)c2c(ncnc2N2CCC(c3nc(C4CCCC4)cn3CCN3CCCC3)CC2)N1] | 532 |

| Ex | Compound Name | Structure | MS (ES) m/z [M]+ |
|---|---|---|---|
| 47 | (R)-4-(4-(4-cyclohexyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 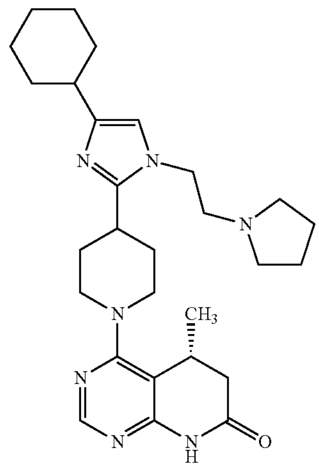 [SMILES: C[C@@H]1CC(=O)Nc2ncnc(N3CCC(c4nc(C5CCCCC5)cn4CCN4CCCC4)CC3)c21] | 492 |
| 48 | (R)-4-(4-(4-ethyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one dihydrochloride | 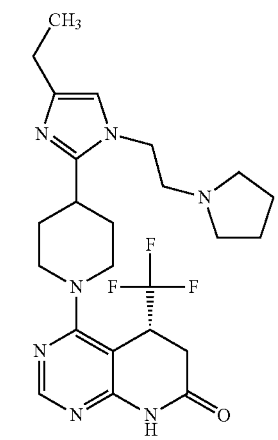 | 492 |
| 49 | (R)-5-methyl-4-(4-(4-(1-methylcyclopropyl)-1-(2-(pyrrolidin-1-yl)ethyl)-1H-imidazol-2-yl)piperidin-1-yl)-5,6-dihydropyrido[2,3-d]pyrimidin-7(8H)-one | 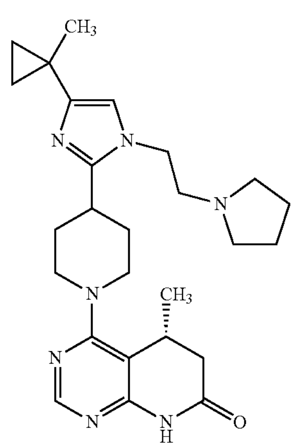 [SMILES: C[C@@H]1CC(=O)Nc2ncnc(N3CCC(c4nc(C5(C)CC5)cn4CCN4CCCC4)CC3)c21] | 464 |

-continued

| Ex | Compound Name | Structure | MS (ES) m/z [M]+ |
|---|---|---|---|
| 50 | (R)-4-(4-(1-(2-(pyrrolidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one | 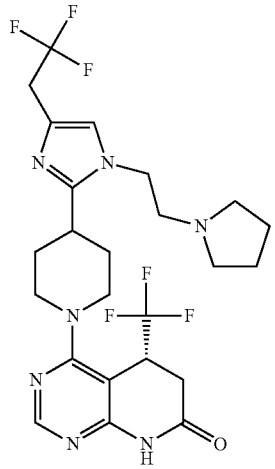 [SMILES: O=C1C[C@@H](C(F)(F)F)c2c(ncnc2N2CCC(c3nc(CC(F)(F)F)cn3CCN3CCCC3)CC2)N1] | 546 |
| 51 | (R)-4-(4-(1-(2-(tert-butylamino)ethyl)-4-isopropyl-1H-imidazol-2-yl)piperidin-1-yl)-5-methyl-5,6-dihydropyrido[2,3-d]pyrimidin-7(8H)-one dihydrochloride | 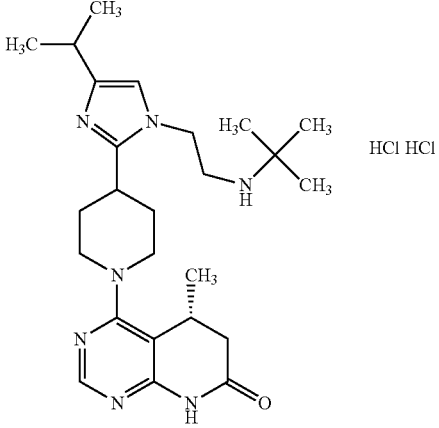 [SMILES: CC(C)c1cn(CCNC(C)(C)C)c(C2CCN(c3ncnc4c3[C@H](C)CC(=O)N4)CC2)n1 ; "HCl HCl"] | 454 |
| 52 | (R)-4-(4-(4-isopropyl-1-(2-(isopropylamino)ethyl)-1H-imidazol-2-yl)piperidin-1-yl)-5-methyl-5,6-dihydropyrido[2,3-d]pyrimidin-7(8H)-one dihydrochloride | 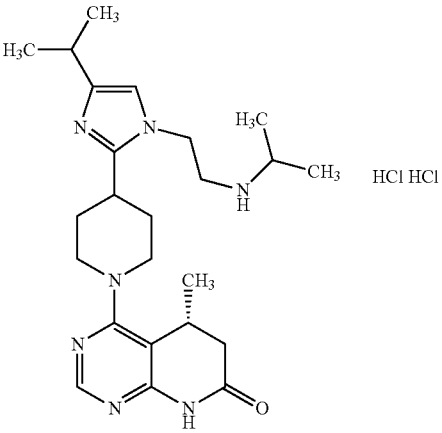 [SMILES: CC(C)NCCn1cc(C(C)C)nc1C1CCN(c2ncnc3c2[C@H](C)CC(=O)N3)CC1 ; "HCl HCl"] | 440 |

| Ex | Compound Name | Structure | MS (ES) m/z [M]+ |
|---|---|---|---|
| 53 | (R)-4-(4-(4-cyclopropyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 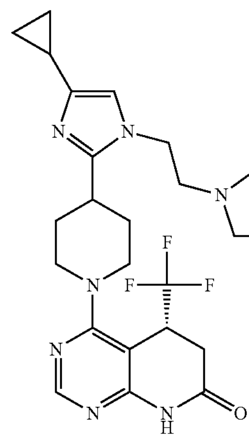 | 504 |
| 54 | (R)-4-(4-(4-cyclobutyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 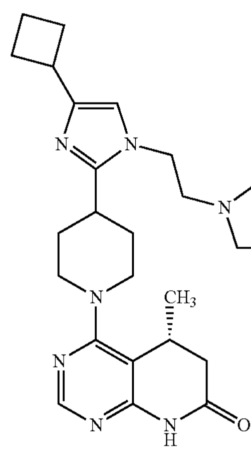 | 464 |
| 55 | (R)-4-(4-(4-isopropyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 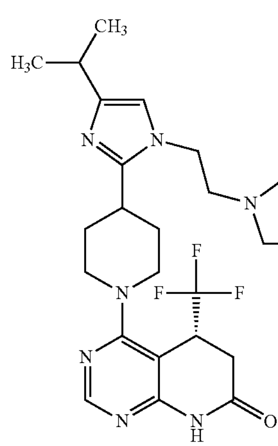 | 506 |

-continued

| Ex | Compound Name | Structure | MS (ES) m/z [M]+ |
|---|---|---|---|
| 56 | (R)-4-(4-(4,5-dichloro-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 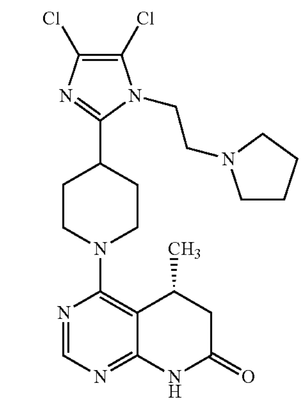 [SMILES: C[C@@H]1CC(=O)Nc2ncnc(N3CCC(c4nc(Cl)c(Cl)n4CCN4CCCC4)CC3)c21] | 479 |
| 57 | 5-(4-(4-isopropyl-1-(2-(pyrrolidin-1-yl)ethyl)-1H-imidazol-2-yl)piperidin-1-yl)-3-(2,2,2-trifluoroethyl)-3,4-dihydropyrimido[4,5-d]pyrimidin-2(1H)-one | 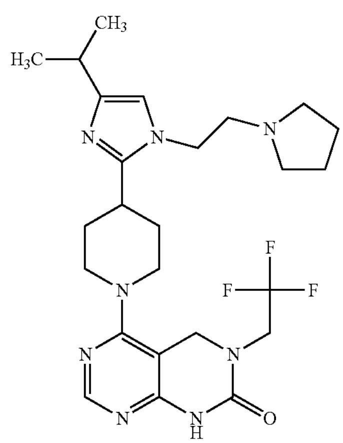 [SMILES: CC(C)c1cn(CCN2CCCC2)c(C2CCN(c3ncnc4c3CN(CC(F)(F)F)C(=O)N4)CC2)n1] | 521 |
| 58 | (R)-4-(4-(1-(2-(cyclobutylamino)ethyl)-4-(trifluoromethyl)-1H-imidazol-2-yl)piperidin-1-yl)-5-methyl-5,6-dihydropyrido[2,3-d]pyrimidin-7(8H)-one | 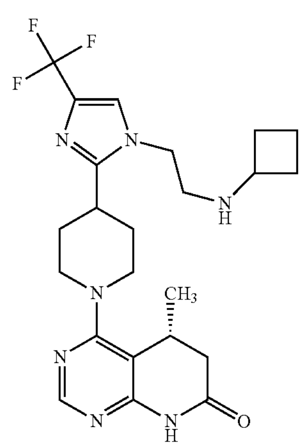 [SMILES: C[C@@H]1CC(=O)Nc2ncnc(N3CCC(c4nc(C(F)(F)F)cn4CCNC4CCC4)CC3)c21] | 478 |

-continued

| Ex | Compound Name | Structure | MS (ES) m/z [M]+ |
|---|---|---|---|
| 59 | (R)-4-(4-(4-bromo-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 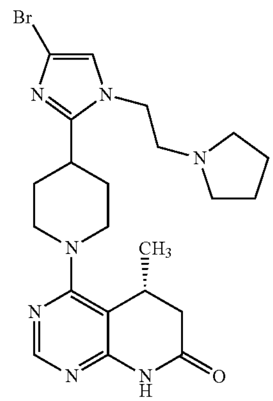 | 488 |
| 60 | (R)-5-methyl-4-(4-(1-(2-(pyrrolidin-1-yl)ethyl)-4-vinyl-1H-imidazol-2-yl)piperidin-1-yl)-5,6-dihydropyrido[2,3-d]pyrimidin-7(8H)-one | 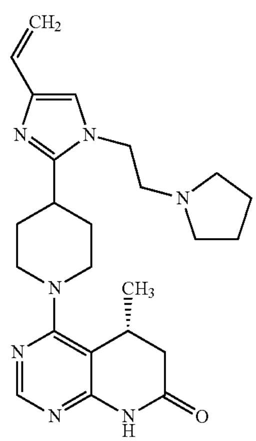 [SMILES: C=Cc1cn(CCN2CCCC2)c(C2CCN(c3ncnc4c3[C@H](C)CC(=O)N4)CC2)n1] | 436 |
| 61 | (R)-2-(1-(5-methyl-7-oxo-5,6,7,8-tetrahydropyrido[2,3-d]pyrimidin-4-yl)piperidin-4-yl)-1-(2-(pyrrolidin-1-yl)ethyl)-1H-imidazole-4-carbonitrile | 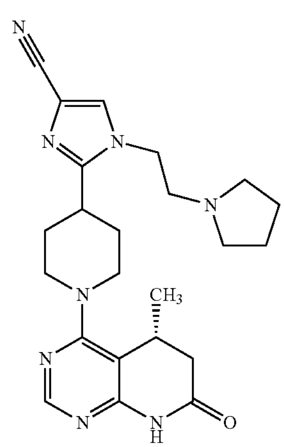 [SMILES: C[C@@H]1CC(=O)Nc2ncnc(N3CCC(c4nc(C#N)cn4CCN4CCCC4)CC3)c21] | 435 |

-continued

| Ex | Compound Name | Structure | MS (ES) m/z [M]+ |
|---|---|---|---|
| 62 | (R)-4-(4-(4-cyclopentyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 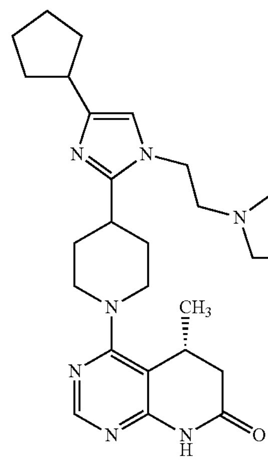 | 478 |
| 63 | (R)-4-(4-(4-cyclopropyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 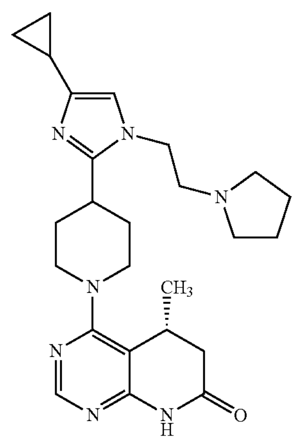 [SMILES: C[C@@H]1CC(=O)Nc2ncnc(N3CCC(c4nc(C5CC5)cn4CCN4CCCC4)CC3)c21] | 450 |
| 64 | (R)-5-methyl-4-(4-(1-(2-(pyrrolidin-1-yl)ethyl)-4-(2,2,2-trifluoroethyl)-1H-imidazol-2-yl)piperidin-1-yl)-5,6-dihydropyrido[2,3-d]pyrimidin-7(8H)-one | 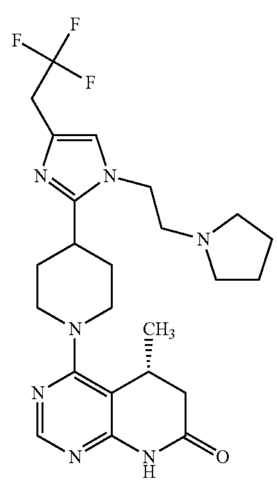 [SMILES: C[C@@H]1CC(=O)Nc2ncnc(N3CCC(c4nc(CC(F)(F)F)cn4CCN4CCCC4)CC3)c21] | 492 |

-continued

| Ex | Compound Name | Structure | MS (ES) m/z [M]+ |
|---|---|---|---|
| 65 | (R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 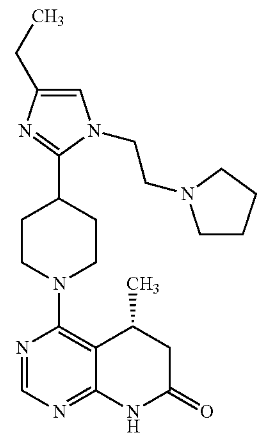 [SMILES: CCc1cn(CCN2CCCC2)c(C2CCN(c3ncnc4c3[C@H](C)CC(=O)N4)CC2)n1] | 438 |
| 66 | (R)-4-(4-(4-tert-butyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 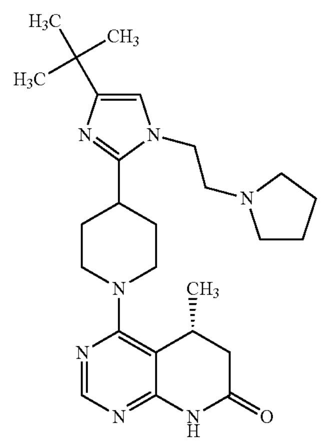 [SMILES: C[C@@H]1CC(=O)Nc2ncnc(N3CCC(c4nc(C(C)(C)C)cn4CCN4CCCC4)CC3)c21] | 466 |
| 67 | (R)-4-(4-(4-isopropyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one | 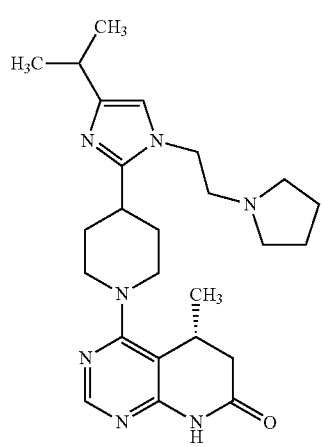 [SMILES: CC(C)c1cn(CCN2CCCC2)c(C2CCN(c3ncnc4c3[C@H](C)CC(=O)N4)CC2)n1] | 452 |

-continued

| Ex | Compound Name | Structure | MS (ES) m/z [M]+ |
|---|---|---|---|
| 68 | (R)-4-(4-(1-(2-(pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7(8H)-one | 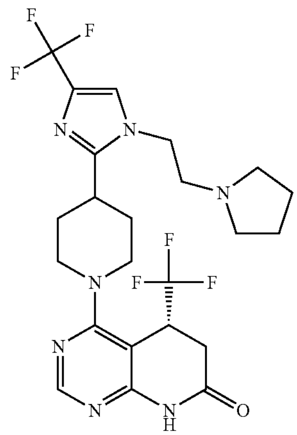 [SMILES: O=C1C[C@@H](C(F)(F)F)c2c(ncnc2N2CCC(c3nc(C(F)(F)F)cn3CCN3CCCC3)CC2)N1] | 532 |
| 69 | (R)-4-(4-(4-butyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 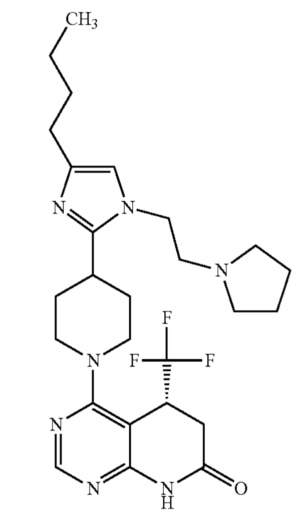 [SMILES: CCCCc1cn(CCN2CCCC2)c(C2CCN(c3ncnc4c3[C@H](C(F)(F)F)CC(=O)N4)CC2)n1] | 520 |
| 70 | (R)-4-(4-(4-propyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one | 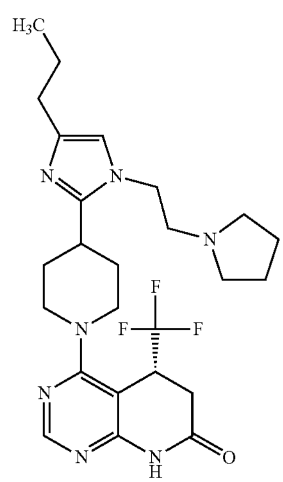 [SMILES: CCCc1cn(CCN2CCCC2)c(C2CCN(c3ncnc4c3[C@H](C(F)(F)F)CC(=O)N4)CC2)n1] | 506 |

| Ex | Compound Name | Structure | MS (ES) m/z [M]+ |
|---|---|---|---|
| 71 | (R)-4-(4-(4-ethyl-1-(2-(tetrahydro-2H-pyran-4-ylamino)ethyl)-1H-imidazol-2-yl)piperidin-1-yl)-5-methyl-5,6-dihydropyrido[2,3-d]pyrimidin-7(8H)-one | 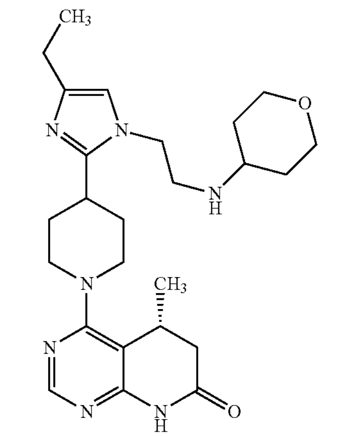 [SMILES: CCc1cn(CCNC2CCOCC2)c(C2CCN(c3ncnc4c3[C@H](C)CC(=O)N4)CC2)n1] | 468 |
| 72 | (R)-4-(4-(1-(2-(pyrrolidin-1-yl)ethyl)-4-(tetrahydro-2H-pyran-4-yl)-1H-imidazol-2-yl)piperidin-1-yl)-5-ethyl-5,6-dihydropyrido[2,3-d]pyrimidin-7(8H)-one | 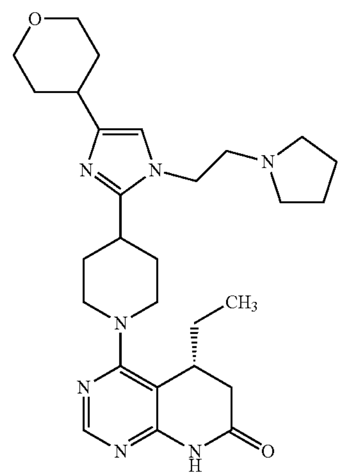 [SMILES: CC[C@@H]1CC(=O)Nc2ncnc(N3CCC(c4nc(C5CCOCC5)cn4CCN4CCCC4)CC3)c21] | 508 |

EXAMPLE 73

(R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one

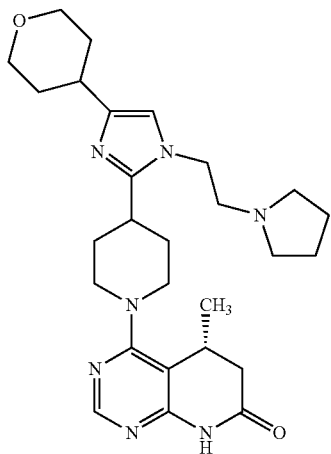 [SMILES: C[C@@H]1CC(=O)Nc2ncnc(N3CCC(c4nc(C5CCOCC5)cn4CCN4CCCC4)CC3)c21]

Charge 4-(1-(2-(Pyrrolidin-1-yl)ethyl)-4-(tetrahydro-2H-pyran-4-yl)-1H-imidazol-2-yl)piperidine trihydrochloride (300 g, 1.0 equiv), (R)-4-Chloro-5-methyl-5,6-dihydropyrido[2,3-d]pyrimidin-7(8H)-one (146.2 g, 1.0 equiv) and n-propanol (3.0 L) to a 12-L reaction flask. Stir the reaction mixture and add 1,8-diazabicyclo[5.4.0]undec-7-ene (394.3 g, 3.5 equiv) over ten minutes. Heat the reaction to 90° C. for 8 hours, and allow to cool to room temperature over 12 hours. Displace the n-propanol with n-butyl acetate to a total volume of 3-L and a residual n-propanol content of 11% (w/w). Heat the organic solution to 50-60° C. and wash with brine (2.25 L). Back-extract the aqueous phase with nButyl acetate (1.5 L) and combine the organic layers. Wash the combined organic layers with water (2×450 mL) at 50-60° C. Separate the organic layer and add activated charcoal (75 g, 0.25 equiv) and stir at 50-60° C. for 30 min. Filter the slurry and rinse the solids with n butyl acetate (1.5 L). Wash with water (1 L), separate the organic phase and azeotropically dry the organic phase to remove water. At 50-60° C., add heptanes (3.0 L) cool to 40° C. and add seed crystals. Allow the slurry to cool to room temperature over ~12 h. Cool to 0-5° C., filter the slurry and wash with heptanes (2×900 mL). Dry in vacuo and isolate (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one as a white solid (365.3 g, 64%). MS (ES) m/z=494 [M]+.

EXAMPLES 74 AND 75

4-(4-(1-(2-(Pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7(8H)-one and (R)-4-(4-(1-(2-(Pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7(8H)-one

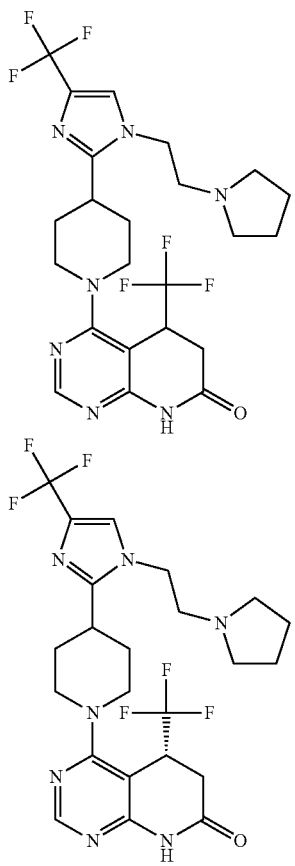

Combine 4-chloro-8-(2,4-dimethoxybenzyl)-5-(trifluoromethyl)-5,6-dihydropyrido[2,3-d]pyrimidin-7(8H)-one (0.65 g, 1.62 mmol), 4-(1-(2-(pyrrolidin-1-yl)ethyl)-4-(trifluoromethyl)-1H-imidazol-2-yl)piperidine trihydrochloride (0.76 g, 1.1 eq), N-methylpyrrolidinone (20 mL) and diisopropylethylamine (1.69 mL, 6.0 eq) in a sealed vessel. Heat at 220° C. for 30 minutes. Dilute the reaction mixture with water and extract with ethyl acetate. Wash the organics with saturated aqueous sodium chloride. Dry the organics over anhydrous sodium sulfate, filter, and concentrate in vacuo. Purify by normal phase chromatography, eluting with a 1-10% methanol/dichloromethane gradient, to give crude 8-(2,4-dimethoxybenzyl)-4-(4-(1-(2-(pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7(8H)-one (crude).

Combine the crude protected intermediate (1.10 g, theoretical) and trifluoroacetic acid (5.00 mL, 41 eq) in a microwave tube. Seal the tube and heat in a microwave reactor at 100° C. for ten minutes. Concentrate in vacuo. Dilute the reaction mixture with water and extract with ethyl acetate. Wash the organics with saturated aqueous sodium chloride. Dry the organics over anhydrous sodium sulfate, filter, and concentrate in vacuo. Purify by normal phase chromatography, eluting with a 5-20% methanol/dichloromethane gradient, to give 4-(4-(1-(2-(pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7 (8H)-one as a racemate (0.70 g, 82%). MS (ES) m/z=532 $[M]^+$.

Chiral separation (Chiralpak AD-H, 30% ethanol/70% $CO_2$ w/0.2% isopropylamine) provides enantiomer 1 (>99% ee) and (R)-4-(4-(1-(2-(pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7(8H)-one as enantiomer 2 (>99% ee). MS (ES) m/z=532 $[M]^+$ for both compounds.

EXAMPLES 76 AND 77

5-Methyl-4-(4-(1-(2-(pyrrolidin-1-yl)ethyl)-4-(trifluoromethyl)-1H-imidazol-2-yl)piperidin-1-yl)-5,6-dihydropyrido[2,3-d]pyrimidin-7(8H)-one and (R)-5-Methyl-4-(4-(1-(2-(pyrrolidin-1-yl)ethyl)-4-(trifluoromethyl)-1H-imidazol-2-yl)piperidin-1-yl)-5,6-dihydropyrido[2,3-d]pyrimidin-7(8H)-one

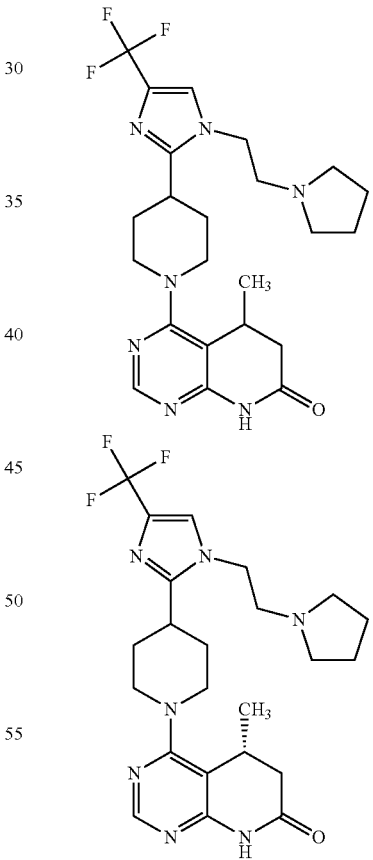

Add 4-chloro-5-methyl-5,6-dihydropyrido[2,3-d]pyrimidin-7(8H)-one (0.22 g, 1.11 mmol), 4-(1-(2-(pyrrolidin-1-yl)ethyl)-4-(trifluoromethyl)-1H-imidazol-2-yl)piperidine trihydrochloride (0.57 g, 1.2 eq), N-methylpyrrolidinone (10 mL) and diisopropylethylamine (1.16 mL, 6.0 eq) in a microwave tube. Seal the tube and heat in a microwave reactor at 200° C. for 30 minutes. Dilute the reaction mixture with water and extract with ethyl acetate. Wash with saturated aqueous sodium chloride. Dry the organics over anhydrous sodium sulfate, filter, and concentrate in vacuo. Purify by normal phase chromatography, eluting with a 1-10% methanol/dichloromethane gradient, to give 5-methyl-4-(4-(1-(2-(pyrrolidin-1-yl)ethyl)-4-(trifluoromethyl)-1H-imidazol-2-yl)piperidin-1-yl)-5,6-dihydropyrido[2,3-d]pyrimidin-7(8H)-one as a racemate (0.19 g, 36%). MS (ES) m/z=478 [M]$^+$. Chiral separation (Chiralpak AD-H, 30% ethanol/70% $CO_2$ w/0.2% isopropylamine) provides enantiomer 1 (>99% ee) and (R)-5-methyl-4-(4-(1-(2-(pyrrolidin-1-yl)ethyl)-4-(trifluoromethyl)-1H-imidazol-2-yl)piperidin-1-yl)-5,6-dihydropyrido[2,3-d]pyrimidin-7(8H)-one as enantiomer 2 (>99% ee). MS (ES) m/z=478 [M]$^+$ for both compounds.

EXAMPLE 78

(R)-5-Methyl-4-(4-(1-(2-(pyrrolidin-1-yl)ethyl)-4-(trifluoromethyl)-1H-imidazol-2-yl)piperidin-1-yl)-5,6-dihydropyrido[2,3-d]pyrimidin-7(8H)-one

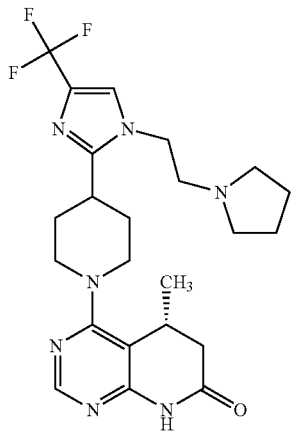 [SMILES: C[C@@H]1CC(=O)Nc2ncnc(N3CCC(c4nc(C(F)(F)F)cn4CCN4CCCC4)CC3)c21]

Add (R)-4-chloro-5-methyl-5,6-dihydropyrido[2,3-d]pyrimidin-7(8H)-one (28.30 g, 143.20 mmol), 4-(4-(trifluoromethyl)-1-(2-(pyrrolidin-1-yl)ethyl)-1H-imidazol-2-yl)piperidine (49.83 g, 1.10 eq) and triethylamine (43.47 g, 3.0 eq) in N-methylpyrrolidinone (86 mL). Heat the reaction mixture to 130° C. Cool the reaction mixture to room temperature after 2 hours. Pour the reaction mixture over ice/water (500 mL) with stirring. Extract with ethyl acetate (4×200 mL). Wash the organics with saturated aqueous sodium chloride solution, dry over anhydrous sodium sulfate and concentrate in vacuo. Suspend the solid in hexanes and stir for 30 minutes. Filter and dry under vacuum. Add 75% methyl tert-butyl ether in hexanes (800 mL) and heat to reflux. Cool the mixture to room temperature. Filter, wash with 75% methyl tert-butyl ether in hexanes (200 mL), and dry under vacuum at 40° C. to give the title compound (48.00 g, 70%). MS (ES) m/z=478 [M]$^+$.

EXAMPLE 79

(R)-4-(4-(4-Ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one hydrochloride

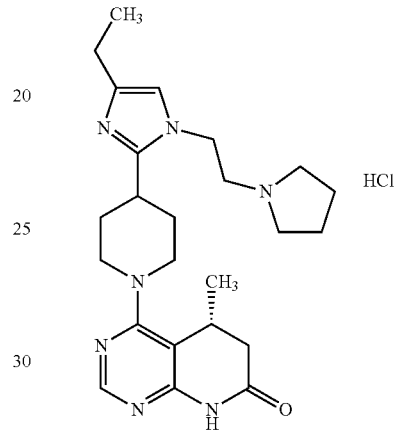

Add 4 M hydrochloric acid in dioxane (28.57 µL, 1.0 eq) to a solution of (R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one (50.00 mg, 0.11 mmol) in dichloromethane (1 mL) at room temperature and stir for 15 minutes. Concentrate in vacuo to give the title compound (54.00 mg, 100%). MS (ES) m/z=438 [M]$^+$.

Prepare the following compounds essentially as described for (R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one hydrochloride:

| Ex | Compound Name | Structure | MS (ES) m/z [M]$^+$ |
|---|---|---|---|
| 80 | (R)-4-(4-(4-isopropyl-1-(2-(pyrrolidin-1-yl)ethyl)-1H-imidazol-2-yl)piperidin-1-yl)-5-(trifluoromethyl)-5,6-dihydropyrido[2,3-d]pyrimidin-7(8H)-one hydrochloride | 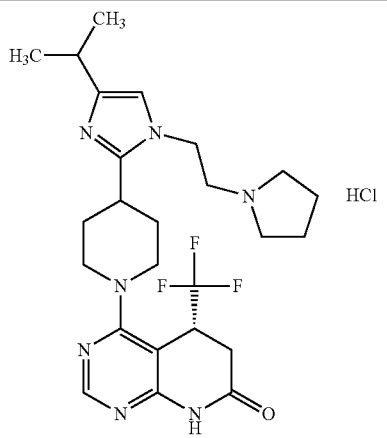 [SMILES: CC(C)c1cn(CCN2CCCC2)c(C2CCN(c3ncnc4c3[C@H](C(F)(F)F)CC(=O)N4)CC2)n1 ; Cl] | 506 |

-continued

| Ex | Compound Name | Structure | MS (ES) m/z [M]+ |
|---|---|---|---|
| 81 | (R)-4-(4-(1-(2-(pyrrolidin-1-yl)ethyl)-4-(trifluoromethyl)-1H-imidazol-2-yl)piperidin-1-yl)-5-(trifluoromethyl)-5,6-dihydropyrido[2,3-d]pyrimidin-7(8H)-one hydrochloride | 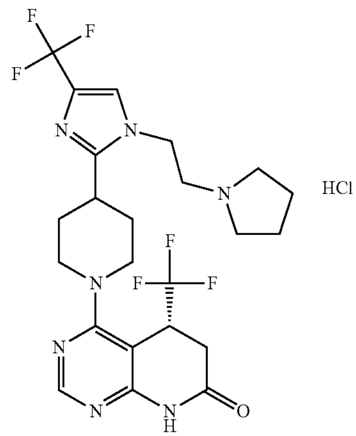 [SMILES: O=C1C[C@@H](C(F)(F)F)c2c(ncnc2N2CCC(c3nc(C(F)(F)F)cn3CCN3CCCC3)CC2)N1 ; Cl] | 532 |
| 82 | (R)-4-(4-(4-trifluoromethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one hydrochloride | 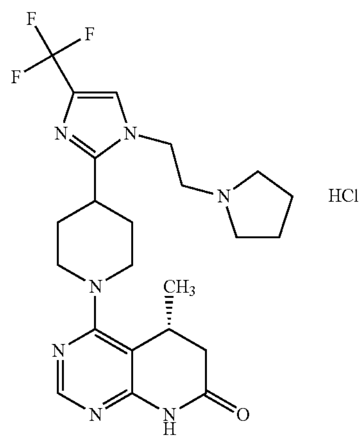 [SMILES: C[C@@H]1CC(=O)Nc2ncnc(N3CCC(c4nc(C(F)(F)F)cn4CCN4CCCC4)CC3)c21 ; Cl] | 478 |

EXAMPLE 83

(R)-4-(4-(1-(2-(tert-Butylamino)ethyl)-4-ethyl-1H-imidazol-2-yl)piperidin-1-yl)-5-(trifluoromethyl)-5,6-dihydropyrido[2,3-d]pyrimidin-7(8H)-one

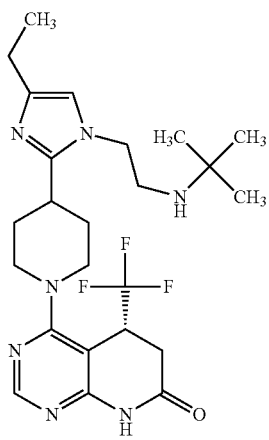 [SMILES: CCc1cn(CCNC(C)(C)C)c(C2CCN(c3ncnc4c3[C@H](C(F)(F)F)CC(=O)N4)CC2)n1]

Combine tert-butyl 4-(1-(2-(tert-butylamino)ethyl)-4-ethyl-1H-imidazol-2-yl)piperidine-1-carboxylate (440.00 mg, 1.16 mmol), dichloromethane (20 mL), methanol (8 mL), and 4 M hydrochloric acid in dioxane (3.00 mL, 12.0 eq) under nitrogen and let stir at room temperature overnight. Concentrate in vacuo to give 300 mg N-[2-[4-ethyl-2-(4-piperidyl)imidazol-1-yl]ethyl]-2-methyl-propan-2-amine Combine this amine with (R)-4-chloro-5-(trifluoromethyl)-5,6-dihydropyrido[2,3-d]pyrimidin-7(8H)-one (300.00 mg, 1.0 eq) in N-methylpyrrolidinone (10 mL) and add diisopropylethylamine (1.66 mL, 8.0 eq). Seal with crimp cap. Heat in a microwave reactor at 200° C. for 40 minutes. Dilute the reaction mixture with water and extract with ethyl acetate. Wash with saturated aqueous sodium chloride. Dry the organics over anhydrous magnesium sulfate, filter, and concentrate in vacuo. Purify by silica gel chromatography, eluting with hexanes to ethyl acetate to 5% methanol/ethyl acetate to 3% to 5% to 7% to 10% methanol/dichloromethane, to give the title compound (0.08 g, 14%). MS (ES) m/z=494 [M]+.

Prepare the following compounds essentially as described for (R)-4-(4-(1-(2-(tert-butylamino)ethyl)-4-ethyl-1H-imidazol-2-yl)piperidin-1-yl)-5-(trifluoromethyl)-5,6-dihydropyrido[2,3-d]pyrimidin-7(8H)-one:

| Ex | Compound Name | Structure | MS (ES) m/z [M]+ |
|---|---|---|---|
| 84 | (R)-4-(4-(1-(2-(dimethylamino)ethyl)-4-ethyl-1H-imidazol-2-yl)piperidin-1-yl)-5-(trifluoromethyl)-5,6-dihydropyrido[2,3-d]pyrimidin-7(8H)-one | 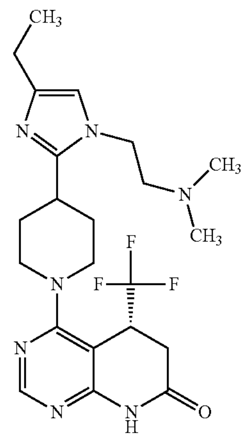 [SMILES: CCc1cn(CCN(C)C)c(C2CCN(c3ncnc4c3[C@H](C(F)(F)F)CC(=O)N4)CC2)n1] | 466 |
| 85 | (R)-4-(4-(1-(2-((S)-3-hydroxypyrrolidin-1-yl)ethyl)-4-isopropyl-1H-imidazol-2-yl)piperidin-1-yl)-5-methyl-5,6-dihydropyrido[2,3-d]pyrimidin-7(8H)-one | 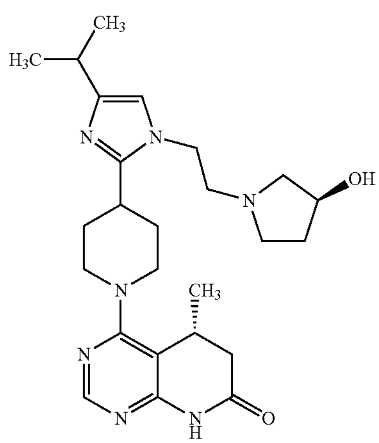 [SMILES: CC(C)c1cn(CCN2CC[C@H](O)C2)c(C2CCN(c3ncnc4c3[C@H](C)CC(=O)N4)CC2)n1] | 468 |
| 86 | (R)-4-(4-(1-(2-((R)-3-hydroxypyrrolidin-1-yl)ethyl)-4-isopropyl-1H-imidazol-2-yl)piperidin-1-yl)-5-(trifluoromethyl)-5,6-dihydropyrido[2,3-d]pyrimidin-7(8H)-one | 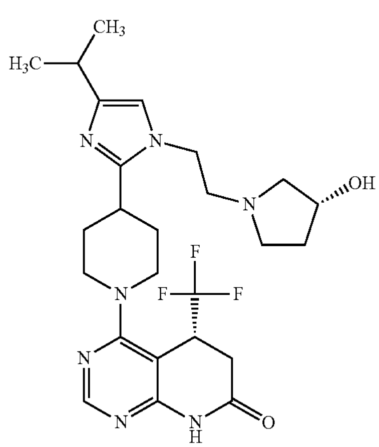 [SMILES: CC(C)c1cn(CCN2CC[C@@H](O)C2)c(C2CCN(c3ncnc4c3[C@H](C(F)(F)F)CC(=O)N4)CC2)n1] | 522 |

-continued

| Ex | Compound Name | Structure | MS (ES) m/z [M]+ |
|---|---|---|---|
| 87 | (R)-4-(4-(1-(2-((S)-3-hydroxypyrrolidin-1-yl)ethyl)-4-isopropyl-1H-imidazol-2-yl)piperidin-1-yl)-5-(trifluoromethyl)-5,6-dihydropyrido[2,3-d]pyrimidin-7(8H)-one | 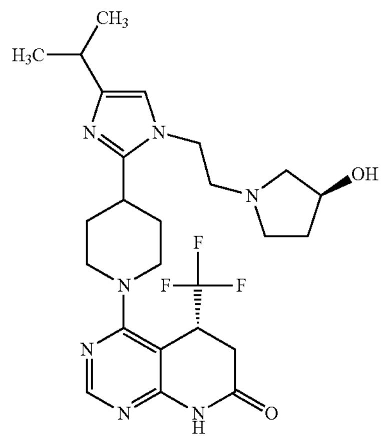 [SMILES: CC(C)c1cn(CCN2CC[C@H](O)C2)c(C2CCN(c3ncnc4c3[C@H](C(F)(F)F)CC(=O)N4)CC2)n1] | 522 |
| 88 | (R)-4-(4-(1-(2-((R)-3-hydroxypyrrolidin-1-yl)ethyl)-4-isopropyl-1H-imidazol-2-yl)piperidin-1-yl)-5-methyl-5,6-dihydropyrido[2,3-d]pyrimidin-7(8H)-one | 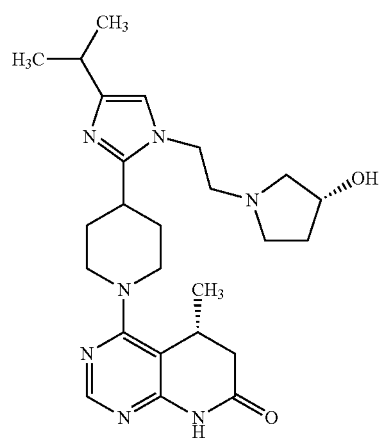 [SMILES: CC(C)c1cn(CCN2CC[C@@H](O)C2)c(C2CCN(c3ncnc4c3[C@H](C)CC(=O)N4)CC2)n1] | 468 |
| 89 | (R)-4-(4-(1-(2-(cyclopropylmethylamino)ethyl)-4-ethyl-1H-imidazol-2-yl)piperidin-1-yl)-5-methyl-5,6-dihydropyrido[2,3-d]pyrimidin-7(8H)-one | 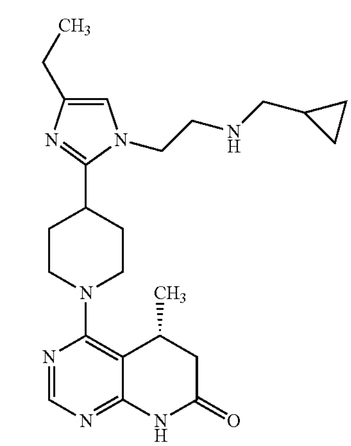 [SMILES: CCc1cn(CCNCC2CC2)c(C2CCN(c3ncnc4c3[C@H](C)CC(=O)N4)CC2)n1] | 438 |

| Ex | Compound Name | Structure | MS (ES) m/z [M]+ |
|---|---|---|---|
| 90 | (R)-4-(4-(1-(2-(cyclopentylamino)ethyl)-4-ethyl-1H-imidazol-2-yl)piperidin-1-yl)-5-methyl-5,6-dihydropyrido[2,3-d]pyrimidin-7(8H)-one | 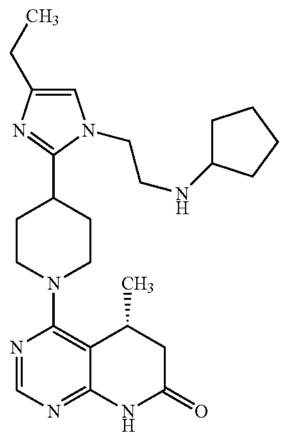 [SMILES: CCc1cn(CCNC2CCCC2)c(C2CCN(c3ncnc4c3[C@H](C)CC(=O)N4)CC2)n1] | 452 |
| 91 | (R)-4-(4-(4-ethyl-1-(2-(isopropylamino)ethyl)-1H-imidazol-2-yl)piperidin-1-yl)-5-methyl-5,6-dihydropyrido[2,3-d]pyrimidin-7(8H)-one | 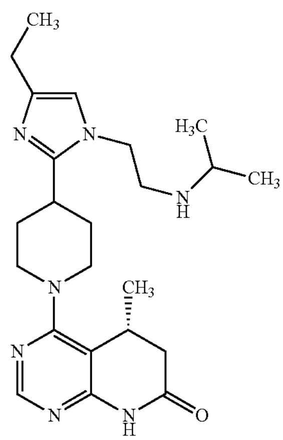 [SMILES: CCc1cn(CCNC(C)C)c(C2CCN(c3ncnc4c3[C@H](C)CC(=O)N4)CC2)n1] | 426 |

EXAMPLE 92

(R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one

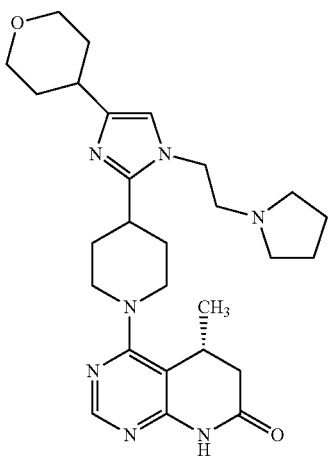 [SMILES: C[C@@H]1CC(=O)Nc2ncnc(N3CCC(c4nc(C5CCOCC5)cn4CCN4CCCC4)CC3)c21]

a. Methyl 3-(4,6-dihydroxypyrimidin-5-yl)butanoate

Charge anhydrous methanol (50 mL) to a flask followed by sodium methoxide (5.4 g, 0.1 mol, 0.3 equiv) and heat the mixture to 65-70° C. Add propanedioic acid dimethyl ester (44 g, 0.33 mol, 1.0 equiv) drop wise and the stir mixture at 65-70° C. for 10-30 min. Add ethyl crotonate (33.4 g, 0.33 mol, 1.0 equiv) drop wise over 1-2 h, and stir the mixture at 65-70° C. for 1-1.5 h. Cool the reaction mixture to −20° C. to −10° C. In a separate flask, dissolve sodium methoxide (54 g, 1.0 mol, 3.0 equiv) in anhydrous methanol (180 mL) and stir the mixture for 20-30 min. Cool the mixture to −20° C. to −10° C., and add formamidine acetate (40 g, 0.4 mol, 1.2 equiv). Add this solution drop wise to the first solution over a period of 1 h while maintaining the temperature from −20° C. to −10° C. Stir for 1-2 h and then warm the mixture to 20-25° C. over 3-4 h. Stir the mixture for 2-8 h, and then charge a solution of concentrated HCl (110-130 g) in water (330 g-390 g) while keeping the reaction temperature <10° C. Stir the suspension for 30-60 min at <10° C. and filter. Wash the filter cake with water (70 mL) and slurry the filter cake with methanol (56 g). Filter to collect methyl 3-(4,6-dihydroxypyrimidin-5-yl)butanoate (55.6 g, 72%). MS (ES) m/z=213 [M]+.

b. Methyl 3-(4,6-dichloropyrimidin-5-yl)butanoate

Dissolve methyl 3-(4,6-dihydroxypyrimidin-5-yl)butanoate (59.4 g, 0.28 mol, 1.0 equiv) in toluene (600 mL) and stir the solution for 10-20 min and then concentrate under vacuum at 50-60° C. to azeotropically remove water. Cool the mixture to 20-30° C., and add phosphoryl chloride (91.4 g, 2.13 equiv) and N,N'-diethylaniline (45.7 g, 1.1 equiv) sequentially while maintaining the temperature <40° C. Stir the reaction mixture for 10-30 min and then warm to 80-85° C. and stir for 18-20 h. Cool the mixture to 20-30° C. and add a solution of $Na_2HPO_4 \cdot 12H_2O$ (60 g, 0.17 mol) dissolved in water (500-600 g) at 30-40° C. Stir the solution for 30-60 minutes, and allow the layers to separate. Extract the aqueous layer with methyl tert-butyl ether (220-300 g) and combine the organic layers. Wash the organic phase with water (500-600 g) and concentrate the organic phase in vacuo at 50-60° C. to ~2.5-3 solvent volumes. Add isopropanol (140-160 g), and reconcentrate the solution. Use the IPA solution as is in the next step (in situ yield of methyl 3-(4,6-dichloropyrimidin-5-yl)butanoate is 85%). MS (ES) m/z=249 [M]+.

c. 4-Chloro-5-methyl-5,6-dihydropyrido[2,3-d]pyrimidin-7(8H)-one

Azeotropically dry a solution as prepared in (b) containing methyl 3-(4,6-dichloropyrimidin-5-yl)butanoate (500 g, 2 mol) and add to a solution of ammonia gas (408 g) in isopropanol (6 L). Heat the mixture to 58-62° C. and stir for 40-45 h. Cool the mixture to 20-25° C. and concentrate until the pH of the mixture is ≦9. Add water (3.75 L), cool the suspension to 0-10° C. and stir for 2-3 h. Filter the suspension and wash the filter cake with cooled isopropanol (320 mL). Dry the product in vacuo to give 4-chloro-5-methyl-5,6-dihydropyrido[2,3-d]pyrimidin-7(8H)-one (255 g, 64%). MS (ES) m/z=198 [M]+.

d. (R)-tert-Butyl 4-chloro-5-methyl-7-oxo-6,7-dihydropyrido[2,3-d]pyrimidine-8(5H)-carboxylate Charge 4-chloro-5-methyl-5,6-dihydropyrido[2,3-d]pyrimidin-7(8H)-one (233.6 g, 1.18 mol), 4-(dimethylamino)pyridine (7.2 g, 0.05 eq) and dichloromethane (880 mL) to a reactor and stir for 10-20 min. Add a solution of tert-butoxycarbonyl tert-butyl carbonate (284.1 g, 1.1 eq) dissolved in dichloromethane (200 mL) over 1.5-2 h. Stir the mixture at room temperature for 1.5 to 2 h, and charge heptanes (1100 mL). Concentrate the mixture in vacuo to remove dichloromethane to ≦2 wt %. Cool the mixture to 5-10° C. and stir for 0.5-1 h at this temperature. Filter the suspension and slurry the wet cake with heptanes (200 mL). Filter and dry in vacuo to yield the racemic compound (341.8 g, 96%). Accomplish enantiomer resolution by Chiral separation (Chiralpak AD, 9:1 hexane (0.2% dimethylethylamine):isopropyl alcohol). Combine the collected fractions and concentrate the mixture under vacuum. Add heptanes (1000 mL) and concentrate the solution in vacuo to ~2 volumes. Repeat this procedure to a residual isopropanol level of <1% (w/w). Cool the mixture to 0-5° C. and stir for 2-3 h. Filter the resulting suspension and wash the filter cake with cold heptanes (180-mL). Dry the filter cake in vacuo to yield (R)-tert-butyl 4-chloro-5-methyl-7-oxo-6,7-dihydropyrido[2,3-d]pyrimidine-8(5H)-carboxylate as enantiomer 1 (165 g, 99.8% ee, 92% yield). MS (ES) m/z=298 [M]+.

e. (R)-4-Chloro-5-methyl-5,6-dihydropyrido[2,3-d]pyrimidin-7(8H)-one

Add (R)-tert-Butyl 4-chloro-5-methyl-7-oxo-6,7-dihydropyrido[2,3-d]pyrimidine-8(5H)-carboxylate (36 g, 1.0 equiv) to water (120 mL) and stir to form a suspension. Add 12N HCl (120 g, 10 equiv) drop wise at 20-30° C. and stir the mixture for 6-8 h. A solution gradually forms. Cool the solution to 5-10° C. and add concentrated ammonium hydroxide (86.4 g, 2.4 equiv) to form a suspension. Stir the suspension for 2-3 h and is filter. Wash the filter cake with cooled water (36 mL), and then slurry with cooled isopropanol (28 g). Filter the slurry and dry the filter cake in vacuo to yield (R)-4-chloro-5-methyl-5,6-dihydropyrido[2,3-d]pyrimidin-7(8H)-one (21 g, 87%). MS (ES) m/z=198 [M]+.

f. 1-(Tetrahydro-pyran-4-yl)-ethanone—Method A

Add 2 M isopropylmagnesium chloride in tetrahydrofuran (520.22 mL, 3.0 eq) to a mixture of methyl tetrahydro-2H-pyran-4-carboxylate (46.30 mL, 346.81 mmol) and N,O-dimethylhydroxylamine hydrochloride (52.44 g, 1.6 eq) in tetrahydrofuran (2.43 L) during 15 minutes at −20° C. under nitrogen. After 30 min, add saturated aqueous ammonium chloride (400 mL) to the reaction at −20° C. Extract the aqueous solution with methyl tert-butyl ether (250 mL×3). Wash the combined organics with saturated aqueous sodium chloride. Dry over anhydrous magnesium sulfate and concentrate in vacuo. Add dichloromethane (500 mL), filter through Celite® and concentrate in vacuo. Add tetrahydrofuran (700 mL), then add 3 M methyl magnesium chloride in tetrahydrofuran (231.21 mL, 2.0 eq) dropwise over 15 minutes at 7° C. After 40 minutes, add saturated aqueous ammonium chloride (250 mL) to the reaction. Extract the aqueous solution with methyl tert-butyl ether (250 mL×2). Dry over anhydrous magnesium sulfate and concentrate in vacuo. Purify by silica gel chromatography, eluting with 2:1 hexanes:ethyl acetate to 1:1 hexanes:ethyl acetate, to give 1-(tetrahydro-pyran-4-yl)-ethanone (33.18 g, 75%). $^1$H NMR (300 MHz, DMSO-d6) δ 3.98 (m, 2H), 3.42 (m, 2H), 2.52 (m, 1H), 2.15 (s, 3H), 1.74 (m, 4H).

g. 1-(Tetrahydro-pyran-4-yl)-ethanone—Method B

Add 40% w/w sodium hydroxide in water (264.5 mL, 1.15 eq) to a solution of methyl tetrahydro-2H-pyran-4-carboxylate (500 g, 3.47 mol) in methanol (2.26 L). Stir at 50° C. for seven hours. Evaporate solvent, dissolve residue in water (2 L) and wash with methyl-tert-butyl ether (2×1.2 L). Add aqueous 35% hydrochloric acid to the aqueous layer (adjusting pH to 4) and extract with methyl tert-butyl ether (2×1.2 L). Dry over anhydrous magnesium sulfate and concentrate in vacuo. As material still contains water, dissolve the solid in dichloromethane and discard the aqueous layer. Dry the organics with anhydrous sodium sulfate and concentrate in vacuo to give tetrahydro-2H-pyran-4-carboxylic acid (312.76 g, 69%). $^1$H NMR (300 MHz, DMSO-d6) δ 11.21 (br s, 1H), 3.97 (m, 2H), 3.44 (m, 2H), 2.56 (m, 1H), 1.81 (m, 4H).

Add 1,1'-carbonyldiimidazole (333.41 g, 1.2 eq) to a solution of tetrahydro-2H-pyran-4-carboxylic acid (223 g, 1.71 mol) in dichloromethane (2.23 L) portion wise over 15 minutes. Stir for two hours. Add N,O-dimethylhydroxylamine hydrochloride (183.86 g, 1.1 eq) portionwise and stir for three hours. Wash the organics with saturated aqueous ammonium chloride, then with saturated aqueous sodium chloride. Dry the organics over anhydrous magnesium sulfate and concentrate in vacuo to give N-methoxy-N-methyl-tetrahydropyran-4-carboxamide (339 g, 114%) as crude material and use as such in next reaction. $^1$H NMR (300 MHz, DMSO-d6) δ 4.02 (m, 2H), 3.71 (s, 3H), 3.46 (m, 2H), 3.19 (s, 3H), 2.91 (m, 1H), 1.86 (m, 2H), 1.65 (m, 2H).

Add 3 M methyl magnesium bromide in diethyl ether (1.14 L, 2.0 eq) to a solution of N-methoxy-N-methyl-tetrahydro-pyran-4-carboxamide (296 g, 1.71 mol) in tetrahydrofuran (2.96 L) over one hour at 0° C. Stir for an additional two hours, then pour the contents into a mixture of ice/water. Extract with methyl tert-butyl ether. Dry the organics over anhydrous magnesium sulfate and concentrate in vacuo to give 1-(tetrahydro-pyran-4-yl)-ethanone (105 g, 48%). $^1$H NMR (300 MHz, DMSO-d6) δ 3.98 (m, 2H), 3.42 (m, 2H), 2.52 (m, 1H), 2.15 (s, 3H), 1.74 (m, 4H).

h. tert-Butyl 4-(4-(tetrahydro-2H-pyran-4-yl)-1H-imidazol-2-yl)piperidine-1-carboxylate Combine selenium dioxide (181.80 g, 1.64 mol), 1,4-dioxane (630 mL), acetic acid (31.5 mL, 0.67 eq), and water (31.5 mL). Heat to 90° C. and add 1-(tetrahydro-pyran-4-yl)-ethanone (105.0 g, 1.0 eq) dropwise. Stir at 90° C. overnight. After cooling, filter through a plug of silica/Celite® and wash with tetrahydrofuran (2.5 L). Dry the organics over anhydrous magnesium sulfate, filter, and concentrate in vacuo. Dissolve the crude material in methanol (500 mL) and add to a solution of tert-butyl 4-formylpiperidine-1-carboxylate (174.72 g, 1.0 eq) and ammonium acetate (315.74 g, 5.0 eq) in methanol (1.45 L) at 0° C. Stir overnight. Filter through silica/Celite® and wash with ethyl acetate and methanol. Concentrate the filtrate in vacuo. Dilute with methyl tert-butyl ether (400 mL) and water (400 mL), then adjust the pH to 2 by addition of aqueous 85% phosphoric acid. Separate the layers and wash the aqueous phase with methyl tert-butyl ether (200 mL). Basify the resulting aqueous phase with solid sodium carbonate to pH 10 and extract with ethyl acetate (3×200 mL). Wash the organics with saturated aqueous sodium chloride. Dry the organics over anhydrous magnesium sulfate, filter, and concentrate in vacuo to afford tert-butyl 4-(4-(tetrahydro-2H-pyran-4-yl)-1H-imidazol-2-yl)piperidine-1-carboxylate (105.1 g, 38%). MS (ES) m/z=336 [M]$^+$.

i. tert-Butyl 4-(4-(tetrahydro-2H-pyran-4-yl)-1-(2-(pyrrolidin-1-yl)ethyl)-1H-imidazol-2-yl)piperidine-1-carboxylate Combine tert-butyl 4-(4-(tetrahydro-2H-pyran-4-yl)-1H-imidazol-2-yl)piperidine-1-carboxylate (101.10 g, 301.39 mmol) and freshly ground potassium hydroxide (50.73 g, 3.0 eq) in dimethyl sulfoxide (500 mL). Stir for 15 minutes, then add sodium iodide (49.69 g, 1.1 eq). Add a solution of 1-(2-chloro-ethyl)-pyrrolidinium chloride (66.64 g, 1.3 eq) in dimethyl sulfoxide (1.01 L) and stir for four hours at room temperature. Pour the contents of the reaction into an ice/water mixture (~1 L) and extract with methyl tert-butyl ether. Dry the organics over anhydrous magnesium sulfate, filter, and concentrate in vacuo. Purify by HPLC (Chiralpak AD basic, hexane/ethanol 9:1) to give tert-butyl 4-(4-(tetrahydro-2H-pyran-4-yl)-1-(2-(pyrrolidin-1-yl)ethyl)-1H-imidazol-2-yl)piperidine-1-carboxylate (82.0 g, 63%). MS (ES) m/z=433 [M]$^+$.

j. 4-(1-(2-Pyrrolidin-1-yl-ethyl)-4-(tetrahydro-pyran-4-yl)-1H-imidazol-2-yl)-piperidine Add 5 M hydrogen chloride in isopropyl alcohol (112.7 mL, 5.0 eq) to a solution of tert-butyl 4-(1-(2-(pyrrolidin-1-yl)ethyl)-4-(tetrahydro-2H-pyran-4-yl)-1H-imidazol-2-yl)piperidine-1-carboxylate (132.0 g, 274.61 mmol) in isopropyl alcohol (549 mL). Stir the reaction mixture at 50° C. for six hours. Concentrate in vacuo. Dilute with water (1 L) and adjust the pH to 12 with 2 M aqueous sodium hydroxide. Extract with ethyl acetate and dichloromethane. Dry the organics over anhydrous magnesium sulfate and concentrate in vacuo to give 4-(1-(2-pyrrolidin-1-yl-ethyl)-4-(tetrahydro-pyran-4-yl)-1H-imidazol-2-yl)-piperidine (81.9 g, 90%). MS (ES) m/z=333 [M]$^+$.

k. (R)-5-methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one Combine (R)-4-chloro-5-methyl-5,6-dihydropyrido[2,3-d]pyrimidin-7(8H)-one (53.55 g, 270.96 mmol), triethylamine (37.77 mL, 1.1 eq), 4-(1-(2-pyrrolidin-1-yl-ethyl)-4-(tetrahydro-pyran-4-yl)-1H-imidazol-2-yl)-piperidine (81.9 g, 1.0 eq) and N-methylpyrrolidinone (246 mL). Stir at 110° C. overnight. Cool the reaction mixture to room temperature and dilute with ethyl acetate (400 mL) and water (1200 mL). Adjust the pH to 10 with 2 M aqueous sodium hydroxide and separate layers. Wash the aqueous phase with ethyl acetate (2×200 mL). Wash the organics with aqueous saturated sodium chloride. Add water (1 L) to the organics and adjust the pH to 3 with aqueous 85% phosphoric acid. Separate the layers and wash the resulting acidic aqueous phase with ethyl acetate (2×200 mL). Adjust the pH of the aqueous phase to 10 with 2 M aqueous sodium hydroxide. Extract with ethyl acetate (3×200 mL). Wash the organics with saturated aqueous sodium chloride (250 mL), dry over anhydrous magnesium sulfate, and concentrate in vacuo. Purify the residue by HPLC (Chiralpak AD, 70/30 hexanes/isopropyl alcohol w/0.2% dimethylethylamine) to give the final compound (51.0 g, 42%). MS (ES) m/z=494 [M]$^+$.

Determine chiral purity of (R)-5-methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one by comparison with opposite enantiomer using two different conditions:

HPLC: Chiralpak AD-H (4.6×150 mm; 5 um) 100% ethanol w/0.2% dimethylethylamine

SFC: Chiralpak AD-H (4.6×100 mm; 5 um) 65/35 CO$_2$/ethanol w/0.2% dimethylethylamine In both methods, the enantiomer percentage is 99% (R), 1% (S) ee=98%.

EXAMPLE 93

(R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one

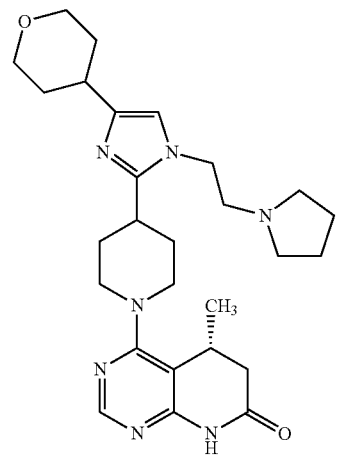 [SMILES: C[C@@H]1CC(=O)Nc2ncnc(N3CCC(c4nc(C5CCOCC5)cn4CCN4CCCC4)CC3)c21]

a. 2,2-Dibromo-1-(tetrahydro-2H-pyran-4-yl)ethanone

Prepare lithium diisopropyl amide (LDA) as follows: Charge diisopropylamine (316.8 g, 2.5 equiv) and methyl tert-butyl ether (1.25 L) to a reactor and cool the reaction vessel to −10° C. to 0° C. Add n-butyl lithium in hexane (748 g, 2.2 equiv) while maintaining the temperature between −10° C. and 0° C. Stir the mixture for 30-60 min. In a separate vessel, add methyl tert-butyl ether (1.8 L), dibromomethane (471.6 g, 2.2 equiv) and methyl tetrahydro-2H-pyran-4-carboxylate (180 g) and cool to −90° C. to −70° C. Slowly add the LDA solution while maintaining the temperature between −90° C. and −70° C. After 30-90 min, transfer the reaction mixture to a solution of 1 N HCl (5.58 kg) maintained at 0-10° C. Upon completion of the addition, allow the mixture to warm to 15° C. to 25° C. and stir at this temperature for 15-20 min. Separate and discard the aqueous layer. Wash the organic layer with water (1.8 L) until the water layer registers a pH of 6-7, and concentrate the organic layer in vacuo to ~2.2-2.5 volumes below 35° C. Add n-heptanes (720 mL), cool to −10° C. to −5° C. and stir for 1-2 h. Filter, rinse the filter cake with cold heptanes (90 mL) and dry under vacuum to give 2,2-dibromo-1-(tetrahydro-2H-pyran-4-yl)ethanone as a pale yellow solid (203.6 g, 55%). $^1$H NMR (400 MHz, CDCl$_3$) δ 5.87 (s, 1H), 4.02 (m, 2H), 3.48 (m, 2H), 3.34 (m, 1H), 1.86 (m, 4H).

b. tert-Butyl 4-(4-(tetrahydro-2H-pyran-4-yl)-1H-imidazol-2-yl)piperidine-1-carboxylate Combine 2,2-dibromo-1-(tetrahydro-2H-pyran-4-yl)ethanone (100 g, 1.0 equiv), tert-butyl 4-formylpiperidine-1-carboxylate (75 g, 1.0 eq), toluene (800 mL) in a reactor. Stir for 15 min at 20-30° C., and add 25-28% ammonium hydroxide in water (800 mL, 8.0 equiv) and heat at 68° C. to 72° C. for 16-20 hours. Cool the reaction mixture to 20° C. to 30° C. and add methyl tert-butyl ether (300 mL). Stir at 20° C. to 30° C. for 15 to 20 min and separate the aqueous layer. Wash the organic layer with water (500 mL) to a pH≦8. Concentrate the organic layer to 2 volumes in vacuo, and add toluene (200 mL). Reconcentrate to ~2 volumes and determine water content by Karl Fischer titration (wt % water ≦0.1%). Adjust the temperature to 20° C.-30° C. and add isopropanol (50 mL) and heptanes (600 mL). Stir at 20° C. to 30° C. for 4-16 h, cool to 0° C. to 5° C. and stir for an additional 2-5 h. Filter and dry under vacuum to give, to give tert-butyl 4-(4-(tetrahydro-2H-pyran-4-yl)-1H-imidazol-2-yl)piperidine-1-carboxylate (40 g, 35%). MS (ES) m/z=336 [M]$^+$.

c. 4-(1-(2-(Pyrrolidin-1-yl)ethyl)-4-(tetrahydro-2H-pyran-4-yl)-1H-imidazol-2-yl)piperidine trihydrochloride Charge degassed dimethylsulfoxide (750 mL) to a flask, followed by tert-butyl 4-(4-(tetrahydro-2H-pyran-4-yl)-1H-imidazol-2-yl)piperidine-1-carboxylate (150 g, 1.0 equiv), sodium iodide (87.2 g, 1.3 equiv), potassium hydroxide (15 g, 0.6 equiv) and potassium tert-butoxide (95.3 g, 1.9 equiv) while maintaining the temperature between 20° and 35° C. Heat the mixture to 30-35° C. In a separate reactor, dissolve 1-(2-chloroethyl)pyrrolidine hydrochloride (83.7 g, 1.1 equiv) in dimethylsulfoxide (750 mL) and transfer to the first reactor at 30°-35° C. Adjust the temperature to 40°-45° C. and stir for 2-3 h. Cool the mixture to 20°-30° C. and add methyl tert-butyl ether (3 L). Wash the organic phase with water (1.5 L), and back-extract the aqueous layer with methyl tert-butyl ether (3 L). Combine the organic layers, wash with water (1.5 L), separate and treat the organic layer with activated charcoal (7.5 g, 0.05 equiv)) for 1-2 h at 40°-45° C. Filter off the charcoal and wash with methyl tert-butyl ether (150 mL). Concentrate to 3-v volumes in vacuo and add methanol (1.05 L). Concentrate again to 3-4 volumes. Add a solution of 2 N hydrochloric acid in methanol (1.1 L, 5.0 equiv), and heat at 50° C.-60° C. for 2 h. Concentrate to 3-4 volumes in vacuo and add ethyl acetate (1.35 L) drop wise with the temperature at 50° C.-60° C., and stir at that temperature for 1-2 h. Cool the reaction mixture to 20° C.-30° C. and stir at that temperature for 1-2 h. Filter and rinse the cake with 3:1 ethyl acetate: MeOH (300 mL) to give 4-(1-(2-(pyrrolidin-1-yl)ethyl)-4-(tetrahydro-2H-pyran-4-yl)-1H-imidazol-2-yl)piperidine trihydrochloride as a single regioisomer (130 g, 58%). MS (ES) m/z=333 [M]$^+$.

d. (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one Prepare according to step k in Example 92.

EXAMPLE 94

(R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one

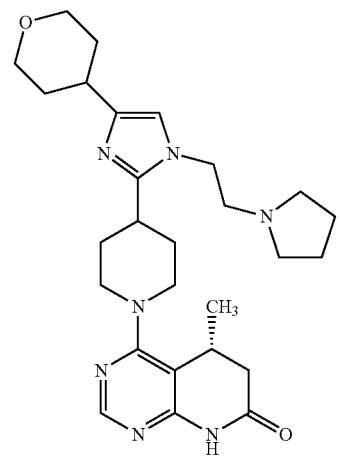 [SMILES: C[C@@H]1CC(=O)Nc2ncnc(N3CCC(c4nc(C5CCOCC5)cn4CCN4CCCC4)CC3)c21]

a. (R)-4-Chloro-5-methyl-5,6-dihydropyrido[2,3-d]pyrimidin-7(8H)-one

Prepare according to steps a to e of Example 92.

b. tert-Butyl 4-(1H-imidazol-2-yl)piperidine-1-carboxylate

Add 28% ammonium hydroxide in water (372.66 mL, 5.0 eq) to a solution of tert-butyl 4-formylpiperidine-1-carboxylate (127 g, 595.47 mmol) in methanol (508 mL) and stir for 15 minutes. Add ethanedial (108.74 g, 1.0 eq) dropwise, maintaining the temperature of the mixture below 25° C. with an ice/water bath. Stir for one hour. Add water (1.14 L) dropwise over 45 minutes and stir the resulting suspension for 16 hours at room temperature. Filter the suspension to give tert-butyl 4-(1H-imidazol-2-yl)piperidine-1-carboxylate as a white solid (113 g, 76%). Refilter the previous filtrate to obtain additional material (15 g, 10%). MS (ES) m/z=252 [M]+.

c. tert-Butyl 4-(4,5-diiodo-1H-imidazol-2-yl)piperidine-1-carboxylate

Method 1:
Add iodine (104 g, 2.05 eq) to a solution of tert-butyl 4-(1H-imidazol-2-yl)piperidine-1-carboxylate (50 g, 198.94 mmol) in dimethyl sulfoxide (200 mL) portionwise over 15 minutes (the temperature rises to 45° C.). Stir the solution for 30 minutes, then add potassium hydroxide (85%, 19.70 g, 1.5 eq) and stir for 16 hours. Pour the mixture slowly into 0.15 M aqueous sodium bisulfite (1.25 L) to obtain a yellow suspension. Stir for 45 minutes, filter, wash the solids with water, and dry to give tert-butyl 4-(4,5-diiodo-1H-imidazol-2-yl)piperidine-1-carboxylate as a pale yellow solid (98 g, 98%). MS (ES) m/z=504 [M]+.
Method 2:
Add N-iodosuccinimide (46.81 g, 2.0 eq) to a solution of tert-butyl 4-(1H-imidazol-2-yl)piperidine-1-carboxylate (25 g, 99.47 mmol) in N-methylpyrrolidinone (75 mL) portionwise, maintaining the temperature below 30° C. Stir for 15 minutes, then pour the mixture slowly into 0.07 M aqueous sodium bisulfite (0.75 L) to obtain a yellow suspension. Stir for 30 minutes, filter, wash the solids with water, and dry to give tert-butyl 4-(4,5-diiodo-1H-imidazol-2-yl)piperidine-1-carboxylate as a pale yellow solid (49 g, 98%). MS (ES) m/z=504 [M]+.

d. tert-Butyl 4-[4,5-diiodo-1-(2-pyrrolidin-1-ylethyl)imidazol-2-yl]piperidine-1-carboxylate Add potassium hydroxide (45.13 g, 4.0 eq) to a solution of tert-butyl 4-(4,5-diiodo-1H-imidazol-2-yl)piperidine-1-carboxylate (86 g, 170.9 mmol) in N-methylpyrrolidinone (258 mL) portionwise over 25 minutes, maintaining the temperature below 40° C. Stir the mixture for 25 minutes, then add 1-(2-chloroethyl)pyrrolidine hydrochloride (47.5 g, 1.6 eq) portionwise. Stir the resulting mixture for 16 hours at 40° C., then allow to cool to room temperature. Pour the reaction into water (3.1 L) and add aqueous 15% phosphoric acid to adjust the pH to 7.5-8. Stir the resulting suspension for one hour at 0-5° C. Filter, wash with water, and dry under vacuum at 50° C. to give tert-butyl 4-[4,5-diiodo-1-(2-pyrrolidin-1-ylethyl)imidazol-2-yl]piperidine-1-carboxylate (102 g, 99%). MS (ES) m/z=601 [M]+.

e. tert-Butyl 4-[4-iodo-1-(2-pyrrolidin-1-ylethyl)imidazol-2-yl]piperidine-1-carboxylate Combine tert-butyl 4-[4,5-diiodo-1-(2-pyrrolidin-1-ylethyl)imidazol-2-yl]piperidine-1-carboxylate (39 g, 64.97 mmol) and 2-methyltetrahydrofuran (273 mL), then cool to −15° C. Add 2 M isopropylmagnesium chloride in tetrahydrofuran (32.48 mL, 1.0 eq) dropwise over 45 minutes, maintaining the temperature below −10° C. Stir for an additional 30 min. Add acetic acid (7.45 mL) dropwise, then water (120 mL). Wash the aqueous phase with methyl tert-butyl ether (2×50 mL). Wash the organics with aqueous saturated sodium chloride. Dry the organics over anhydrous magnesium sulfate and concentrate in vacuo. Crystallize the resulting oil from hexanes/methyl tert-butyl ether to give tert-butyl 4-[4-iodo-1-(2-pyrrolidin-1-ylethyl)imidazol-2-yl]piperidine-1-carboxylate as a white solid (29 g, 94%). MS (ES) m/z=475 [M]+.

f. 4-Allyloxybut-1-yne

Combine allyl bromide (124.27 g, 1.03 mol) and methyl tert-butyl ether (504 mL), then cool to −5/0° C. Add sodium hydride (49.30 g, 1.19 eq), then 3-butyn-1-ol (78 mL, 1.0 eq) dropwise over 20 minutes. Stir the mixture for 15 minutes at −5/0° C. and then at room temperature for 16 hours. Add sodium sulfate decahydrate (36 g, 0.1 eq) and stir for 30 minutes. Filter with over pressure through Celite® and wash with methyl tert-butyl ether (200 mL) to give 4-allyloxybut-1-yne as a solution in methyl tert-butyl ether. A quantitative yield is assumed.

g. 2-(3-Allyloxy-1-methylene-propyl)-4,4,5,5-tetramethyl-1,3,2-dioxaborolane

Add lithium chloride (44.90 g, 1.05 eq) to a suspension of cuprous monochloride (104.85 g, 1.05 eq) in dimethylformamide (770 mL). Stir the mixture for one hour and add bis(pinacolato)diboron (271.70 g, 1.05 eq) and potassium acetate (103.95 g, 1.05 eq). Cool the resulting black suspension to 0° C. and add 4-allyloxybut-1-yne (solution in methyl tert-butyl ether, 110 g, 998.58 mmol) dropwise. Stir for 16 hours, then dilute with 2 M aqueous ammonium chloride (1 L), methyl tert-butyl ether (500 mL), and hexanes (500 mL). Stir the suspension for 30 minutes, filter through Celite® and wash with hexanes (1 L). Wash the aqueous phase with hexanes (2×200 mL). Wash the organics with water and saturated aqueous sodium chloride. Concentrate in vacuo to obtain a crude oil (218 g). Purify a portion (45 g) by silica gel chromatography, eluting with hexanes to 70/30 hexanes/methyl tert-butyl ether, to give 2-(3-allyloxy-1-methylene-propyl)-4,4,5,5-tetramethyl-1,3,2-dioxaborolane (27 g, 131 g extrapolated to remainder of oil, 55%, 2 steps). $^1$H NMR (300 MHz, CDCl$_3$) δ 5.93 (m, 2H), 5.69 (m, 1H), 5.26 (dq, J=17.2, 1.7 Hz, 1H), 5.15 (m, 1H), 3.97 (dt, J=5.8, 1.4 Hz, 2H), 3.51 (t, J=7.0 Hz, 2H), 2.44 (t, J=7.1 Hz, 2H), 1.26 (s, 12H).

h. 2-(3,6-Dihydro-2H-pyran-4-yl)-4,4,5,5-tetramethyl-1,3,2-dioxaborolane

Add Grubbs Catalyst, 2nd Generation (benzylidene-[1,3-bis(2,4,6-trimethylphenyl)imidazolidin-2-ylidene]-dichloro(tricyclohexylphosphine)ruthenium, 2.58 g, 0.03 eq) to a solution of 2-(3-allyloxy-1-methylene-propyl)-4,4,5,5-tetramethyl-1,3,2-dioxaborolane (23.4 g, 98.26 mmol) in dichloromethane (280 mL) and stir for 16 hours. Concentrate in vacuo and add hexanes (120 mL) to the residue. Stir for one hour and filter. Concentrate the filtrate in vacuo to give 2-(3,6-dihydro-2H-pyran-4-yl)-4,4,5,5-tetramethyl-1,3,2-dioxaborolane as a tan solid (20.4 g, 99%). $^1$H NMR (300 MHz, CDCl$_3$) δ 6.50 (m, 1H), 4.17 (q, J=2.7 Hz, 2H), 3.73 (t, J=5.4 Hz, 2H), 2.20 (m, 2H), 1.24 (s, 12H).

i. tert-Butyl 4-[4-(3,6-dihydro-2H-pyran-4-yl)-1-(2-pyrrolidin-1-ylethyl)imidazol-2-yl]piperidine-1-carboxylate Combine 2-(3,6-dihydro-2H-pyran-4-yl)-4,4,5,5-tetramethyl-1,3,2-dioxaborolane (19.1 g, 1.6 eq), tert-butyl 4-[4-iodo-1-(2-pyrrolidin-1-ylethyl)imidazol-2-yl]piperidine-1-carboxylate (27 g, 56.9 mmol), sodium carbonate (120.6 g, 3.0 eq), and dimethyl sulfoxide (135 mL). Stir for five minutes. Add tri-tert-butylphosphonium tetrafluoroborate (1.7 g, 0.1 eq) and palladium(II) acetate (645.4 mg, 0.05 eq). Stir the resulting suspension at 75-80° C. under nitrogen for 45 minutes. Allow the mixture to cool to room temperature, then dilute with water (190 mL) and methyl tert-butyl ether (80 mL). Wash the aqueous layer with methyl tert-butyl ether (3×54 mL). Wash the organics with water (60 mL) and then with a 10% w/w aqueous solution of phosphoric acid (60 mL, 20 mL). Combine these aqueous layers and wash them with methyl tert-butyl ether (60 mL). Add sodium carbonate to the acidic aqueous layer to adjust the pH to 12. Wash the basic aqueous layer with methyl tert-butyl ether (120 mL, 30 mL). Wash the combined organics with aqueous saturated sodium chloride, dry over anhydrous magnesium sulfate, and concentrate in vacuo to give tert-butyl 4-[4-(3,6-dihydro-2H-pyran-4-yl)-1-(2-pyrrolidin-1-ylethyl)imidazol-2-yl]piperidine-1-carboxylate (23.6 g, 96%). MS (ES) m/z=431 [M]$^+$.

j. tert-Butyl 4-[1-(2-pyrrolidin-1-ylethyl)-4-tetrahydropyran-4-yl-imidazol-2-yl]piperidine-1-carboxylate Add palladium on charcoal, (3.0 g, 50% wet, 0.1 g/g limiting reagent) to a solution of tert-butyl 4-[4-(3,6-dihydro-2H-pyran-4-yl)-1-(2-pyrrolidin-1-ylethyl)imidazol-2-yl]piperidine-1-carboxylate (30 g, 69.67 mmol) in ethanol (210 mL). Stir under a hydrogen atmosphere in a Parr system (200 psi, 65-70° C.) for 27 hours. Add additional palladium on charcoal (0.6 g, 50% wet, 0.02 g/g limiting reagent) and stir under a hydrogen atmosphere in a Parr system (200 psi, 65-70° C.) for five hours. Filter over Celite® and wash with ethanol. Concentrate the filtrate in vacuo and dissolve the residue in ethanol (150 mL). Add palladium on charcoal (0.6 g, 50% wet, 0.02 g/g limiting reagent) and stir under a hydrogen atmosphere in a Parr system (250 psi, 70° C.) for 16 hours. Filter over Celite® and wash with ethanol. Concentrate the filtrate in vacuo to give tert-butyl 4-[1-(2-pyrrolidin-1-ylethyl)-4-tetrahydropyran-4-yl-imidazol-2-yl]piperidine-1-carboxylate as a brown oil (29.5 g, 98%). MS (ES) m/z=433 [M]$^+$.

k. 4-[1-(2-pyrrolidin-1-yl-ethyl)-4-(tetrahydro-pyran-4-yl)-1H-imidazol-2-yl]-piperidine Add aqueous 35% hydrochloric acid (23.20 mL, 4.7 eq) to a solution of tert-butyl 4-[1-(2-pyrrolidin-1-ylethyl)-4-tetrahydropyran-4-yl-imidazol-2-yl]piperidine-1-carboxylate (29.0 g, 60.33 mmol) in isopropyl alcohol (120 mL). Stir at 50° C. for six hours. Concentrate in vacuo. Add water (1 L) and 2 M aqueous sodium hydroxide to adjust the pH to 12. Extract with ethyl acetate (3×200 mL) and dichloromethane (3×200 mL). Dry the organics over anhydrous magnesium sulfate and concentrate in vacuo to give 4-(4-(tetrahydro-2H-pyran-4-yl)-1-(2-(pyrrolidin-1-yl)ethyl)-1H-imidazol-2-yl) piperidine (21.5 g, 100%). MS (ES) m/z=333 [M]$^+$.

l. (R)-5-methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one Combine (R)-4-chloro-5-methyl-5,6-dihydropyrido[2,3-d]pyrimidin-7(8H)-one (15.69 g, 1.2 eq), triethylamine (10.14 mL, 1.1 eq), 4-[1-(2-pyrrolidin-1-yl-ethyl)-4-(tetrahydro-pyran-4-yl)-1H-imidazol-2-yl]-piperidine (22 g, 66.17 mmol) and N-methylpyrrolidinone (66 mL). Stir at 110° C. for 16 hours, then allow to cool to room temperature. Dilute with ethyl acetate (110 mL) and water (220 mL). Add 5 M aqueous sodium hydroxide to adjust the pH to 12. Extract with ethyl acetate (2×200 mL). Wash the organics with saturated aqueous sodium chloride. Add water (220 mL) to the organics and aqueous 85% phosphoric acid to adjust the pH to 3. Wash the resulting acidic aqueous layer with ethyl acetate (2×100 mL). Add 5 M aqueous sodium hydroxide to adjust the pH to 12. Extract with ethyl acetate (3×70 mL). Wash the organics with saturated aqueous sodium chloride (50 mL). Dry the organics over anhydrous magnesium sulfate and concentrate in vacuo to give the final compound as a light brown solid (21.5 g, 64%). MS (ES) m/z=494 [M]$^+$.

EXAMPLE 95

(R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one Crystalline Form III Approximately 100 mg of amorphous (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one is added to a small vial and mixed with 5 mL of isopropyl ether and 100 µL of butyl butyrate. A slurry of solid results. Crystalline seeds are added and the sample is slurried at room temperature and 1000 rpm overnight on the stirplate. A thick slurry of white solid results. The white solid is isolated by vacuum filtration and placed in a 65° C. vacuum oven to dry.

X-Ray Powder Diffraction: The XRD patterns of the crystals are obtained on a Bruker D8 Advance X-ray powder diffractometer, equipped with a CuKα source λ=1.54056 Å) and a Vantec detector, operating at 50 kV and 40 mA. Each sample is scanned between 4 and 40° in 2θ, with a step size of 0.02° in 2θ and a scan rate of 9.0 seconds/step, and with 1 mm divergence and receiving slits and a 0.1 mm detector slit. The dry powder is packed into recessed top-loading sample holder and a smooth surface is obtained using a glass slide. The crystal form diffraction patterns are collected at ambient temperature and relative humidity.

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2θ will take into account these potential variations without hindering the unequivocal identification of the indicated crystal form.

Confirmation of a crystal form may be made based on any unique combination of distinguishing peaks (in units of ° 2θ), typically the more prominent peaks. Thus, a prepared sample of (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one crystalline form III is characterized by an XRD pattern using CuKα radiation as having diffraction peaks (2-theta values) as described in Table 1 below, and in particular having peaks at 8.53 in combination with one or more of the peaks selected from the group consisting of 17.06, 7.97, and 14.17; with a tolerance for the diffraction angles of 0.1 degrees.

TABLE 1

X-ray powder diffraction peaks of (R)-5-Methyl-4-(4-(1-(2-(pyrrolidin-1-yl)ethyl)-4-(tetrahydro-2H-pyran-4-yl)-1H-imidazol-2-yl)piperidin-1-yl)-5,6-dihydropyrido[2,3-d]pyrimidin-7(8H)-one crystalline form III.

| Peak Angles (+/−0.1 ° 2-Theta) | Rel. Intensity (% of main peak) |
| --- | --- |
| 7.97 | 52 |
| 8.53 | 100 |
| 14.17 | 57 |
| 15.97 | 27 |
| 16.56 | 32 |
| 17.06 | 97 |
| 17.81 | 57 |
| 19.03 | 25 |
| 19.36 | 26 |
| 21.73 | 34 |

EXAMPLE 96

(R)-4-(4-(1-(2-(Azetidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one

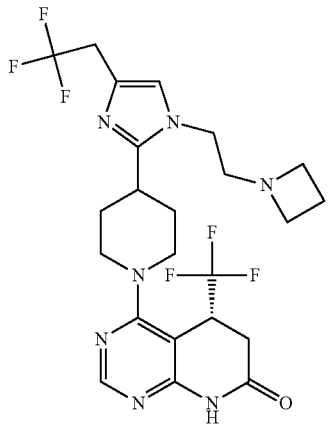 [SMILES: O=C1C[C@@H](C(F)(F)F)c2c(ncnc2N2CCC(c3nc(CC(F)(F)F)cn3CCN3CCC3)CC2)N1]

a. Methyl 3-(4,6-dihydroxypyrimidin-5-yl)-4,4,4-trifluorobutanoate

Heat a solution of 25% sodium methoxide in methanol (1.49 L, 0.86 eq) at 62° C. Add a mixture of propanedioic acid dimethyl ester (1.00 kg, 7.57 mol) and ethyl 4,4,4-trifluorocrotonate (1.27 kg, 1.0 eq) dropwise over two hours. Heat the mixture at 62° C. for two hours. Cool the mixture to 30° C. Add 25% sodium methoxide in methanol (2.34 L, 1.35 eq) and formamidine acetate (867.2 g, 1.1 eq). Stir at 30° C. overnight. Cool the mixture to 0° C. and add 5 M aqueous hydrochloric acid, adjusting the pH to 4.5. Filter and wash with water (2 L). To the wet solid, add methyl tert-butyl ether (5 L). Filter, wash with additional methyl tert-butyl ether (2 L), and dry at 50° C. to give methyl 3-(4,6-dihydroxypyrimidin-5-yl)-4,4,4-trifluorobutanoate (1.05 kg, 52%).

b. Methyl 3-(4,6-dichloropyrimidin-5-yl)-4,4,4-trifluorobutanoate

Cool phosphoryl chloride (3.15 L, 8.6 eq) to 0° C. Add methyl 3-(4,6-dihydroxypyrimidin-5-yl)-4,4,4-trifluorobutanoate (1.05 kg, 3.94 mol) dropwise. Add N,N-diethylaniline (0.69 L, 1.1 eq) dropwise over one hour. Warm the mixture slowly to 100° C. and heat overnight. Cool the mixture to room temperature and concentrate in vacuo. Dilute with acetonitrile (4 L) and add dropwise to a solution of potassium phosphate dibasic 3 M aqueous solution (6.86 kg, 10 eq), previously cooled to −2° C. Filter and wash the unwanted solids with dichloromethane. Separate the layers of the filtrate. Wash the aqueous phase with additional dichloromethane. Wash the organics with 2 M aqueous hydrochloric acid, water, and aqueous saturated sodium chloride. Dry the organics over anhydrous sodium sulfate, filter, and concentrate in vacuo to give methyl 3-(4,6-dichloropyrimidin-5-yl)-4,4,4-trifluorobutanoate (1.15 kg, 97%).

c. (R)-4-Chloro-5-(trifluoromethyl)-5,6-dihydropyrido[2,3-d]pyrimidin-7(8H)-one

Combine methyl 3-(4,6-dichloropyrimidin-5-yl)-4,4,4-trifluorobutanoate (501.0 g, 1.57 mol) and 2 M ammonia in isopropyl alcohol (1.57 L, 2.0 eq) in a pressure reactor. Heat at 120° C. for seven hours. Cool the mixture to room temperature, then concentrate in vacuo. Dilute with hexanes (1 L). Filter to give crude product. Triturate this solid with 10% isopropyl alcohol in water (600 mL) and water (1.3 L). Filter and dry at 70° C. to give 4-chloro-5-(trifluoromethyl)-5,6-dihydropyrido[2,3-d]pyrimidin-7(8H)-one (328.9 g, 83%) as a racemate. MS (ES) m/z=252 [M]$^+$.

Chiral separation (Chiralpak AS, ethanol (0.2% dimethylethylamine)) provides (R)-4-chloro-5-(trifluoromethyl)-5,6-dihydropyrido[2,3-d]pyrimidin-7(8H)-one as enantiomer 2 (>99% ee). MS (ES) m/z=252 [M]$^+$.

d. tert-Butyl 4-(4-(2,2,2-trifluoroethyl)-1H-imidazol-2-yl)piperidine-1-carboxylate Combine selenium dioxide (8.80 g, 79.32 mmol), 1,4-dioxane (50 mL), acetic acid (2 mL), and water (2 mL). Heat to reflux under nitrogen, then slowly add 4,4,4-trifluorobutan-2-one (7.59 mL, 1.0 eq) dropwise. Heat at reflux under nitrogen for 15 hours, then let cool to room temperature. Filter the reaction mixture to give an orange-red filtrate. To a separate flask, add tert-butyl 4-formylpiperidine-1-carboxylate (16.92 g, 1.0 eq) and ammonium acetate (15.28 g, 2.5 eq) in methanol (125 mL). Add the filtrate dropwise via addition funnel Stir overnight at room temperature under nitrogen. Concentrate to dryness in vacuo. Add water and make basic with 28% ammonium hydroxide in water. Extract with dichloromethane. Dry the organics over anhydrous magnesium sulfate, filter, and concentrate in vacuo. Purify by normal phase chromatography, eluting with hexanes to 10% methanol/dichloromethane, to give crude product as a yellow oil. Dilute with dichloromethane and saturated aqueous sodium bicarbonate. Separate the layers. Dry the organic layer over anhydrous sodium sulfate, filter, and concentrate in vacuo to give tert-butyl 4-(4-(2,2,2-trifluoroethyl)-1H-imidazol-2-yl)piperidine-1-carboxylate as a yellow solid (16.38 g, 62%). MS (ES) m/z=334 [M]$^+$.

e. tert-Butyl 4-(1-(2-(tetrahydro-2H-pyran-2-yloxy)ethyl)-4-(2,2,2-trifluoroethyl)-1H-imidazol-2-yl)piperidine-1-carboxylate Combine tert-butyl 4-(4-(2,2,2-trifluoroethyl)-1H-imidazol-2-yl)piperidine-1-carboxylate (3.52 g, 10.56 mmol), potassium hydroxide (1.91 g, 3.2 eq) (freshly powdered) and 2-(2-bromoethoxy)tetrahydro-2H-pyran (1.90 mL, 1.2 eq) in dimethyl sulfoxide (35 mL). Heat the reaction mixture at 50° C. overnight, then allow to cool to room temperature. Dilute with ethyl acetate. Wash with water followed by saturated aqueous sodium chloride. Dry the organics over anhydrous sodium sulfate, filter, and concentrate in vacuo.

Combine tert-butyl 4-(4-(2,2,2-trifluoroethyl)-1H-imidazol-2-yl)piperidine-1-carboxylate (4.34 g, 13.02 mmol), potassium hydroxide (2.33 g, 3.2 eq) (freshly powdered) and 2-(2-bromoethoxy)tetrahydro-2H-pyran (2.40 mL, 1.2 eq) in dimethyl sulfoxide (43 mL). Heat the reaction mixture at 50° C. overnight, then allow to cool to room temperature. Dilute with ethyl acetate. Wash with water followed by saturated aqueous sodium chloride. Dry the organics over anhydrous sodium sulfate, filter, and concentrate in vacuo.

Combine the two solids from the above reactions. Purify by silica gel chromatography, eluting with hexanes to 9:1 hexanes:ethyl acetate to 3:1 hexanes:ethyl acetate to 1:1 hexanes:ethyl acetate to 1:3 hexanes:ethyl acetate to ethyl acetate, to give tert-butyl 4-(1-(2-(tetrahydro-2H-pyran-2-yloxy)ethyl)-4-(2,2,2-trifluoroethyl)-1H-imidazol-2-yl)piperidine-1-carboxylate (4.19 g, 30%). MS (ES) m/z=462 [M]$^+$.

f. 2-(2-(Piperidin-4-yl)-4-(2,2,2-trifluoroethyl)-1H-imidazol-1-yl)ethanol dihydrochloride Combine tert-butyl 4-(1-(2-(tetrahydro-2H-pyran-2-yloxy)ethyl)-4-(2,2,2-trifluoroethyl)-1H-imidazol-2-yl)piperidine-1-carboxylate (3.12 g, 6.76 mmol), dichloromethane (88 mL), and methanol (35 mL). Add hydrogen chloride (17.3 mL, 10.2 eq) (4 M in dioxane) slowly. Stir overnight under nitrogen. Concentrate in vacuo to give 2-(2-(piperidin-4-yl)-4-(2,2,2-trifluoroethyl)-1H-imidazol-1-yl)ethanol dihydrochloride (2.37 g, 100%). MS (ES) m/z=278 [M]$^+$.

g. (R)-4-(4-(1-(2-Hydroxyethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one Add (R)-4-chloro-5-(trifluoromethyl)-5,6-dihydropyrido[2,3-d]pyrimidin-7(8H)-one (0.70 g, 2.78 mmol), 2-(2-(piperidin-4-yl)-4-(2,2,2-trifluoroethyl)-1H-imidazol-1-yl)ethanol dihydrochloride (1.17 g, 1.2 eq), N-methylpyrrolidinone (10 mL) and diisopropylethylamine (2.20 mL, 5.7 eq) in a microwave tube. Seal with crimp cap. Heat in a microwave reactor at 150° C. for one hour. Dilute the reaction mixture with saturated aqueous sodium bicarbonate and extract with ethyl acetate. Dry the organics over anhydrous sodium sulfate, filter, and concentrate in vacuo. Purify by normal phase chromatography, eluting with 5% methanol/dichloromethane to 10% methanol/dichloromethane to 10% 2 M ammonia in methanol/dichloromethane, to give (R)-4-(4-(1-(2-hydroxyethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one (0.93 g, 68%). MS (ES) m/z=493 [M]$^+$.

h. (R)-2-(2-(1-(7-Oxo-5-trifluoromethyl-5,6,7,8-tetrahydropyrido[2,3-d]pyrimidin-4-yl)piperidin-4-yl)-4-(2,2,2-trifluoroethyl)-1H-imidazol-1-yl)ethyl methanesulfonate Combine (R)-4-(4-(1-(2-hydroxyethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one (0.93 g, 1.88 mmol), dichloromethane (14 mL), and triethylamine (0.79 mL, 3.0 eq). Place under nitrogen and cool to 0° C. Add methanesulfonyl chloride (0.17 mL, 1.2 eq) dropwise. After 30 minutes, dilute with dichloromethane and quench with saturated aqueous sodium bicarbonate. Separate the layers. Dry the organics over anhydrous sodium sulfate, filter, and concentrate in vacuo to give (R)-2-(2-(1-(7-oxo-5-trifluoromethyl-5,6,7,8-tetrahydropyrido[2,3-d]pyrimidin-4-yl)piperidin-4-yl)-4-(2,2,2-trifluoroethyl)-1H-imidazol-1-yl)ethyl methanesulfonate as a yellow solid (1.07 g, 96%). MS (ES) m/z=571 [M]$^+$.

i. (R)-4-(4-(1-(2-(Azetidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one Combine (R)-2-(2-(1-(7-oxo-5-trifluoromethyl-5,6,7,8-tetrahydropyrido[2,3-d]pyrimidin-4-yl)piperidin-4-yl)-4-(2,2,2-trifluoroethyl)-1H-imidazol-1-yl)ethyl methanesulfonate (1.04 g, 1.82 mmol), dimethylformamide (9.3 mL), and azetidine (1.11 mL, 9.0 eq) under nitrogen. Heat the reaction mixture at 50° C. overnight, then allow to cool to room temperature. Dilute with ethyl acetate. Wash the organic layer with water. Dry the organics over anhydrous sodium sulfate, filter, and concentrate in vacuo. Purify by normal phase chromatography, eluting with 10% methanol/dichloromethane to 10% 2 M ammonia in methanol/dichloromethane, to give the title compound, (R)-4-(4-(1-(2-(azetidin-1-yl)ethyl)-4-(2,2,2-trifluoroethyl)-1H-imidazol-2-yl)piperidin-1-yl)-5-(trifluoromethyl)-5,6-dihydropyrido[2,3-d]pyrimidin-7(8H)-one, as a white solid (0.49 g, 51%). MS (ES) m/z=532 [M]$^+$.

EXAMPLE 97

(R)-5-Methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one

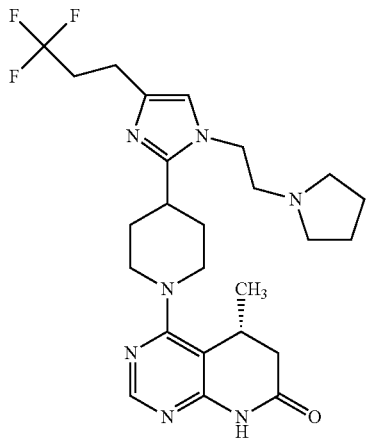 [SMILES: C[C@@H]1CC(=O)Nc2ncnc(N3CCC(c4nc(CCC(F)(F)F)cn4CCN4CCCC4)CC3)c21]

a. (R)-4-Chloro-5-methyl-5,6-dihydropyrido[2,3-d]pyrimidin-7(8H)-one

Prepare according to steps a to e of Example 92.

b. 5,5,5-Trifluoropentanal

Combine 3,3,3-triacetoxy-3-iodophthalide (17.91 g, 1.2 eq) and dichloromethane (95 mL). Add 5,5,5-trifluoro-1-pentanol (5.00 g, 35.18 mmol) in dichloromethane (238 mL) dropwise under nitrogen. After 4 hours, filter the reaction mixture through Celite®. Concentrate the filtrate in vacuo; combine with 50 mL of dichloromethane and wash with 1:1 10% sodium thiosulphate:aqueous sodium hydroxide (1N). Dry the organics with anhydrous sodium sulfate, filter, and concentrate in vacuo to give 5,5,5-trifluoropentanal as a colorless oil (2.13 g, 43%). $^1$H NMR (400 MHz, DMSO-d6) δ 9.61 (s, 1H), 2.50 (m, 2H), 2.21 (m, 2H), 1.66 (m, 2H).

c. 5,5,5-Trifluoro-2-oxopentanal

Combine 5,5,5-trifluoropentanal (2.01 g, 14.35 mmol), 1,4-dioxane (10 mL), selenium dioxide (1.62 g, 1.0 eq), water (0.51 mL), and acetic acid (0.69 mL). Heat the mixture at 90° C. and stir overnight. Allow the reaction mixture to cool to room temperature. Filter, wash the solids with dioxane. Combine the filtrate and washings to give 5,5,5-trifluoro-2-oxopentanal (2.21 g, 100%). GCMS m/z=154.

d. tert-Butyl 4-(4-(3,3,3-trifluoropropyl)-1H-imidazol-2-yl)piperidine-1-carboxylate Combine 28% ammonium hydroxide in water (18.6 mL), tert-butyl 4-formylpiperidine-1-carboxylate (3.04 g, 14.25 mmol), and methanol (22.6 mL). Place under nitrogen and cool to 0° C. Add 5,5,5-trifluoro-2-oxopentanal (2.21 g, 1.0 eq, as a solution in dioxane) under nitrogen. Allow to warm to room temperature. Stir for two days. Concentrate in vacuo and add ethyl acetate and saturated aqueous sodium chloride. Separate the layers. Extract the aqueous layer further with 9:1 dichloromethane:isopropyl alcohol. Dry the combined organic layers over anhydrous sodium sulfate, filter, and concentrate in vacuo. Purify by silica gel chromatography, eluting with hexanes to 1:1 hexanes:ethyl acetate to ethyl acetate, to give tert-butyl 4-(4-(3,3,3-trifluoropropyl)-1H-imidazol-2-yl)piperidine-1-carboxylate as a thick amber oil (2.32 g, 47%). MS (ES) m/z=348 [M]$^+$.

e. tert-Butyl 4-(1-(2-(pyrrolidin-1-yl)ethyl)-4-(3,3,3-trifluoropropyl)-1H-imidazol-2-yl)piperidine-1-carboxylate Combine tert-butyl 4-(4-(3,3,3-trifluoropropyl)-1H-imidazol-2-yl)piperidine-1-carboxylate (2.27 g, 6.53 mmol), potassium hydroxide (1.20 g, 3.3 eq) (freshly powdered), and 1-(2-chloroethyl)pyrrolidine hydrochloride (1.34 g, 1.2 eq) in dimethyl sulfoxide (100 mL). Heat the reaction mixture at 50° C. overnight, then allow to cool to room temperature. Dilute with ethyl acetate. Wash with water followed by saturated aqueous sodium chloride. Dry the organics over anhydrous sodium sulfate, filter, and concentrate in vacuo. Purify by silica gel chromatography, eluting with 4:1 dichloromethane: isopropyl alcohol, to give tert-butyl 4-(1-(2-(pyrrolidin-1-yl)ethyl)-4-(3,3,3-trifluoropropyl)-1H-imidazol-2-yl)piperidine-1-carboxylate as a thick yellow oil (0.73 g, 25%). MS (ES) m/z=445 [M]$^+$.

f. 4-(4-(3,3,3-Trifluoropropyl)-1-(2-(pyrrolidin-1-yl)ethyl)-1H-imidazol-2-yl)piperidine tris(2,2,2-trifluoroacetate)

Combine tert-butyl 4-(1-(2-(pyrrolidin-1-yl)ethyl)-4-(3,3,3-trifluoropropyl)-1H-imidazol-2-yl)piperidine-1-carboxylate (0.73 g, 1.64 mmol) and dichloromethane (16.2 mL). Place under nitrogen and cool to 0° C. Add trifluoroacetic acid (16.2 mL). After 1 hour, concentrate in vacuo to give 4-(4-(3, 3,3-trifluoropropyl)-1-(2-(pyrrolidin-1-yl)ethyl)-1H-imidazol-2-yl)piperidine tris(2,2,2-trifluoroacetate) (1.12 g, 100%). MS (ES) m/z=345 [M]$^+$.

g. (R)-5-Methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one Add (R)-4-chloro-5-methyl-5,6-dihydropyrido[2,3-d]pyrimidin-7(8H)-one (0.33 g, 1.66 mmol), 4-(4-(3,3,3-trifluoropropyl)-1-(2-(pyrrolidin-1-yl)ethyl)-1H-imidazol-2-yl)piperidine tris(2,2,2-trifluoroacetate) (1.12 g, 1.0 eq), N-methylpyrrolidinone (10 mL) and diisopropylethylamine (2.30 mL, 8.0 eq) in a microwave tube. Seal with crimp cap. Heat in a microwave reactor at 200° C. for 10 minutes. Dilute the reaction mixture with water and extract with ethyl acetate. Wash with saturated aqueous sodium chloride. Dry the organics over anhydrous sodium sulfate, filter, and concentrate in vacuo. Purify by normal phase chromatography, eluting with hexanes to 10% methanol/dichloromethane, to give the title compound, (R)-5-methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one, as an amber solid (0.23 g, 27%). MS (ES) m/z=506 [M]$^+$.

EXAMPLE 98

(R)-4-(4-(4-Ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one

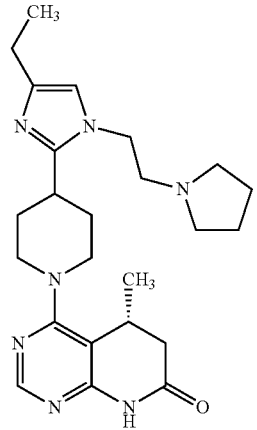 [SMILES: CCc1cn(CCN2CCCC2)c(C2CCN(c3ncnc4c3[C@H](C)CC(=O)N4)CC2)n1]

a. (R)-4-Chloro-5-methyl-5,6-dihydropyrido[2,3-d]pyrimidin-7(8H)-one

Prepare according to steps a to e of Example 92.

b. tert-Butyl 4-(1H-imidazol-2-yl)piperidine-1-carboxylate

Combine 28% ammonium hydroxide in water (373 mL), tert-butyl 4-formylpiperidine-1-carboxylate (127.00 g, 595.47 mmol), and methanol (508 mL). Stir at room temperature. After 15 minutes, add ethanedial (86.30 mL, 1.0 eq) (6.9 M in water) under nitrogen. After one hour, add water (1.14 L) dropwise over 45 minutes. Stir the resulting suspension overnight at room temperature. Filter and dry the resulting white solid under vacuum to give tert-butyl 4-(1H-imidazol-2-yl)piperidine-1-carboxylate (128.00 g, 86%). MS (ES) m/z=252 [M]+.

c. tert-Butyl 4-(4,5-diiodo-1H-imidazol-2-yl)piperidine-1-carboxylate

Combine tert-butyl 4-(1H-imidazol-2-yl)piperidine-1-carboxylate (50.00 g, 198.94 mmol) and dimethyl sulfoxide (200 mL). Add iodine (104.03 g, 2.1 eq) portionwise over 15 minutes. Heat the reaction mixture to 45° C. under nitrogen. After 30 minutes, add potassium hydroxide (19.70 g, 1.5 eq). Allow to cool to room temperature and stir overnight. Add the reaction mixture slowly to aqueous sodium bisulfate (1.25 L, 1.65 wt %). Stir the resulting suspension for 45 minutes. Filter, wash with water, and dry the resulting solid to give tert-butyl 4-(4,5-diiodo-1H-imidazol-2-yl)piperidine-1-carboxylate (98.00 g, 98%). MS (ES) m/z=504 [M]+.

d. tert-Butyl 4-(4,5-diiodo-1-(2-(pyrrolidin-1-yl)ethyl)-1H-imidazol-2-yl)piperidine-1-carboxylate Combine tert-butyl 4-(4,5-diiodo-1H-imidazol-2-yl)piperidine-1-carboxylate (86.00 g, 170.93 mmol) and potassium hydroxide (45.13 g, 4.0 eq) in N-methylpyrrolidinone (258 mL), maintaining the temperature below 40° C. Stir at room temperature for 25 minutes, then add 1-(2-chloroethyl)pyrrolidine hydrochloride (47.47 g, 1.6 eq). Heat the reaction mixture at 40° C. overnight, then allow to cool to room temperature.

Combine tert-butyl 4-(4,5-diiodo-1H-imidazol-2-yl)piperidine-1-carboxylate (10.00 g, 19.88 mmol) and potassium hydroxide (5.25 g, 4.0 eq) in N-methylpyrrolidinone (30 mL). Stir at 40° C. for 30 minutes, then add 1-(2-chloroethyl)pyrrolidine hydrochloride (5.52 g, 1.6 eq). Heat the reaction mixture at 40° C. overnight, then allow to cool to room temperature.

Combine the two reaction mixtures above. Add to water (3.36 L) and adjust the pH of the resulting mixture with 15% aqueous phosphoric acid to 7.5-8.0. Stir the suspension at 0-5° C. for one hour. Filter, wash with water, and dry the resulting solid under vacuum to give tert-butyl 4-(4,5-diiodo-1-(2-(pyrrolidin-1-yl)ethyl)-1H-imidazol-2-yl)piperidine-1-carboxylate (102.00 g, 89%). MS (ES) m/z=601 [M]+.

e. tert-Butyl 4-(4-iodo-1-(2-(pyrrolidin-1-yl)ethyl)-1H-imidazol-2-yl)piperidine-1-carboxylate Combine tert-butyl 4-(4,5-diiodo-1-(2-(pyrrolidin-1-yl)ethyl)-1H-imidazol-2-yl)piperidine-1-carboxylate (51.00 g, 84.96 mmol) and 2-methyltetrahydrofuran (357 mL). Cool the reaction mixture to 0° C. Add 2 M isopropylmagnesium chloride in tetrahydrofuran (55.22 mL, 1.3 eq) dropwise over 45 minutes, maintaining the temperature below 5° C. Add saturated aqueous ammonium chloride. Separate the layers. Wash the aqueous phase with methyl tert-butyl ether. Wash the organics with aqueous saturated sodium chloride. Dry the organics over anhydrous magnesium sulfate, decolor with charcoal, filter, and concentrate in vacuo to give tert-butyl 4-(4-iodo-1-(2-(pyrrolidin-1-yl)ethyl)-1H-imidazol-2-yl)piperidine-1-carboxylate as a yellow solid (39.50 g, 98%). MS (ES) m/z=475 [M]+.

f. tert-Butyl 4-(4-(1-hydroxyethyl)-1-(2-(pyrrolidin-1-yl)ethyl)-1H-imidazol-2-yl)piperidine-1-carboxylate; phosphoric acid Combine tert-butyl 4-(4-iodo-1-(2-(pyrrolidin-1-yl)ethyl)-1H-imidazol-2-yl)piperidine-1-carboxylate (40.00 g, 82.63 mmol) and tetrahydrofuran (600 mL). Cool to −70° C. under nitrogen. Add 2.5 M n-butyllithium in hexanes (67.76 mL, 2.1 eq) dropwise. Add acetaldehyde (23.22 mL, 5.0 eq) and stir for 15 minutes. Quench over aqueous saturated ammonium chloride (75 mL). Separate the layers. Wash the aqueous phase with methyl tert-butyl ether. Wash the organics with water and aqueous saturated sodium chloride. Dry the organics over anhydrous magnesium sulfate, filter, and concentrate in vacuo. Dissolve in ethanol. Add 85% aqueous phosphoric acid dropwise to achieve a suspension. Stir the mixture overnight at room temperature. Filter and dry the resulting off-white solid under vacuum to give tert-butyl 4-(4-(1-hydroxyethyl)-1-(2-(pyrrolidin-1-yl)ethyl)-1H-imidazol-2-yl)piperidine-1-carboxylate; phosphoric acid (28.00 g, 69%). MS (ES) m/z=393 [M]+.

g. tert-Butyl 4-(4-ethyl-1-(2-(pyrrolidin-1-yl)ethyl)-1H-imidazol-2-yl)piperidine-1-carboxylate; phosphoric acid Add palladium hydroxide on carbon (4.20 g, 60% wet, 0.15 g/g limiting reagent) to a solution of tert-butyl 4-(4-(1-hydroxyethyl)-1-(2-(pyrrolidin-1-yl)ethyl)-1H-imidazol-2-yl)piperidine-1-carboxylate; phosphoric acid (28.00 g, 57.08 mmol) in methanol (10 mL). Stir under a hydrogen atmosphere in a Parr system (150 psi, 60° C.) for six days. Stir further under a hydrogen atmosphere in a Parr system (300 psi, 80° C.) for seven days. Filter over Celite®. Concentrate the filtrate in vacuo and dilute with acetone (280 mL). Stir overnight at room temperature. Filter and dry the resulting white solid under vacuum to give tert-butyl 4-(4-ethyl-1-(2-(pyrrolidin-1-yl)ethyl)-1H-imidazol-2-yl)piperidine-1-carboxylate; phosphoric acid (23.00 g, 85%). MS (ES) m/z=377 [M]+.

h. 4-(4-Ethyl-1-(2-(pyrrolidin-1-yl)ethyl)-1H-imidazol-2-yl)piperidine

Combine tert-butyl 4-(4-ethyl-1-(2-(pyrrolidin-1-yl)ethyl)-1H-imidazol-2-yl)piperidine-1-carboxylate; phosphoric acid (18.27 g, 38.50 mmol) and water (9.1 mL). Add 12 M hydrochloric acid in water (9.63 mL, 3.0 eq) dropwise and stir at room temperature. After one hour, adjust the pH of the reaction mixture with 2 M aqueous sodium hydroxide to 10. Dilute with dichloromethane. Separate the layers. Wash the aqueous phase with dichloromethane. Wash the organics with aqueous saturated sodium chloride. Dry the organics over anhydrous magnesium sulfate, filter, and concentrate in vacuo to give 4-(4-ethyl-1-(2-(pyrrolidin-1-yl)ethyl)-1H-imidazol-2-yl)piperidine (7.70 g, 72%). MS (ES) m/z=277 [M]+.

i. (R)-4-(4-(4-Ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one Combine 4-(4-ethyl-1-(2-(pyrrolidin-1-yl)ethyl)-1H-imidazol-2-yl)piperidine (7.70 g, 27.86 mmol), (R)-4-chloro-5-methyl-5,6-dihydropyrido[2,3-d]pyrimidin-7(8H)-one (6.06 g, 1.1 eq), N-methylpyrrolidinone (25.4 mL) and triethylamine (4.27 mL, 1.1 eq). Stir overnight at 110° C. under nitrogen, then let cool to room temperature. Dilute with ethyl acetate and water. Adjust the pH with 2 M aqueous sodium hydroxide to 10. Separate the layers. Wash the aqueous phase with ethyl acetate. Wash the organics with aqueous saturated sodium chloride. Concentrate the organics in vacuo. Dilute with ethyl acetate and water. Adjust the pH to 5. Separate the layers; discard the organic layer. Adjust the pH of the aqueous phase with 2 M aqueous sodium hydroxide to 11. Wash the aqueous phase with ethyl acetate. Wash the organics with water and aqueous saturated sodium chloride. Concentrate the organics in vacuo. Dilute with 2-methyltetrahydrofuran:hexanes (15:85, 77 mL). Stir overnight at room temperature. Filter and dry the resulting white solid under vacuum to give the title compound, (R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one (7.90 g, 65%). MS (ES) m/z=438 [M]$^+$.

Formulation Examples

Mannitol Formulation

The compound of Example 73 (500 mg) and Mannitol (500 mg) are combined and blended dry for 2 hours or until a homogenous mixture is formed. A defined quantity of the blend (184.54 mg; equivalent to 92.29 mg of the compound of Example 73) is weighed by hand into a hard gelatin capsule shell bottom and the upper capsule shell combined to enclose the blend. As an alternative, the blend of the compound of the invention and Mannitol may be transferred into hard gelatin capsules using equipment such as the Xcelodose®S precision powder micro-dosing system and sealing machine.

PEG400 Formulation

The compound of Example 73 (126 mg) and PEG400 (621.5 mg) are combined in a container and heated to 70° C. using a stirrer at 250 rpm for two hours or until the compound of Example 73 is completely dissolved. A defined quantity of the blend is weighed by hand or via an automated system into a soft gelatin capsule shell bottom and the upper capsule shell combined to enclose the capsule.

AKT1 In Vitro Enzyme Assay

Compound $IC_{50}$ values against AKT1 target are determined using the AKT1 Transcreener™ Kinase ADP-FP Assay. This assay assesses the activity of AKT1 in the presence of compound inhibitors by measuring the concentration of adenosine diphosphate (ADP) formed in a kinase reaction. The kinase reactions (25 µL reaction volumes) are performed in 96-well half-area black polystyrene plates. Adenosine triphosphate (ATP) is added to start the reactions. Final reaction conditions are 56 millimolar N-2-hydroxyethylpiperazine-N'-2-ethanesulfonic acid (HEPES) pH 7.4, 0.008% TRITON™ X-100, 5 millimolar magnesium chloride, 30 micromolar Crosstide peptide, 20 micromolar ATP, hAKT1 Human Recombinant, V-AKT Murine Thymoma Viral Oncogene Homolog 1, histidine-tagged, expressed in insect cells, 4% dimethylsulfoxide and serial dilutions of compound (diluted 1:3 from 20,000 to 1 nanomolar). Following ATP addition, the reactions are incubated at room temperature for 60 minutes and then quenched with the addition of 25 µL of a quench detection reagent containing 52 millimolar HEPES pH 7.5, 20 millimolar ethylenediaminetetraacetic acid (EDTA), 0.4 molar sodium chloride, 0.02% BRIJ-35™, 10 microgram/milliliter anti-ADP antibody, and 4 nanomolar ADP Far Red Tracer. Quenched reactions are incubated for 4-16 hours, and then read in a Tecan Ultra Evolution plate reader in Fluorescence Polarization mode using polarizing filters of $Ex_{612\,nm}$ and $Em_{633\,nm}$ wavelength. Millipolarization (mP) raw data is converted to micromolar ADP using a prepared ADP/ATP standard curve (Huss et al, Development of a Transcreener™ Kinase Assay for Protein Kinase A and Demonstration of Concordance of Data with a Filter-Binding Assay Format, Journal of Biomolecular Screening, 12(4); 2007, 578-584). The $IC_{50}$ value for each compound is derived using percent inhibition data which is calculated using the micromolar ADP reaction data relative to on-plate controls (active enzyme versus 100 millimolar inhibited enzyme controls). The percent inhibition and ten-point compound concentration data is then fit to a four-parameter logistic equation using ACTIVITYBASE 4.0 (*Assay Guidance Manual Version* 5.0, 2008, Eli Lilly and Company and NIH Chemical Genomics Center).

Example 41 was tested essentially as described above and was found to have an $IC_{50}$ of 0.017 µM. This demonstrates that Example 41 is active as an AKT1 inhibitor.

AlphaScreen SureFire Detection phosphorylated GSK3β (S9) in U87MG Cells

The effect of compounds on the formation of endogenous phosphorylated GSK3β serine 9 (pGSK3β) are measured using the AlphaScreen SureFire® for pGSK3β (TGRGBS10K). This is a homogeneous assay format using immuno-sandwich capture of the phosphorylated analyte followed by detection using antibody-coated Alphascreen beads to generate an amplified signal.

U87MG cells are maintained in U87MG growth medium consisting of DMEM supplemented with 10% Fetal bovine serum, 1% Nonessential amino acids and 1% sodium pyruvate. For the assay, cells are harvested by standard procedures and then counted using Vi-Cell. Cells (50,000/well) are plated in 100 µL of U87MG growth medium into Costar #3596 96 well plates. Plates are incubated overnight at 37° C., 5% $CO_2$.

On the day of the assay, cells are treated with 20 µL/well compound diluted in media containing 6% dimethylsulfoxide. After 1 hour at 37° C., the medium is removed and 50 µL of SureFire Lysis Buffer (TGR Biosciences SureFire® Kit component) is added per well and incubation continued at room temperature for 10 minutes with gentle shaking. The lysate (6.0 µL) is transferred to a 384 well ProxiPlate™ (Perkin Elmer #6006280). A mixture containing 0.96 µL activation buffer, 0.19 µL each donor and acceptor beads, and 8.7 µL Reaction Buffer for pGSK3β assay (TGR Biosciences, TGRGBS10K) is added to each well. The plate is sealed with foil, incubated at room temperature for 4 hours with gentle shaking and then read on Perkin Elmer EnVision equipped with a TurboModule using standard AlphaScreen® settings ($Ex_{680\,nm}$ and $Em_{520-620\,nm}$). The percent inhibition determined from controls on each plate and ten-point compound concentration data are then fit to a four-parameter logistic equation using ACTIVITYBASE 4.0 (*Assay Guidance Manual Version* 5.0, 2008, Eli Lilly and Company and NIH Chemical Genomics Center).

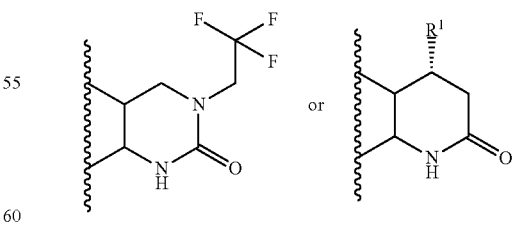

All the exemplified compounds in which A is have been tested essentially as described above and have an $IC_{50}$ of less than or equal to 2.8 µM. Example 41 was tested essentially as described above and was found to have an $IC_{50}$ of 1.5 µM.

This demonstrates the ability of compounds of the present invention to inhibit AKT activity.

Determination of AKT In Vivo Target Inhibition (IV)

In Vivo Target Inhibition by a Single IV Injection:

Exponentially growing U87MG cells derived from a human glioblastoma are implanted subcutaneously in the rear flank of athymic rats. When the tumors reach the size of 200-250 mm³, compounds are administered to the animals by a single IV injection in a dose-response study or in a time-course study. At the end of each treatment, animals are asphyxiated with $CO_2$. Tumors are harvested by surgical excision, quickly frozen in liquid nitrogen and stored at −80° C. until analysis. Sera are prepared from blood harvested from the heart by cardiac puncture and stored at −80° C. until analysis.

Sample Analysis:

The AKT inhibitor is extracted from serum with acetonitrite/methanol and analyzed alongside an internal standard by LC/MS/MS. Compound serum exposure and the calculation of TME $C_{50}$ (threshold minimum effective concentration) in the case of dose response studies.

Tumors are homogenized in 2 volumes of a lysis buffer containing 25 mM Tris (pH 7.5), Roche complete protease inhibitors, and 1 mM vanadate with Powergen 125 homogenizer, then sequentially passed through an 18 gauge needle and a 23 gauge needle. Soluble cytoplasmic extracts are collected from the supernatant fraction after the lysates are centrifuged for 30 minutes at 20,000×g. Protein concentrations in the cytoplasmic extracts are determined with a BCA kit. Phospho-GSK3b (pGSK3b) in the soluble extracts is analyzed with the ELISA Kit. For each study, percent inhibitions are calculated relative to the vehicle control group and ANOVA analysis is performed using the JMP software package for the determination of statistical significance.

Example 78 was tested essentially as described above in the in-vivo target inhibition assay and was found to have the following activity:

| IV Dose (mpk) | Post IV Dose (hr) | p(S9)GSK 3β - % inhibition |
|---|---|---|
| 20 | 4 | 48 (n = 2) |

This demonstrates the ability of Example 78 to inhibit AKT in vivo.

ROCK2 In Vitro Enzyme Assay

Compound $IC_{50}$ values against ROCK2 kinase are determined using the ROCK2 Transcreener™ Kinase ADP-FP Assay. This assay assesses the activity of ROCK2 in the presence of compound inhibitors by measuring the concentration of ADP formed in a kinase reaction. The kinase reactions (25 µL reaction volumes) are performed in 96-well half-area black polystyrene plates. Enzyme is added to start the reactions. Final reaction conditions are 20 millimolar 3-(N-Morpholino)-propanesulfonic acid pH 7.4, 4 millimolar beta-glycero-phosphate, 0.01% TRITON™ X-100, 5 millimolar magnesium chloride, 25 micromolar peptide substrate (sequence RFARKGSLRQKNV (SEQ ID NO:1)), 10 micromolar ATP, ROCK2 Human recombinant enzyme (residues 11-552, histidine-tagged, expressed in insect cells), 4% dimethysulfoxide and serial dilutions of compound (diluted 1:3 from 20,000 to 1 nanomolar). Following enzyme addition, the reactions are incubated at room temperature for 60 minutes and then stopped with the addition of 25 µL of a quench detection reagent containing 52 millimolar HEPES pH 7.5, 20 millimolar EDTA, 0.4 molar sodium chloride, 0.02% BRIJ-35™, 10 microgram/milliliter anti-ADP antibody, and 4 nanomolar ADP Far Red Tracer. Quenched reactions are incubated for 4-16 hours, and then read in a Tecan Ultra Evolution plate reader in Fluorescence Polarization mode using polarizing filters of $Ex_{612\,nm}$ and $Em_{633\,nm}$ wavelength. Millipolarization (mP) raw data was converted to micromolar ADP using an ADP/ATP standard curve (Huss et al, Development of a Transcreener™ Kinase Assay for Protein Kinase A and Demonstration of Concordance of Data with a Filter-Binding Assay Format, Journal of Biomolecular Screening, 12(4); 2007, 578-584). The $IC_{50}$ value for each compound is derived using percent inhibition data which is calculated using the micromolar ADP reaction data relative to on-plate controls (active enzyme versus 100 millimolar EDTA-inhibited enzyme controls). The percent inhibition and ten-point compound concentration data was then fit to a four-parameter logistic equation using ACTIVITYBASE 4.0 (*Assay Guidance Manual Version* 5.0, 2008, Eli Lilly and Company and NIH Chemical Genomics Center).

All the exemplified compounds in which A is

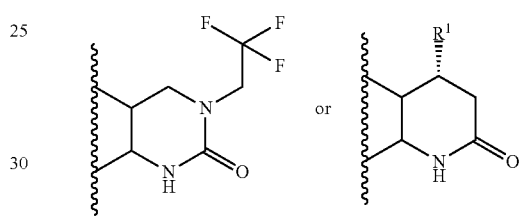

have been tested essentially as described above and have an $IC_{50}$ of greater than or equal to 20 µM. Example 41 was tested essentially as described above and was found to have an $IC_{50}$ of greater than 20 µM.

Preferred compounds of the invention have low ROCK2 activity.

Cell Proliferation and Combination Studies

The proliferation assay uses the CellTiter-Glo Luminescent Cell Viability Assay System (commercially available from Promega) to determine the cell number of viable cells in culture based on quantitation of the ATP present, which signals the presence of metabolically active cells.

The cells are plated in 96-well plate at 2000 cells/well in volume of 50 µL medium (DMEM, 10% FBS, 25 mM HEPES, 1.0 mM Sodium Pyruvate, and 0.1 mM Non Essential Amino Acids) except column 1 with medium only as blank control. The plates are incubated overnight at 37° C. and 5% $CO_2$. On the next day, compound stocks are prepared at 40 mM in DMSO (500×) and serially diluted in DMSO in a 96-well round bottom polypropylene plate. Compounds are assayed at 10 concentrations in duplicate, 4 compounds per plate.

4 µL of the serial DMSO dilutions are transferred to a 96 deep-well plate and 1 mL complete culture medium is added to create 2× stock for dosing. 50 µL of each 2× dosing stock is gently transferred to the corresponding well of the cell plate resulting in a 0.2% DMSO concentration and a 100 µL final volume. 50 mL medium are added to the Control columns (Column 12) and background columns (Column 1). Cells are incubated with compound for at 37° C., 5% $CO_2$ for 72 hr.

After incubation, 100 µL of the pre-prepared CellTiter-Glo reagent (Promega, Cat: G7571) is added in each well and then the cells are homogenized by mixing on an orbital shaker for 2 min and incubated at RT for 10 minutes to allow luminescent signal stabilization Luminescent raw data is recorded on Wallac Victor V plate reader and the $IC_{50}$ value for each compound is generated using percent inhibition data. A four-parameter logistic curve is fit to each dose response.

Combination studies use the fixed ratio method, where the other therapeutic agent and the compound of the present invention are present in fixed ratios of concentrations corresponding to the IC50 equivalents of single agents. The read out for the combination studies is cell proliferation in respective cell lines using Cell Titer Glo reagents. Controls are processed similarly but without the compounds. Analysis of the data is done according to the method described in Zhao et. Al. (Clinical Cancer Research 10, 7994-8004, Dec. 1, 2004) utilizing an internally developed web based tool. A combination index is calculated for each cell proliferation inhibition activity level according to the equation below.

Combination Index at activity level $x$=[Concentration of other therapeutic agent in the combination at the activity level $x$/IC$x$ of the other therapeutic agent]+[Concentration of the compound of the present invention in the combination at the activity level $x$/IC$x$ of the compound of the present invention]

For clarity, Combination index values at 50% inhibition are summarized below.

| Example | Other Therapeutic Agent | Cell Line | Combination Index at 50% Inhibition | 95% Confidence Interval |
|---|---|---|---|---|
| 77 | Pemetrexed | Calu6 | 0.93 | 0.68-1.24 |
| 77 | Pemetrexed | NCI-H1975 | 1.73 | 0.83-3.71 |
| 77 | Cisplatin | A2780 | 0.93 | 0.74-1.18 |
| 73 | Cisplatin | H1155 | 0.82 | 0.62-1.10 |
| 77 | Cisplatin | Calu6 | 0.86 | 0.65-1.12 |
| 77 | Cisplatin | NCI-H1975 | 0.77 | 0.65-0.91 |
| 77 | Cisplatin | SK0V3 | 1.00 | 0.89-1.12 |
| 77 | Cisplatin | NCIH460 | 0.76 | 0.70-0.82 |
| 77 | Cisplatin | NCIH460 | 0.91 | 0.82-1.01 |
| 77 | Docetaxel | Calu6 | 0.65 | 0.54-0.77 |
| 77 | Docetaxel | NCIH460 | 0.82 | 0.76-0.88 |
| 77 | Docetaxel | NCI-H1975 | 1.13 | 0.91-1.37 |
| 77 | Doxorubicin | A2780 | 0.85 | 0.59-1.28 |
| 77 | Doxorubicin | SK0V3 | 1.12 | 0.96-1.30 |
| 77 | Erlotinib | H1155 | 0.16 | 0.03-0.40 |
| 77 | Erlotinib | H1155 | 0.73 | 0.58-0.92 |
| 73 | Erlotinib | H1155 | 0.38 | 0.31-0.46 |
| 73 | Erlotinib | H1155 | 0.77 | 0.58-1.03 |
| 77 | Gemcitabine | H1155 | 0.43 | 0.26-0.66 |
| 73 | Gemcitabine | H1155 | 0.87 | 0.70-1.08 |
| 77 | Gemcitabine | Calu6 | 1.16 | 0.60-2.02 |
| 77 | Gemcitabine | NCIH460 | 0.88 | 0.76-1.01 |
| 77 | Gemcitabine | NCI-H1975 | 0.55 | 0.29-0.87 |
| 77 | Gemcitabine | AsPC1 | 0.23 | 0.10-0.48 |
| 77 | Gemcitabine | BxPC3 | 1.13 | 0.69-1.94 |
| 77 | Gemcitabine | H1650 | 0.43 | 0.20-0.78 |
| 77 | Gemcitabine | HCC827 | 0.17 | 0.02-1.83 |
| 77 | Gemcitabine | MCF-7 | 0.10 | 0.02-0.33 |
| 77 | Gemcitabine | MDA-MB-231 | 0.39 | 0.13-2.18 |
| 77 | Irinotecan | RKO | 0.83 | 0.71-0.96 |
| 73 | Pemetrexed | H1155 | 0.29 | 0.13-1.52 |
| 77 | Rapamycin | AsPC1 | 0.22 | 0.08-0.50 |
| 77 | Rapamycin | BxPC3 | 0.15 | 0.06-0.33 |
| 77 | Rapamycin | MCF-7 | 0.46 | 0.30-0.75 |
| 77 | Rapamycin | HCC-827 | 1.13 | 0.22-7.57 |
| 77 | Rapamycin | H1650 | 0.07 | 0.00-57.13 |
| 77 | Rapamycin | MDA-MB-231 | 0.01 | 0.00-0.10 |
| 77 | Tamoxifen | MCF-7 | 0.74 | 0.49-1.10 |
| 77 | Erlotinib | Calu6 | 0.20 | 0.11-0.41 |
| 77 | Erlotinib | NCIH460 | 0.64 | 0.57-0.71 |
| 77 | Erlotinib | NCI-H1975 | 0.47 | 0.39-0.55 |
| 77 | Erlotinib | AsPC1 | 0.23 | 0.11-0.42 |
| 77 | Erlotinib | BxPC3 | 0.36 | 0.22-0.56 |
| 77 | Erlotinib | H1650 | 0.04 | 0.01-0.11 |
| 77 | Erlotinib | HCC827 | 1.87 | 0.01-9.04 |
| 77 | Erlotinib | MCF-7 | 0.58 | 0.37-0.94 |
| 77 | Erlotinib | MDA-MB-231 | 0.05 | 0.01-0.90 |
| 77 | Tasisulam | Calu6 | 1.16 | 0.80-1.69 |
| 77 | Paclitaxel | MCF-7 | 0.60 | 0.44-0.83 |
| 73 | Paclitaxel | MCF-7 | 0.56 | 0.42-0.74 |
| 77 | Paclitaxel | MDA-MB-231 | 1.13 | 0.79-1.61 |
| 73 | Paclitaxel | MDA-MB-231 | 1.25 | 0.98-1.60 |

Determination of AKT In Vivo Target Inhibition (Oral and Parenteral)

U87MG human glioblastoma cells ($5\times10_6$) are subcutaneously implanted into the flank of athymic nude mice in 0.2 mL of matrigel. Two weeks post-implantation, mice are dosed orally or parenterally according to a time course, single dose/single time point, or dose response protocol for the determination of $TMED_{50}$ (threshold minimum effective dose). Tumors are flash frozen at harvest and blood is collected for the determination of parent compound plasma exposure and the calculation of $TMEC_{50}$ (threshold minimum effective concentration) in the case of dose response studies. Tumors or tissues are pulverized in liquid $N_2$ and lysed in 400 µL of XY Lysis Buffer (10 µg/mL Leupeptin, 10 µg/mL Trypsin-Chymotrypsin Inhibitor, 10 µg/mL Tosyl phenyl-alanyl chloromethyl ketone, 10 µg/mL Aprotinin, 60 mM Beta-Glycerol Phosphate, 1% Triton X100, 25 mM Tris pH 7.5, 2.5 mM Pyrophosphate, 150 mM NaCl, 2 mM p-tosyl-L-arginine methyl ester, 15 mM para-nitrophenyl phosphate, 5 mM Benzamidine, 1 mM Na Vanadate, 10 mM NaF, 50 µg/mL phenylmethane sulfonyl fluoride, 1 mM 1,4-Dithiothreitol (DTT), 15 mM EDTA pH 8.0, 5 mM EGTA pH 8.0, 1 µM Microcystin, 1 µM Okadaic Acid, and 1 Roche Complete protease inhibitor mini-tablet per 10 mL) using Lysing Matrix D tubes (MP Biomedicals, Solon, Ohio, cat #6913-500) and a BIO101 Thermo Savant Fast Prep FP12. Lysates are aliquoted and either assayed immediately or stored at −80° C. for later testing. In Vivo Target Inhibition of AKT is measured utilizing Meso Scale Discovery (Gaithersburg, Md.) ELISA technology to assess effects on phosphorylation of the downstream effectors FOXO, PRAS40 and GSK3β(S9). In summary, 20 µg of lysate is added to carbon electrode containing 96-well plates pre-spotted with the appropriate capture antibodies. The protein of interest is probed using a ruthenium labeled detection antibody. Upon the passage of current over the electrode in the presence of read buffer containing the co-reactant TPA, electro-chemiluminescence results in the generation of light which is quantified and recorded using the MSD Sector 6000 instrument. For each study, percent inhibitions are calculated relative to the vehicle control group and ANOVA analysis is performed using the JMP software package for the determination of statistical significance.

Example 26 was tested essentially as described above in the AKT in vivo target inhibition assay and was found to have the following activity after 2 hours at 12.5 mg/kg (mean of 6 animals per group):

| Mean Plasma Glucose (ng/ml) | Mean % Inhibition pGSK3β (S9) | Mean % Inhibition pAKT (S473) | Mean % Inhibition pPRAS40 (T246) | Mean % Inhibition FOXO3a (T32) |
|---|---|---|---|---|
| 234.7 | 34.4 | 21.7 | 8.1 | 36.8 |

This demonstrates the ability of Example 26 to inhibit AKT in vivo.

The invention claimed is:

1. A compound of the formula:

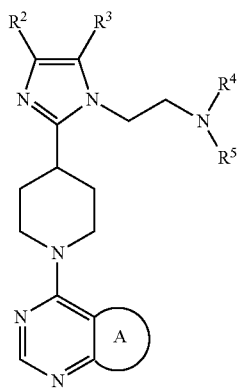

wherein:
A is

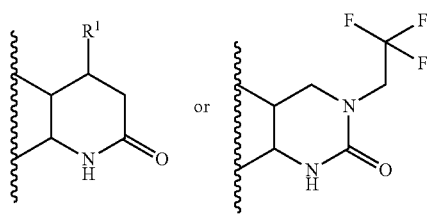

$R^1$ is $CH_3$, $CH_2CH_3$ or $CF_3$;
$R^2$ is H, $CF_3$, $CH_2CF_3$, $CH_2CH_2CF_3$, $C_1$-$C_4$ alkyl, $C_3$-$C_6$ cycloalkyl, CN, Cl, Br, CH=$CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H;
or $R^2$ and $R^3$ are both Cl;
$R^4$ is H and $R^5$ is $CH_3$, $C(CH_3)_3$, $CH(CH_3)_2$, cyclobutyl, cyclopentyl, $CH_2$-cyclopropyl, $C(CH_3)_2CH_2CH_3$ or tetrahydropyran-4-yl;
or $R^4$ and $R^5$ are both $CH_3$;
or $R^4$ and $R^5$ together with the N to which they are attached form a pyrrolidine, optionally substituted by hydroxy at the 3-position, or an azetidine;
or a pharmaceutically acceptable salt thereof.

2. The compound according to claim 1, or a pharmaceutically acceptable salt thereof, wherein A is:

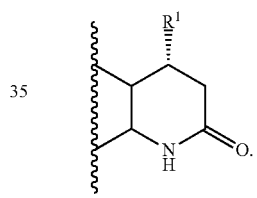

3. The compound according to claim 1, or a pharmaceutically acceptable salt thereof, wherein $R^1$ is $CH_3$ or $CF_3$.

4. The compound according to claim 1, or a pharmaceutically acceptable salt thereof, wherein $R^2$ is $CF_3$, $CH_2CF_3$, $CH_2CH_2CF_3$, $CH_2CH_3$, $(CH_2)_2CH_3$, cyclopropyl, Br, $CH_2CH_2OCH_3$ or tetrahydropyran-4-yl, and $R^3$ is H.

5. The compound according to claim 4, or a pharmaceutically acceptable salt thereof, wherein $R^2$ is $CH_2CF_3$, $CH_2CH_2CF_3$ or $CH_2CH_3$ and $R^3$ is H.

6. The compound according to claim 1, or a pharmaceutically acceptable salt thereof, wherein $R^4$ is H and $R^5$ is $C(CH_3)_3$; or $R^4$ and $R^5$ together with the N to which they are attached form a pyrrolidine or an azetidine.

7. The compound according to claim 6, or a pharmaceutically acceptable salt thereof, wherein $R^4$ and $R^5$ together with the N to which they are attached form a pyrrolidine or an azetidine.

8. The compound according to claim 1 selected from:
(R)-5-methyl-4-(4-(1-(2-(pyrrolidin-1-yl)ethyl)-4-(3,3,3-trifluoropropyl)-1H-imidazol-2-yl)piperidin-1-yl)-5,6-dihydropyrido[2,3-d]pyrimidin-7(8H)-one;
(R)-4-(4-(4-ethyl-1-(2-(pyrrolidin-1-yl)ethyl)-1H-imidazol-2-yl)piperidin-1-yl)-5-methyl-5,6-dihydropyrido[2,3-d]pyrimidin-7(8H)-one; and
(R)-4-(4-(1-(2-(azetidin-1-yl)ethyl)-4-(2,2,2-triflouroethyl)-1H-imidazol-2-yl)piperidin-1-yl)-5-(triflouromethyl)-5,6-dihydropyrido[2,3-d]pyrimidin-7(8H)-one, or pharmaceutically acceptable salts thereof.

9. A pharmaceutical formulation comprising a compound of the formula:

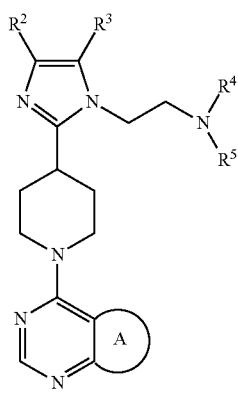

wherein:
A is

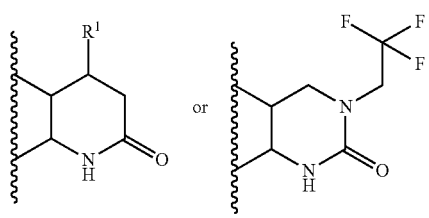

$R^1$ is $CH_3$, $CH_2CH_3$ or $CF_3$;

$R^2$ is H, $CF_3$, $CH_2CF_3$, $CH_2CH_2CF_3$, $C_1$-$C_4$ alkyl, $C_3$-$C_6$ cycloalkyl, CN, Cl, Br, $CH=CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H;

or $R^2$ and $R^3$ are both Cl;

$R^4$ is H and $R^5$ is $CH_3$, $C(CH_3)_3$, $CH(CH_3)_2$, cyclobutyl, cyclopentyl, $CH_2$-cyclopropyl, $C(CH_3)_2CH_2CH_3$ or tetrahydropyran-4-yl;

or $R^4$ and $R^5$ are both CH3;

or $R^4$ and $R^5$ together with the N to which they are attached form a pyrrolidine, optionally substituted by hydroxy at the 3-position, or an azetidine;

or a pharmaceutically acceptable salt thereof, and a pharmaceutically acceptable carrier, diluent or excipient.

10. A method for treating lung cancer, breast cancer or glioblastoma in a mammal comprising administering to a mammal in need of such treatment an effective amount of a compound of the formula:

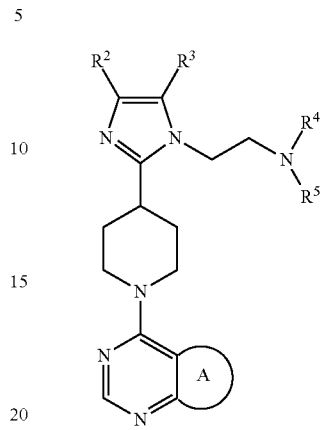

wherein:
A is

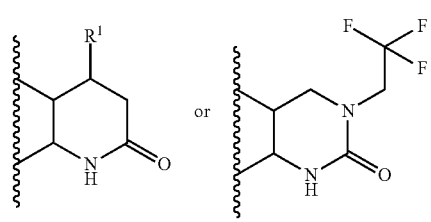

or
$R^1$ is $CH_3$, $CH_2CH_3$ or $CF_3$;.

$R^2$ is H, $CF_3$, $CH_2CF_3$, $CH_2CH_2CF_3$, $C_1$-$C_4$ alkyl, $C_3$-$C_6$ cycloalkyl, CN, Cl, Br, $CH=CH_2$, $CH_2CH_2OCH_3$, $C(CH_3)_2CH_2OCH_3$ or tetrahydropyran-4-yl, wherein $C_3$-$C_6$ cycloalkyl is optionally substituted by methyl at the 1-position and tetrahydropyran-4-yl is optionally substituted with methyl at the 4-position, and $R^3$ is H;

or $R^2$ and $R^3$ are both Cl;

$R^4$ is H and $R^5$ is $CH_3$, $C(CH_3)_3$, $CH(CH_3)_2$, cyclobutyl, cyclopentyl, $CH_2$-cyclopropyl, $C(CH_3)_2CH_2CH_3$ or tetrahydropyran-4-yl;

or $R^4$ and $R^5$ are both CH3;

or $R^4$ and $R^5$ together with the N to which they are attached form a pyrrolidine, optionally substituted by hydroxy at the 3-position, or an azetidine;

or a pharmaceutically acceptable salt thereof.

* * * * *

```
SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Arg Phe Ala Arg Lys Gly Ser Leu Arg Gln Lys Asn Val
1               5                   10
```